(12) United States Patent
Pang et al.

(10) Patent No.: US 7,807,641 B2
(45) Date of Patent: *Oct. 5, 2010

(54) METHODS AND REAGENTS FOR TREATING GLUCOSE METABOLIC DISORDERS

(75) Inventors: Kevin Pang, Belmont, MA (US); Kuanghui Lu, Brookline, MA (US)

(73) Assignee: Curis, Inc., Cambridge, MA (US)

( * ) Notice: Subject to any disclaimer, the term of this patent is extended or adjusted under 35 U.S.C. 154(b) by 468 days.

This patent is subject to a terminal disclaimer.

(21) Appl. No.: 11/702,776

(22) Filed: Feb. 6, 2007

(65) Prior Publication Data

US 2008/0188406 A1 Aug. 7, 2008

Related U.S. Application Data

(60) Division of application No. 10/855,676, filed on May 27, 2004, which is a continuation of application No. 09/634,363, filed on Aug. 9, 2000, now abandoned, which is a continuation-in-part of application No. 09/500,817, filed on Feb. 10, 2000, now abandoned, which is a continuation-in-part of application No. 09/499,526, filed on Feb. 10, 2000, now Pat. No. 7,396,809.

(60) Provisional application No. 60/119,575, filed on Feb. 10, 1999, provisional application No. 60/119,577, filed on Feb. 10, 1999.

(51) Int. Cl.
*A61K 38/22* (2006.01)
*C07K 14/575* (2006.01)

(52) U.S. Cl. .................................. 514/12; 530/324
(58) Field of Classification Search .................. None
See application file for complete search history.

(56) References Cited

U.S. PATENT DOCUMENTS

| 4,683,195 A | 7/1987 | Mullis et al. |
| 4,683,202 A | 7/1987 | Mullis |
| 4,839,343 A | 6/1989 | Waeber et al. |
| 4,891,357 A | 1/1990 | Kalra |
| 4,892,538 A | 1/1990 | Aebischer et al. |
| 5,423,872 A | 6/1995 | Cigaina et al. |
| 5,459,039 A | 10/1995 | Modrich et al. |
| 5,498,531 A | 3/1996 | Jarrell |

(Continued)

FOREIGN PATENT DOCUMENTS

EP 0 992 239 B1 3/2003

(Continued)

OTHER PUBLICATIONS

Marshall, A hierarchical approach to peptidomimetic design. Tetrahedron, vol. 49, Issue 17, pp. 3547-3558 (Mar. 23, 1993).*

(Continued)

*Primary Examiner*—Marianne P Allen
*Assistant Examiner*—Regina M DeBerry
(74) *Attorney, Agent, or Firm*—Ropes & Gray LLP

(57) ABSTRACT

The invention relates to methods for potentiating, enhancing or restoring glucose responsivity in pancreatic islets or cells. The methods can be used as therapies for diseases caused by, or coincident with, aberrant glucose metabolism, such as Type II Diabetes Mellitus.

34 Claims, 16 Drawing Sheets

U.S. PATENT DOCUMENTS

| | | | |
|---|---|---|---|
| 5,545,549 | A | 8/1996 | Gerald et al. |
| 5,574,010 | A | 11/1996 | McFadden |
| 5,604,203 | A | 2/1997 | Balasubramaniam |
| 5,696,093 | A | 12/1997 | Tseng et al. |
| 5,912,227 | A | 6/1999 | Croom et al. |
| 5,916,869 | A | 6/1999 | Croom, Jr. et al. |
| 5,939,462 | A | 8/1999 | Connell et al. |
| 5,968,819 | A | 10/1999 | Gerald et al. |
| 5,980,945 | A | 11/1999 | Ruiz |
| 5,989,920 | A | 11/1999 | Gerald et al. |
| 6,013,622 | A | 1/2000 | Bruno et al. |
| 6,391,343 | B1 | 5/2002 | Yen |
| 6,558,708 | B1 | 5/2003 | Lin |
| 6,569,832 | B1 | 5/2003 | Knudsen et al. |
| 7,396,809 | B1 * | 7/2008 | Lu et al. .................. 514/2 |
| 2002/0094346 | A1 | 7/2002 | Lin |
| 2003/0224983 | A1 | 12/2003 | Nielsen |
| 2004/0228846 | A1 | 11/2004 | Pang et al. |
| 2009/0082309 | A1 | 3/2009 | Bachovchin et al. |

FOREIGN PATENT DOCUMENTS

| | | |
|---|---|---|
| WO | WO-89/01967 | 3/1989 |
| WO | WO-90/02580 | 3/1990 |
| WO | WO-90/15637 | 12/1990 |
| WO | WO-91/10425 | 7/1991 |
| WO | WO-91/10470 | 7/1991 |
| WO | WO-9116917 | 11/1991 |
| WO | WO-94/16101 | 7/1994 |
| WO | WO-9517906 | 7/1995 |
| WO | WO-9616542 | 6/1996 |
| WO | WO-99/15516 A1 | 4/1999 |
| WO | WO-00/47219 A2 | 8/2000 |
| WO | WO-00/68197 A1 | 11/2000 |
| WO | WO-01/62737 A2 | 8/2001 |
| WO | WO-01/76631 A2 | 10/2001 |
| WO | WO-03/026591 A2 | 4/2003 |

OTHER PUBLICATIONS

Ngo et al. The Protein Folding Problem and Tertiary Structure, pp. 433-440 and 492-495 (1994).*

Adrian, T.E., et al., "Human Distribution and Release of a Putative New Gut Hormone, Peptide YY," Gastroenterology, 89:1070-7 (1985).

Ahren et al., "Peptide YY Does not Inhibit Glucose-Stimulated Insulin Secretion in Humans," European Journal of Endocrinology 134:362-365 (1996).

Allen, J.M., et al., "Effects of Peptide YY and Neuropeptide Y on Gastric Emptying in Man," Digestion, 30:255-262 (1984).

Ando, R.; et al., "Feeding responses to several neuropeptide Y receptor agonists in the neonatal chick," Eur J Pharmacol., 427(1):53-59 (2001).

Andres, C. J., et al., "Differentially functionalized diamines as novel ligands for the $NPY_2$ receptor," Bioorg Med Chem Lett., 13(17):2883-2885 (2003).

Aponte et al., "Meal-Induced Peptide Tyrosine Tyrosine Inhibition of Pancreatic Secretion in the Rat," The FASEB Journal 3:1949-1955 (1989).

Aponte, Gregory W., "PYY-mediated fatty acid induced intestinal differentiation", Peptides 23, pp. 367-376 (2002).

Asakawa, A., et al., "Mouse pancreatic polypeptide modulates food intake, while not influencing anxiety in mice," Peptides, 20:1445-1448 (1999).

Bader, R., et al., "Key Motif to Gain Selectivity at the Neuropeptide $Y_5$-Receptor: Structure and Dynamics of Micelle-Bound [$Ala^{31}$, $Pro^{32}$]-NPY," Biochemistry, 41(25):8031-8042 (2002).

Balasubramaniam, A., "Neuropeptide Y Family of Hormones: Receptor Subtypes and Antagonists," Peptides, 18(3):445-457 (1997).

Balasubramaniam, A., et al., "Bis(31/31'){[$Cys^{31}$, $Nva^{34}$]NPY(27-36)-$NH_2$}: a neuropeptide Y (NPY)$Y_5$ receptor selective agonist with a latent stimulatory effect on food intake in rats," Peptides, 23(8):1485-1490 (2002).

Balasubramaniam, A., et al., "Structure-Activity Studies Including a (psi)(CH2-NH) Scan of Peptide YY (PYY) Active Site, PYY(22-36), for Interaction with Rat Intestinal PYY Receptors: Development of Analogues with Potent in Vivo Activity in the Intestine," J. Med. Chem., 43:3420-3427 (2000).

Balasubramaniam, A., et al., "Structure-activity studies of peptide YY(22-36): N-α-Ac[$Phe^{27}$]PYY(22-36), a potent antisecretory peptide in rat jejunum," Peptides, 14(5):1011-1016 (1993).

Balasubramaniam, A., et al., "Syntheses and Receptor Affinities of Partial Sequences of Peptide YY (PYY)," Peptide Research, 1(1):32-35 (1988).

Balasubramaniam, A., et al., "Synthesis of neuropeptide Y," Int J Pept Protein Res., 29(1):78-83 (1987).

Barany Francis, "Genetic Disease Detection and DNA Amplification Using Cloned Thermostable Ligase," Proc. Natl. Acad. Sci. SA 88:189-193 (1991).

Batterham, R.L., et al., "Gut hormone PYY3-36 physiologically inhibits food intake," Nature, 418:650-654 (2002).

Batterham, R.L., et al., "Inhibition of Food Intake in Obese Subjects by Peptide YY3-36," N Engl J Med, 349(10):941-948 (2003).

Beck, A., et al., "Highly potent and small neuropeptide Y agonist obtained by linking NPY 1-4 via spacer to α-helical NPY 25-36," FEBS Lett., 244(1):119-122 (1989).

Beck-Sickinger, A. G., et al., "Cyclopeptide analogs for characterization of the neuropeptide $YY_2$-receptor," J Recept Res., 13(1-4):215-228 (1993).

Berge et al., "Pharmaceutical Salts," Journal of Pharmaceutical Sciences, 66(1):1-19 (1977).

Berglund, M. M., et al., "Recent Developments in Our Understanding of the Physiological Role of PP-Fold Peptide Receptor Subtypes," Exp Biol Med (Maywood), 228(3):217-244 (2003).

Birdsall and Hulme, "Muscarinic Receptor Subclasses," TIPS, pp: 459-463 (1983).

Bischoff, A. and Michel, M. C., "Emerging functions for neuropeptide $Y_5$ receptors," Trends Pharmacol Sci., 20(3):104-106 (1999).

Bonaz, B., et al., "Peripheral peptide YY induces c-fos-like immunoreactivity in the rat brain," Neuroscience Letters, 163:77-80 (1993).

Boublik, J. H., et al., "Synthesis and hypertensive activity of neuropeptide Y fragments and analogues with modified N- or C-termini or D-substitutions," J Med Chem, 32(3):597-601 (1989).

Bousquet-Melou, et al., "Control of lipolysis in intra-abdominal fat cells of nonhuman primates: comparison with humans", Journal of Lipid Research, 36, pp. 451-461 (1995).

Braesch et al., "Immune Response of Diabetic Patients against Transplanted Porcine Fetal Islet Cells.," "Transplantation Proceedings 24(2):679-680 (1992).

Brown, K.K., et al., "A Novel N-Aryl Tyrosine Activator of Peroxisome Proliferator-Activated Receptor-Y Reverses the Diabetic Phenotype of the Zucker Diabetic Fatty Rat," Diabetes, 48:1415-1424 (1999).

Cabrele, C. and Beck-Sickinger, A. G., "Molecular characterization of the ligand-receptor interaction of the neuropeptide Y family," J Pept Sci., 6(3):97-122 (2000).

Cabrele, C., et al., "$Ala^{31}$-$Aib^{32}$: Identification of the key motif for high affinity and selectivity of neuropeptide Y at the $Y_5$-receptor," Biochemistry, 41(25):8043-8049 (2002).

Cabrele, C., et al., "The first selective agonist for the neuropeptide $YY_5$ receptor increases food intake in rats," J Biol Chem., 275(46): 36043-36048 (2000).

Cabrele, C., et al., "Y-receptor affinity modulation by the design of pancreatic polypeptide/neuropeptide Y chimera led to $Y_5$-receptor ligands with picomolar affinity," Peptides, 22(3):365-378 (2001).

Campfield, L.A., et al., "Recombinant Mouse OB Protein: Evidence for a Peripheral Signal Linking Adiposity and Central Neural Networks," Science, 269(5223):546-549 (1995).

Chen, C., et al., "PYY and NPY: control of gastric motility via action on Y1 and Y2 receptors in the DVC", Neurogastroenterol. Mot., 9: 109-116 (1997).

Chen, C.H. and Rogers, R.C., "Central inhibitory action of peptide YY on gastric motility in rats," Am. J. Physiol., 269:R787-R792 (1995).

Chen, C.H., et al., "Intracisternal injection of peptide YY inhibits gastric emptying in rats," Regulatory Peptides, 61:95-98 (1996).

Chen, M., et al., "Sensitive Radioimmunoassay for Measurement of Circulating Peptide YY", Gastroenterology, 87: 1332-8 (1984).

Chen, Z., et al., "Ser$^{13}$-phosphorylated PYY from porcine intestine with a potent biological activity," FEBS Lett., 492(1-2):119-122 (2001).

Clark, J.T., et al., "Neuropeptide Y (NPY)-induced feeding behavior in female rats: comparison with human NPY ([Met17]NPY), NPY analog ([norLeu4]NPY) and peptide YY," Regulatory Peptides, 17:31-39 (1987).

Clark, J.T., et al., "Neuropeptide Y and Human Pancreatic Polypeptide Stimulate Feeding Behavior in Rats," Endocrinology, 115(1):427-429 (1984).

Conlon, J. M., "The origin and evolution of peptide YY (PYY) and pancreatic polypeptide (PP)," Peptides, 23(2):269-278 (2002).

Cook et al., "Intracellular ATP Directly Blocks K+ channels in Pancreatic B-Cells," Nature 311:271-273 (1984).

Corp, E. S., et al., "Effect of fourth ventricular neuropeptide Y and peptide YY on ingestive and other behaviors", The American Physiological Society, 317-323 (1990).

Corp, E. S., et al., "Feeding after fourth ventricular administration of neuropeptide Y receptor agonists in rats," Peptides, 22(3):493-499 (2001).

Coruzzi et al., "gastric Antisecretory Activity of Telensepine, a New $M_1$ - Selective Muscarinic Antagonist: Comparison with Pirensepine," Arch. Int. Pharmacodyn 302:232-241 (1989).

Cotton et al., "Reactivity of Cytosine and Thymine in Single-Base-pari Mismatches with Hydroxylamine and Osmium Tetroxide and its Application to the Study of Mutations," Proc Natl. Acad. Sci. USA 85:4397-4401 (1988).

Cox et al., "The Effects of Neuropeptide Y and its Fragments upon Basal and Electrically Stimulated Ion Secretion in Rat ejunum Mucosa," Br. J. Pharmacol. 101:247-252 (1990).

Cox, H. M., et al., "Structure-activity relationships with neuropeptide Y analogues: a comparison of human $Y_1$-, $Y_2$- and rat $Y_2$-like systems," Regulatory Peptides, 75-76:3-8 (1998).

Dea et al., "Molecular Heterogeneity of Human Motilinlike Immunoreactivity Explained by the Processing of Prepromotilin," Gastroenterology 96:695-703 (1989).

Deng, X., et al., "PYY Potently Inhibits Pancreatic Exocrine Secretion Mediated Through CCK-Secretin-Stimulated Pathways but Not 2-DG-Stimulated Pathways in Awake Rats," Digestive Diseases and Sciences, 46(1):156-165 (2001).

Dos Santos Medeiros, M., et al., "Processing and Metabolism of Peptide-YY: Pivotal Roles of Dipeptidylpeptidase-IV, Aminopeptidase-P, and Endopeptidase-24.11", Endocrinology, 134: 2088-2094 (1994).

Dumont, Y., et al., "Evaluation of truncated neuropeptide Y analogues with modifications of the tyrosine residue in position 1 on $Y_1$, $Y_2$ and $Y_3$ receptor sub-types," Eur J Pharmacology, 238(1):37-45 (1993).

Eberlein, G., et al, "A New Molecular Form of PYY: Structural Characterization of Human PYY (3-36) and PYY (1-36)", Peptides, 10: 797-803 (1989).

Eto, B., et al., "Effects of Peptide YY and Its Analogues on Chloride Ion Secretion in Fed and Fasted Rat Jejunum," Peptides, 16(8):1403-1409 (1995).

Fackelmann, K., "Gut hormone could curb urge to overeat", USA Today.com (Aug. 7, 2002).

Feinstein, R. D., et al., "Structural Requirements for Neuropeptide Y$^{18-36}$-Evoked Hypotension: A Systematic Study," J Med Chem., 35(15):2836-2843 (1992).

Ferber et al., "GLUT-2 Gene Transfer into Insulinoma Cells Confers Both Low and High Affinity Glucose-Stimulated Insulin Release," The Journal of Biological Chemistry 269(15):11523-11529 (1994).

Fournier, A., et al., "Conformational and Biological Studies of Neuropeptide Y Analogs Containing Structural Alterations," Mol Pharmacol., 45(1):93-101 (1994).

Garlicki, J., et al., "Cholecystokinin receptors and vagal nerves in control of food intake in rats," Am. J. Physiol., 258:E40-E45 (1990).

Gedulin, B.R., et al., "Assessment of Gastric Emptying from Appearance in Plasma of 3H from Gavaged [3-3H] Glucose in Conscious Rats: Effects of Amylin," Gastroenterological, Abstract, vol. 108, No. 4 (Apr. 1995).

Gehlert, "Multiple Receptors for the Pancreatic Polypeptide (PP-Fold) Family: Physiological Implications (44263)," P.S.E.B.M. 218:7-22 (1998).

Gehlert, Donald R., "Multiple Receptors for the Pancreatic Polypeptide (PP-Fold) Family: Physiological Implications (44263)," Lilly Neuroscience, pp. 7-22 (1998).

Gibbs et al., "Detection of Single DNA base Differences by Competitive Oligonucleotide Priming," Nucleic Acids Research 17(7):2437-2448 (1989).

Gobbi, M., et al, "Autoradiographic Reevaluation of the Binding Properties of $^{125}$I- [Leu$^{31}$,Pro$^{34}$]Peptide YY and $^{125}$I-Peptide YY$_{3-36}$ to neuropeptide Y Receptor Subtypes in Rat Forebrain," J Neurochem., 72(4):1663-1670 (1999).

Gold et al., "Effect of Age on Proinsulin and Insulin Secretory Patterns in Isolated Rat Islets," Diabetes 30:77-82 (1991).

Gomez, G., et al., "Intestinal peptide YY: ontogeny of gene expression in rat bowel and trophic actions on rat and mouse bowel," Am. J. Physiol., 268:G71-G81 (1995).

Gordon, E. A., et al., "Centrally truncated neuropeptide Y analog acts as an agonist for Y1 receptors on SK-N-MC cells," Neuroscience Letters, 119(2):187-190 (1990).

Grandt, D., et al, "Two Molecular Forms of Peptide YY (PYY) are Abundant in Human Blood: Characterization of a Radioimmunoassay Recognizing PYY 1-36 and PYY 3-36", Regulatory Peptides, 51: 151-159 (1994).

Grandt, D., et al., "Novel Generation of Hormone Receptor Specificity By Amino Terminal Processing of Peptide YY", Biochemical and Biophysical Research Communications, 186: 3:299-1306 (1992).

Greeley et al., "Peptide YY Antagonizes β-adrenergic-stimulated Release of Insulin in Dogs," Am. J. Physiol. 254:E513-E517 (1988).

Greeley, G.H., et al., "Inhibition of Gastric Acid Secretion by Peptide YY is Independent of Gastric Somatostatin Release in the Rat (42814)," Proceedings of the Society for Experimental Biology and Medicine, 189:325-328 (1988).

Groth et al., "Evidence of Xenograft Function in a Diabetic Patient Grafted with Porcine Fetal Pancreas," Transplantation Proceedings 24(3):972-973 (1992).

Grouzmann, E., et al, "Expression and Regulation of Neuropeptide Y in a Rat Insulinoma Cell Line", Endocrinology, Abstract 519B (1993).

Grundemar, L., et al., "Ligand binding and functional effects of systematic double D-amino acid residue substituted neuropeptide Y analogs on Y1 and Y2 receptor types," Regulatory Peptides, 62(2-3):131-136 (1996).

Guan, et al., "Peptide-YY, a New Partner in the Negative Feedback Control of Pancreatic Secretion," Endocrinology, 128(2):911-916 (1991).

Gue, M., et al., "Reversal by NPY, PYY and 3-36 molecular forms of NPY and PYY of intracisternal CRF-induced inhibition of gastric acid secretion in rats," British Journal of Pharmacology, 118:237-242 (1996).

Hagan, M.M. and Moss, D.E., "Effect of Naloxone and Antidepressants on Hyperphagia Produced by Peptide YY," Pharmacology Biochemistry and Behavior, 45:941-944 (1993).

Halaas, J.L., et al., "Weight-Reducing Effects of the Plasma Protein Encoded by the Obese Gene," Science, 269(5223):543-546 (1995).

Halatchev, I. G., et al., "Peptide YY$_{3-36}$ Inhibits Food Intake in Mice through a Melanocortin-4 Receptor-Independent Mechanism," Endocrinology, 145(6):2585-2590 (2004).

Haynes, J.M., et al., "Neuropeptide Y (NPY) and peptide YY (PYY) effects in the epididymis of the guinea-pig: evidence of a pre-junctional PYY-selective receptor," British Journal of Pharmacology, 122:1530-1536 (1997).

Henry, M., et al., "Energy Metabolic Profile of Mice after Chronic Activation of Central NPY Y1, Y2, or Y5 Receptors," Obesity Research 13(1):36-47 (2005).

Hoentjen, F., et al., "Role of Circulating Peptide YY in the Inhibition of Gastric Acid Secretion by Dietary Fat in Humans," Scand J Gastroenterol, 35:166-171 (2000).

Holiday et al., "The Functional Investigation of a Human Adenocarcimona Cell Line, Stably Transfected with the Neuropeptide $YY_1$ Receptor," British Journal of Pharmacology 119:321-329 (1996).

Hsu et al., "Detection of DNA Point Mutations with DNA Mismatch Repair Enzymes," Carcinogenesis 15(8):1657-1662 (1994).

Hu, Y., et al., "Identification of a Novel Hypothalamic Neuropeptide Y Receptor Associated with Feeding Behavior," J Biol Chem., 271(42):26315-26319 (1996).

Hughes et al., "Engineering of Glucose-Stimulated Insulin Secretion and Biosynthesis in Non-Islet Cells," Proc. Natl. Acad. Sci. USA 89:688-692 (1992).

Inui, A., "Neuropeptide Y feeding receptors: are multiple subtypes involved?" Trends Pharmacol Sci., 20(2):43-46 (1999).

Iyengar, S., et al., "Characterization of Neuropeptide Y-Induced Feeding in Mice: Do Y1-Y6 Receptor Subtypes Mediate Feeding?," JPET, 289(2):1031-1040 (1999).

Jackerott et al., "Immunocytochemical Localization of the NPY/PYY Y1 Receptor in the Developing Pancreas," Endocrinology 138(11):3013-5018 (1997).

Jackerott et al., "PYY in Developing Murine Islet Cells: Comparisons to Development of Islet Hormones, NPY, and BrdU Incorporation," Teh Journal of Histochemistry adn Cytochemistry 44(8):809-817 (1996).

Johnson et al., "Underexpression of β Cell High $K_m$ Glucose Transporters in Noninsulin-Dependent Diabetes," Science 250:546-549 (1990).

Jones et al., "Protein Kinases, Proetin Phosphorylation, and the Regulation of Insulin Secretion from Pancreatic β-Cells," Endocrine Reviews 19(4):429-461 (1998).

Kanatani, A., et al., "L-152,804: Orally active and selective neuropeptide Y Y5 receptor antagonist," Biochemical Biophysical Research Communications, 272(1):169-173 (2000).

Kanatani, A., et al., "Role of the Y1 Receptor in the Regulation of Neuropeptide Y-Mediated Feeding: Comparison of Wild-Type, Y1 Receptor-Deficient, and Y5 Receptor-Deficient Mice," Endocrinology, 141(3):1011-1016 (2000).

Kanatani, A., et al., "The novel neuropeptide $YY_1$ receptor antagonist J-104870: a potent feeding suppressant with oral bioavailability," Biochem Biophys Res Commun., 266(1):88-91 (1999).

Karlsson et al., "A role for islet peptide YY in the regulation of insulin secretion", Acta Physiol. Scand, 157: 305-306 (1996).

Kato, K., et al., "CGRP Antagonists Enhance Gastric Acid Secretion in 2-h Pylorus-Ligated Rats," Peptides, 16(7):1257-1262 (1995).

Kawakubo, K., et al., "Intracisternal PYY inhibits gastric lesions induced by ethanol in rats: role of PYY-preferring receptors?," Brain Research, 854:30-34 (2000).

Keire, D. A., et al., "Primary structures of PYY, [Pro$^{34}$] PYY, and PYY-(3-36) confer different conformations and receptor selectivity," Am J Physiol. Gastrointest Liver Physiol, 279(1):G126-G131 (2000).

Keire, D. A., et al., "Solution structure of monomeric peptide YY supports the functional significance of the PP-fold," Biochemistry, 39(32):9935-9942 (2000).

Keire, D. A., et al., "Structure and receptor binding of PYY analogs," Peptides, 23(2):305-321 (2002).

Kimmel, J.R., et al., "Isolation and Characterization of Chicken Insulin," Endocrinology, 83:1323-1330 (1968).

Kirby, D. A., et al., "Neuropeptide Y: $Y_1$ and $Y_2$ affinities of the complete series of analogues with single D-residue substitutions," J Med Chem., 36(24):3802-3808 (1993).

Kirby, D. A., et al., "$Y_1$ and $Y_2$ receptor selective neuropeptide Y analogues: evidence for a $Y_1$ receptor subclass," J Med Chem., 38(22):4579-4586 (1995).

Kopelman, P.G., "Obesity as a medical problem," Nature, 404:635-643 (2000).

Korsgren et al., "Large-Scale Production of Fetal Porcine Pancreatic sletlike Cell Clusters," Transplantation 45:509-514 (1998).

Krasinski et al., "Isolation, Characterization, adn Development Expression of the Rat Peptide-YY Gene," Mol. Endo. 5(3):433-440 (1991).

Krstenansky, J. L., et al., "C-terminal modifications of neuropeptide Y and its analogs leading to selectivity for the mouse brain receptor over the porcine spleen receptor," Neuropeptides, 17(3):117-120 (1990).

Krstenansky, J. L., et al., "Centrally truncated and stabilized porcine neuropeptide Y analogs: design, synthesis, and mouse brain receptor binding," Proc Natl Acad Sci U S A., 86(12):4377-4381 (1989).

Kushi, A., et al., "Obesity and mild hyperinsulinemia found in neuropeptide Y-Y1 receptor-deficient mice," Proc. Natl. Acad. Sci. USA, 95:15659-15664 (1998).

Lacy et al., "Maintenance of Normoglycemia in Diabetic Mice by Subcutaneous Xenografts of Encapsulated Islets," Science 254:1782-1784 (1991).

Landegren et al., "A Ligase-Mediated Gene Detection Technique," Science 241:1077-1080 (1988).

Leban, J. J., et al., "Novel modified carboxy terminal fragments of neuropeptide Y with high affinity for $Y_2$-type receptors and potent functional antagonism at a $Y_1$ -type receptor," J Med Chem., 38(7):1150-1157 (1995).

Leibowitz, S.F., et al, "Analysis of Neuropeptide Y-Induced Feeding: Dissociation of Y(1) and Y(2) Receptor Effects on Natural Meal Patterns", Peptides, 12: 1251-1260 (1991).

Liu et al., "Persistent Reversal of Diabetes by Transplantation of Fetal Pig Proislets into Nude Mice," Diabetes 40:858-866 (1991).

Liu, C. D., et al., "Synthetic peptide YY analog binds to a cell membrane receptor and delivers fluorescent dye to pancreatic cancer cells," J Gastrointest Surg., 5(2):147-152 (2001).

Lloyd, K.C.K., et al., "Inhibitory effect of PYY on vagally stimulated acid secretion is mediated predominantly by Y1 receptors," Am. J. Physiol., 270:G123-G127 (1996).

Lluis et al, "Peptide YY Inhibits Pancreatic Secretion by Inhibiting Cholecystokinin Release in the Dog," Gastroenterology 94137-144 (1988).

Lundberg et al, "Localization of Peptide YY (PYY) in Gastrointestinal Endocrine Cells and Effects on Intestinal Blood Flow and Motility," Proc. Natl. Acad. Sci. USA 79:4471-4475 (1982).

Lundell, I., et al., "Cloning of a human receptor of the NPY receptor family with high affinity for pancreatic polypeptide and peptide YY," J Biol Chem., 270(49):29123-29128 (1995).

Malaisse-Lagae, F., et al., "Pancreatic polypeptide: A possible role in the regulation of food intake in the mouse," Experientia 33, 915-917 (1977).

Marsh, D.J., et al., "Role of the Y5 neuropeptide Y receptor in feeding and obesity," Nature Medicine, 4(6):718-721 (1998).

Martin, N. M., et al., "Pre-obese and obese agouti mice are sensitive to the anorectic effects of peptide $YY_{3-36}$ but resistant to ghrelin," Int J Obes Relat Metab Disord., 28(7):886-893 (2004).

Mashiko, S., et al., "Characterization of neuropeptide Y (NPY) Y5 receptor-mediated obesity in mice: chronic intracerebroventricular infusion of D-Trp$^{34}$NPY," Endocrinology, 144(5):1793-1801 (2003).

Maxam et al., "A New Method for Sequencing DNA," Proc. Natl Acad. Sci. USA 74(2):560-564 (1977).

Michel, M.C., et al., "XVI. International Union of Pharmacology Recommendations for the Nomenclature of Neuropeptide Y, Peptide YY, and Pancreatic Polypeptide Receptors," Pharmacological Reviews, 50(1):143-150 (1998).

Morley et al., "An Investigation of Tolerance to the Action of Leptogenic and Anorexigenic Drugs in Mice", Life Sciences, vol. 41, pp. 2157-2165 (1987).

Morley, J. E., "An Approach to the Development of Drugs for Appetite Disorders", Neuropsychobiology, 21: 22-30 (1989).

Morley, J. E., et al., "An Investigation of Tolerance to the Actions of Leptogenic and Anorexigenic Drugs in Mice", Life Sciences, 41: 2157-2165 (1987).

Morley, J.E., et al., "Modulation of food intake by peripherally administered amylin," Am. J. Physiol., 267:R178-R184 (1994).

Morley, J.E., et al., "Peptide YY (PYY), a potent orexigenic agent," Brain Research, 341:200-203 (1985).

Mulder et al., "Expression of Non-Classical Islet Hormone-Like Peptides During the Embryonic Development of the Pancreas," Microscopy Research and Technique 43:313-321 (1998).

Mullins, D., et al., "Identification of potent and selective neuropeptide Y $Y_1$ receptor agonists with orexigenic activity in vivo," Molecular Pharmacology, 60(3):534-540 (2001).

Munson, P.J. and Rodbard, D., "LIGAND: A Versatile Computerized Approach for Characterization of Ligan-Binding Systems," Analytical Biochemistry, 107:220-239 (1980).

Murakami, Y., et al., "1,3-Disubstituted benzazepines as novel, potent, selective neuropeptide Y Y1 receptor antagonists," J Med Chem., 42(14):2621-2632 (1999).

Murase, S., et al., "Acylation of the α-amino group in neuropeptide Y(12-36) increases binding affinity for the $Y_2$ receptor," J Biochem (Tokyo), 119(1):37-41 (1996).

Myers et al., Detection of Single Base Substitutions by Ribonuclease Cleavage at Mismatches in RNA: DNA Duplexes Science 230:1242-1245 (1985).

Myers et al., "Detection of Single Base Substitutions in Total Genomic DNA," Nature 313:495-498 (1985).

Naeve et al., "Accuracy of Automated DNA Sequencing: A Multi-Laboratory Comparison of Sequencing Results," Biotechniques 19(3):448-453 (1995).

Nakagawa et al., "UV and Skin Cancer: Specificp53 Gene Mutation in Normal Skin as a Biologically Relevant Exposure Measurement," Proc. Natl. Acad. Sci. USA 91:360-364 (1994).

Nakajima, M., et al., "Effects of Pancreatic Polypeptide Family Peptides on Feeding and Learning Behavior in Mice," The Journal of Pharmacology and Experimental Therapeutics, 268(2):1010-1014 (1994).

Naslund, E., et al., "Energy intake and appetite are suppressed by glucagon-like peptide-1 (GLP-1) in obese men," International Journal of Obesity, 23:304-311 (1999).

Nieuwenhuizen et al., "Mechanism Underlying the Insulinostatic Effect of Peptide YY in Mouse Pancreatic Islets," Diabetologia 37:871-878 (1994).

Odagiri et al., "Function of the Human Insulin Promoter in Primary Cultured Islet Cells," The Journal of Biological Chemistry 271(4):1909-1915 (1996).

Okada, S., et al, "Peripherally Not Centrally Administered Peptide YY (PYY) Decreases High Fat Diet Intake", Endocrinology, Abstract 520B (1993).

On-Line Medical Dictionary. Dept. of Oncology, University of Newcastle upon Tyne. The CancerWeb Project Copyright 1997-2004.

Orita et al, "Detection of Polymorphisms of Human DNA by Gel Electrophoresis as Single-Strand Conformation Polymorphisms," Proc. Natl. Acad. Sci. USA 86:2766-2770 (1989).

Otonkoski et al., "Maturation of Insulin Response to Glucose During Human Fetal and Neonatal Development," Diabetes 37:286-291 (1998).

Pappas et al., "Peptide YY Inhibits Meal-stimulated Pancreatic and Gastric Secretion," Am. J. Physiol. 248:G118-G123 (1985).

Pappas, T.N., et al., "Peptide YY Release by Fatty Acids is Sufficient to Inhibit Gastric Emptying in Dogs," Gastroenterology, 91:1386-9 (1986).

Parker, E. M., et al., "[D-Trp$^{34}$] neuropeptide Y is a potent and selective neuropeptide Y $Y_5$ receptor agonist with dramatic effects on food intake," Peptides, 21(3):393-399 (2000).

Parker, E. M., et al., "GR231118 (1229U91) and other analogues of the C-terminus of neuropeptide Y are potent neuropeptide Y $Y_1$ receptor antagonists and neuropeptide Y $Y_4$ receptor agonists," Eur J Pharmacol., 349(1):97-105 (1998).

Parker, S. L. and Parker, M. S., "FMRFamides exert a unique modulation of rodent pancreatic polypeptide sensitive neuropeptide Y (NPY) receptors," Can J Physiol Pharmacol., 78(2):150-161 (2000).

Pelleymounter, M.A., et al., "Effects of the Obese Gene Product on Body Weight Regulation in Ob-Ob Mice," Science, 269(5223):540-543 (1995).

Pi-Sunyer, F. X., The Medical Risks of Obesity, Obesity Surgery, 12, pp. 6S-11S (2002).

Potter, E. K., et al., "A novel neuropeptide Y analog, N-acetyl [Leu$^{28}$,Leu$^{31}$]neuropeptide Y-(24-36), with functional specificity for the presynaptic ($Y_2$) receptor," Eur J Pharmacol., 267(3):253-262 (1994).

Randle, Philip J., "Regulatory Interactions between Lipids and Carbohydrates: The Glucose Fatty Acid Cycle After 35 Years", Diabetes/Metabolism Review, vol. 14, pp. 263-283 (1998).

Renshaw, D. and Batterham, R. L., "Peptide YY: A Potential Therapy for Obesity," Curr Drug Targets, 6(2):171-179 (2005).

Rhodes et al., "Newly Synthesized Proinsulin/Insulin and Stored Insulin are Released from Pancreatic B Cells Predominantly via a Regulated, Rather than a Constitutive Pathway," Journal of Cell Biology 105:145-153 (1987).

Rissanen, A., et al., "Risk of disability and mortality due to overweight in a Finnish population," Br Med J, 301:835-837 (1990).

Rist, B., et al., "Modified, cyclic dodecapeptide analog of neuropeptide Y is the smallest full agonist at the human $Y_2$ receptor," FEBS Lett., 394(2):169-173 (1996).

Rist, B., et al., "The bioactive conformation of neuropeptide Y analogues at the human $Y_2$-receptor," Eur J Biochem., 247(3):1019-1028 (1997).

Robbins et al., "The Endocrine Pancreas," Pathologic Basis of Disease, 3rd Ed. VB. Sounders Company, Philadelphia pp. 972-990 (1984).

Saiki et al., "Analysis of Enzymatically Amplified β-Globin and HLA-DQα DNA with Allele-specific Oligonucleotide probes," Nature 324:163-166 (1986).

Saiki et al., "Genetic Analysis of Amplified DNA wit Immobilized Sequence-Specific Oligonucleotide Probes," Proc. Natl. Acad. Sci. USA 86:6230-6234 (1989).

Saleeba et al., "Chemical Cleavage of Mismatch to Detect Mutations," Methods in Enzymology 217:286-295 (1993).

Sander et al., "A Novel Glucose-Responsive Element in the Human Insulin Gene Functions Uniquely in Primary Cultured Islets," Proc. Natl. Acad. Sci. USA 95:11572-11577 (1998).

Sanger et al., "DNA Sequencing with Chain-terminating Inhibitors," Proc. Natl. Acad. Sci. USA 74(12):5463-5467 (1977).

Sato, N., et al., "Design and Synthesis of the Potent, Orally Available, Brain-Penetrable Arylpyrazole Class of Neuropeptide Y5 Receptor Antagonists," J Med Chem., 46(5):666-669 (2003).

Savage, A.P., et al., "Effects of peptide YY (PYY) on mouth to caecum intestinal transit time and on the rate of gastric emptying in healthy volunteers," Gut, 28:166-170 (1987).

Scheen, "Drug Treatment of Non-insulin-dependent Diabetes Mellitus in the 1990s", Drugs 54(3):355-368 (1997).

Schuit, "Factor Determining the Glucose Sensitivity and Glucose Responsiveness of Pancreatic Beta Cells," Horm. Res. 46:99-106 (1996).

Schwartz, M.W., et al., "Central nervous system control of food intake," Nature, 404:661-671 (2000).

Servin, A. L., et al., "Peptide-YY and Neuropeptide-Y Inhibit Vasoactive Intestinal Peptide-Stimulated Adenosine 3',5'-Monophosphate Production in Rat Small Intestine: Structural Requirements of Peptides for Interacting with Peptide-YY-Preferring Receptors," Endocrinology, 124(2):692-700 (1989).

Shan, L., et al., "Structural Basis for Gluten Intolerance in Celiac Sprue," Science, 297(5590):2275-2279 (2002).

Sheikh, S. P., "Neuropeptide Y and peptide YY: major modulators of gastrointestinal blood flow and function," Am J Physiol., 261(5 Pt 1):G701-G715 (1991).

Silva, A. P., et al., "Neuropeptide Y and its receptors as potential therapeutic drug targets," Clinica Chimica Acta, 326(1-2):3-25 (2002).

Simeonovic et al., "The Isolation and Transplantation of Foetal Mouse Proislets," Aust. J. Exp. Biol. Med. Sci. 60(part 4):383-390 (1982).

Slack, et al., "Developmental biology of the pancreas", Development, 121: 1569-1580 (1995).

Small, C. J., et al., "Peptide analogue studies of the hypothalamic neuropeptide Y receptor mediating pituitary adrenocorticotrophic hormone release," Proc Natl Acad Sci U S A., 94(21):11686-11691 (1997).

Soll, R. M., et al., "Novel analogues of neuropeptide Y with a preference for the $Y_1$-receptor," Eur J Biochem., 268(10):2828-2837 (2001).

St-Onge, et al., "Physiological Effects of Medium-Chain Triglycerides: Potential Agents in the Prevention of Obesity", American Society for Nutritional Sciences, pp. 329-332 (2002).

Stanley, B.G., et al., "Paraventribular Nucleus Injections of Peptide YY and Neuropeptide Y Preferentially Enhance Carbohydrate Ingestion," Peptides, 6:1205-1211 (1985).

Sullivan et al., "Biohybrid Artificial Pancreas: Long-term Implantation Studies in Diabetic, Pancreatectomized Dogs," Science 252:718-721 (1991).

Surwit, R.S., et al., "Differential Effects of Fat and Sucrose on the Development of Obesity and Diabetes in C57BL/6J and A/J Mice," Metabolism, 44(5):645-651 (1995).

Suzuki et al., "Inhibition of Interdigestive Contractile Activity in the Stomach by Peptide YY in Heidenhain Pouch Dogs," Gastroenterology 85:114-121 (1983).

Taniguchi, H., et al., "Pharmacological profile of T-0632, a novel potent and selective CCK(a) receptor antagonist, in vivo," European Journal of Pharmacology, 312:227-233 (1996).

Tatemoto, "Isolation and Characterization of Peptide YY (PYY), a Candidate Gut Hormone that Inhibits Pancreatic Exocrine Secretion," Proc. Natl. Acad. Sci. USA 79:2514-2518 (1982).

Tatemoto, K., "Neuropeptide Y: Complete Amino Acid Sequence of the Brain Peptide," Proc. Natl. Acad. Sci. USA, 79:5485-5489 (1982).

Tatemoto, K., et al, "Isolation and Primary Structure of Human Peptide YY", Biochemical and Biophysical Research Communication 157:2: 713-717 (1988).

Tatemoto, K., et al., "Neuropeptide Y-a novel brain peptide with structural similarities to peptide YY and pancreatic polypeptide," Nature, 296:659-660 (1982).

Tatemoto, K., et al., "Synthesis of receptor antagonists of neuropeptide Y," Proc Natl Acad Sci U S A., 89(4):1174-1178 (1992).

Thorens et al., "Reduced Expression of the Liver/beta-cell Glucose Transporter Isoform in Glucose-insensitive Pancreatic beta Cells of Diabetic Rats," Proc. Natl. Acad. Sci. USA 87:6492-6496 (1990).

Thum, A., et al., "Endoproteolysis by isolated membrane peptidases reveal metabolic stability of glucagon-like peptide-1 analogs, exendins-3 and -4," Exp Clin Endocrinol Diabetes, 110(3):113-118 (2002).

Tito et al., "Peptide YY ameliorates cerulein-induced pancreatic injury in the rat", American Journal of Surgery, 165:6, 690-696 (1993).

Totheroh, G., "Science Offers Promising Treatment for an Overweight Nation" CBN News (Sep. 4, 2003).

Towfigh et al., "Peptide YY Exhibits Mitogenic Effect on Pancreatic Ductal Cells While Improving Acute Pancreatitis," *Surgical Forum*, 50:25-27 (1999).

Tschop, M., et al., Physiology: does gut hormone PYY3-36 decrease food intake in rodents? Nature. Jul 8, 2004; 430(6996):1 p following 165; discussion 2 p following 165.

Tseng, W. W. and Liu, C. D., "Peptide YY and cancer: current findings and potential clinical applications," Peptides, 23(2):389-395 (2002).

Tuch et al., "Release of Proinsulin fom the Human Fetal β Cell," Journal of Endocrinology 132:159-167 (1992).

Turnbull, A. V., et al., "Selective antagonism of the NPY Y5 receptor does not have a major effect on feeding in rats," Diabetes, 51(8):2441-2449 (2002).

Ueno, N., et al., "Decreased Food Intake and Body Weight in Pancreatic Polypeptide-Overexpressing Mice," Gastroenterology, 117:1427-1432 (1999).

Upchurch et al., "Expression of Peptide YY in all Four Islet Cell Types in the Developing Mouse Pancrease Suggests a Common Peptide YY-producing Progenitor," Development 120:245-252 (1994).

Valera et al., "Expression of GLUT-2 Antisense RNA in β Cells of Transgenic Mice Leads to Diabetes," The Journal of Biological Chemistry 269(46):28543-28546 (1994).

Valet, P., "Neuropeptide Y and Peptide YY Inhibit Lipolysis in Human and Dog Fat Cells through a Pertussis Toxin-sensitive G Protein", J. Clin. Invest., 85, pp. 291-295 (1990).

Verchere, C. B., et al, "Major Species Variation in the Expression of Galanin mRNA in Mammalian Celiac Ganglion", Endocrinology, Abstract 517B (1993).

Voisin et al., "Peptide YY receptors in the proximal tubule PKSV-PCT cell line derived from transgenic mice", The Journal of Biological Chemistry, 268: pp. 20547-20554 (1993).

Wahoff et al., "Intraperitoneal Transplantation of Microencapsulated Canine Islet Allografts with Short-term, Low-dose Cyclosporing for Treatment of Pancreatectomy-induced Diabetes in Dogs," Transplantation Proceedings 26(2):804 (1994).

Walker, M. W., et al., "A structure-activity analysis of the cloned rat and human Y4 receptors for pancreatic polypeptide," Peptides, 18(4):609-612 (1997).

Walker, M. W., et al., "Neuropeptide Y modulates neurotransmitter release and $Ca^{2+}$ currents in rat sensory neurons," J Neurosci., 8(7):2438-2446 (1988).

Wang, Z. L., et al, "Co-Release of Neuropeptide Y With Insulin Following Dexamethasone", Endocrinology, Abstract 518B (1993).

Weinberg, D. H., et al., "Cloning and expression of a novel neuropeptide Y receptor," J Biol Chem., 271(28):16435-16438 (1996).

Wells, "Additivity of Mutational Effects in Proteins," *Biochemistry*, 29:8509-8517 (1990).

Widdowson, P.S., et al., "Distribution of [Leu31,Pro34]NPY-sensitive, BIBP3226-insensitive [125I]PYY(3-36) binding sites in rat brain: possible relationship to Y5 NPY receptors," Brain Research, 778:242-250 (1997).

Wilding, J. P., "Neuropeptides and appetite control," Diabet Med., 19(8):619-627 (2002).

Wiley, J.W., et al., "Mechanism of Action of Peptide YY to Inhibit Gastric Motility," Gastroenterology, 100:865-872 (1991).

Wilson et al., "Role of $CD4^+$ T-Lymphocytes in Rejection by Mice of Fetal Pig Proislet Xenografts," Diabetes 38(Suppl. 1):217-219 (1989).

Yang, H. and Tache, Y., "PYY in brain stem nuclei induces vagal stimulation of gastric acid secretion in rats," Am. J. Physiol., 268:G943-G948 (1995).

Yang, H., et al., "PYY-preferring receptor in the dorsal vagal complex and its involvement in PYY stimulation of gastric acid secretion in rats," British Journal of Pharmacology, 123:1549-1554 (1998).

Yoshinaga, K., et al., "Structural requirements of peptide YY for biological activity at enteric sites," Am. J. Physiol., 263:G695-G701 (1992).

Yoshinaga, K., et al., Structural requirements of peptide YY for biological activity at enteric sites, Am. J. Physiol., 263:G695-G701 (1992).

Young, AA, et al., "Genetically Obese (OB/OB) Mice Are More Sensitive To Amylin and Endotoxin Induced Suppression of Food Intake", Amylin Pharmaceuticals Inc., Program & Abstracts, vol. 1: (Jun. 12 & 13, 1996).

Zai, H., et al., "Effect of peptide YY on gastric motor and secretory activity in vagally innervated and denervated corpus pouch dogs," Regulatory Peptides, 61:181-188 (1996).

Bard et al., Cloning and Functional Expression of a Human Y4 subtype receptor for pancreatic polypeptide, neuropeptide y, and peptide YY. J. Biological Chemistry, 270:45;26762-26765, 1995.

Brunicardi et al., Pancreatic polypeptide administration improves abnormal glucose metabolism in patients with chronic pancreatitis. Journal of Clinical Endocrinology and Metabolism, vol. 81, No. 10 (1996).

Carter et al., Improved oligonucleotide site-directed mutagenesis using M13 vectors, Nucleic Acids Research, 13:12, 4431-4443, 1985.

Chan and Ferenci, Combinatorial Mutagenesis of the lamB gene: residues 41 through 43, which are conserved in *Escherichia coli* outer membrane proteins, are informationally important in maltoporin structure and function, J. Bacteriology 175:3, 858-865, 1993.

Cotton, R.G. H.; "Current Methods of Mutation Detection", Mutation Research, 285: 125-144, (1993).

Dox, I.G., et al. The Harper Collins Illustrated Medical Dictionary, (Harper Collins Publishers Inc. 1993 New York, NY.)

Freshney, I.R., Culture of Animal Cells, A Manual of Basic Technique. (Alan R. Liss, Inc. 1983, New York, NY).

Gray and Flatt, "Insulin-secreting activity of the traditional antidiabetic plant *Viscum album* (mistletoe)" Journal of Endocrinology (1999) 160, 409-414.

Greeley et al.; "Peptide YY Antagonizes 13-adrenergic-stimulated release of Insulin in Dogs", Am. J. Physiol. 254: E513-E517 (1988).

Kahne et al., "Early phosphorylation events induced by DPIV/CD26-specific inhibitors," Cellular Immunology 189, 60-66, 1998.

Lopelman, P.G., "Obesity as a medical problem," Nature, 404:635-643 (2000).

Ngo et al., Computational Complexity, Protein Structure Prediction and the Levinthal Paradox. The Protein Folding Problem and Tertiary Structure Prediction. 492-495 Birkhauser Boston (1994).

Nonaka et al., "TMC-2A and -2C, Novel Dipeptidyl Peptidase IV inhibitors produced by *Aspergillus oryzae*," Journal of Antibiotics, Aug. 1997, 646-652.

Wiedeman and Trevillyan, "Dipeptidyl peptidase IV inhibitors for the treatment of impaired glucose tolerance and type II diabetes," Current Opinion in Investigational Drugs 2003 4(4):412-420.

Bertrand, G. et al., "Evidence for a Direct Inhibitory Effect of PYY on Insulin Secretion in Rats", Pancreas, vol. 7, No. 5, pp. 595-600, 1992.

Bickel, H. et al., "Neonatal Mass Screening for Metabolic Disorders", Eur J Pediatr 137: 133-139, (1981).

Liu, C. et al., "Adjuvant Hormonal Treatment With Peptide YY or Its Analog Decreases Human Pancreatic Carcinoma Growth", The Americal Journal of Surgery, vol. 171, (1996).

Liu, C. et al., A Novel Synthetic Analog of Peptide YY, BIM-43004, GivenIntraluminally, Is Proabsorptive, Journal of Surgical Research, 59, pp. 80-84, (1995).

Ramo, O. et al., "Neuropeptide Y and Peptide YY Stimulate the Growth of Exocrine Pancreatic Carcinoma Cells", Neuropeptides 15, pp. 101-106, (1990).

Stedman's Medical Dictionary, 25th Edition, 1990, pp. 426-427, Williams & Wilkins, Baltimore, MD.

Edwards et al., "Cardiovascular and pancreatic endocrine responses to glucagen-like peptide-1(7-36)-amide-in the conscious calf," Exp. Physiol. 1997, 82:709-716.

Kraegen et al., "The gastrointestinal stimulus to insulin release," J. Clin. Invest. 49:524-529, (1970).

Wells, "Additivity of mutational effects in proteins," Biochemistry 29:8509-8517 (1990).

Voisin et al. "Peptide YY receptors in the proximal tubule PKSV-PCT cell line derived from transgenic mice," The Journal of Biological Chemistry. vol. 268/27: 20547-20554 (1993).

Slack et al., "Developmental Biology of the pancreas," Development vol. 121 pp. 1569-1580 (1995).

Karlsson et al., "A role for islet peptide YY in the regulation of insulin secretion." Acta Physil. Scand. vol. 157 pp. 305-306 (1996).

Tito et al., "Peptide YY ameliorates cerulein-induced pancreatic injury in the rat." American Journal of Surgery vol. 165/6 pp. 690-696 (1993).

Bischoff, A., et al., "Neuropeptide Y Lowers Blood Glucose in Anaesthetized Rats via a $Y_5$ Receptor Subtype," Endocrinology, 139(6):3018-3021 (1998).

Al-Saffer, A., et al., "Correlation between Peptide YY-Induced Myoelectric Activity and Transit of Small-Intestinal Contents in Rats," Scand J. Gastroenterol, 20(5):577-82 (1985).

Asakawa, A., et al., "Urocortin Reduces Food Intake and Gastric Emptying in Lean and ob/ob Obese Mice," Gastroenterology, 116(6):1287-1292 (1999).

Dumont, Y., et al., "Peptide YY derivatives as selective neuropeptide Y/peptide YY $Y_1$ and $Y_2$ agonists devoided of activity for the $Y_3$ receptor sub-type," Brain Res. Mol. Brain Res., 26(1-2): 320-324 (1994).

El-Salhy, M., "Neuroendocrine peptides of the gastrointestinal tract of an animal model of human type 2 diabetes mellitus," Acta Diabetol., 35(4):194-198 (1998).

Eto, B. et al., "Comparison of the Antisecretory Effect of Endogenous Forms of Peptide YY on Fed and Fasted Rat Jejunum," Peptides, 18(8):1249-1255 (1997).

Eysselein, V.E., et al., Structural Characterization of Canine PYY, Peptides, 11(1): 111-116 (1990).

Grandt, D., et al., "Peptide YY Inhibits Exocrine Pancreatic Secretion in Isolated Perfused Rat Pancreas by Y1 Receptors," Pancreas, 10(2):180-186 (1995).

Guo, Y. et al., "Inhibitory action of peptide YY on gastric acid secretion," Am J Physiol., 253(3 Pt I): G298-302 (1987).

Guo, Y., et al., "Effect of Peptide YY on Cephalic, Gastric, and Intestinal Phases of Gastric Acid Secretion and on the Release of Gastrointestinal Hormones," Gastroenterology, 92(5 Pt 1):1202-1208 (1987).

Kannel, W.B., et al., "Obesity, lipids, and glucose intolerance, The Framingham Study," Am J Clin Nutrition, 32:1238-1245 (1979).

Lluis, F., et al., "Peptide YY Inhibits Nutrient-, Hormonal-, and Vagally-Stimulated Pancreatic Exocrine Secretion," Pancreas, 2(4):454-462 (1987).

Lluis, F., et al., "Peptide YY interacts with secretin and duodenal acidification to inhibit gastric acid secretion," Requl. Pept, 18(3-4):155-163 (1987).

Modan, M., et al., "Hyperinsulinemia, A Link Between Hypertension Obesity and Glucose Intolerance," J Clin Invest, 75(3):809-17 (1985).

Tatemoto, K., et al., "Isolation of two novel candidate hormones using a chemical method for finding naturally occurring polypeptides," Nature, 285(5764):417-418 (1980).

Teyssen, S., et al., "Inhibition of Canine Exocrine Pancreatic Secretion by Peptides YY Is Mediated by PYY-Preferring Y2 Receptors," Pancreas, 13(1):80-88 (1996).

Creutzfeldt et al., "Intensive medical treatment of severe acute pancreatitis," Abstract: World Journal of Surgery, vol. 5(3), pp. 341-350 (1981).

Lochs et al., "Effect of parenteral administration of fat on the glucose and fat metabolism in acute pancreatitis," Abstract: Infusionstherapie and klinische Ernahrung, vol. 9(3), pp. 127-129 (Jun. 1982).

Makimura, H., et al., Obesity Poster Abstract No. 118 "Adrenalectomy stimulates hypothalamic Proopiomelanocortin mRNA but does not correct obesity in diet-induced obese mice". Obesity: New Insights into Pathogenesis and Treatment (J2), Keystone Symposia on Molecular and Cellular Biology, Jan. 21-26, 2003.

Markison S., et al., Obesity Poster Abstract No. 119 "Selective melanin-concentrating hormone receptor antagonists decrease feeding in rodents". Obesity: New Insights into Pathogenesis and Treatment (J2), Keystone Symposia on Molecular and Cellular Biology, Jan. 21-26, 2003.

Mashiko, S., et al., Obesity Poster Abstract No. 120 "Characterization of neuropeptide Y Y5 receptor mediated obesity in mice". Obesity: New Insights into Pathogenesis and Treatment (J2), Keystone Symposia on Molecular and Cellular Biology, Jan. 21-26, 2003.

Reed et al., "Peptide YY reduces the mortality of necrotizing pancreatitis," Abstract: Gastroenterology, vol. 112(4), Suppl. pp. A476. Meeting Inf: Digestive Disease Week and the 97th Annual Meeting of the American Gastroenterological Association, Washington, DC, USA (May 11-14, 1997).

Scatchard, G., "The Attractions of Proteins for Small Molecules and Ions," Annals of the New York Academy of Sciences, vol. 51, pp. 660-672 (1949).

Solomon et al., "The glucose intolerance of acute pancreatitis; hormonal response to arginine," Abstract: Diabetes, vol. 29(1), pp. 22-26 (Jan. 1980).

* cited by examiner

INSULIN CONTENT IN ACTINOMYCIN D TREATED PYY/e21 ISLETS

| AMD (ug/ml) | INSULIN (ng/10 ISLETS) |
|---|---|
| 0 | 213 +/- 6.36 |
| 0.1 | 200 +/- .89 |
| 0.2 | 180 +/- 7.8 |
| 0.5 | 175 +/- 20.9 |
| 1.0 | 210 +/- 7.8 |

```
                           SEQUENCE LISTING

<160> NUMBER OF SEQ ID NOS: 4

<210> SEQ ID NO 1
<211> LENGTH: 108
<212> TYPE: DNA
<213> ORGANISM: Homo sapiens
<220> FEATURE:
<221> NAME/KEY: CDS
<222> LOCATION: (1)..(108)
<223> OTHER INFORMATION:

<400> SEQUENCE: 1 tac ccc atc aaa ccc gag gct ccc ggc gaa gac gcc tcg ccg gag gag        48
Tyr Pro Ile Lys Pro Glu Ala Pro Gly Glu Asp Ala Ser Pro Glu Glu
1               5                   10                  15 ctg aac cgc tac tac gcc tcc ctg cgc cac tac ctc aac ctg gtc acc        96
Leu Asn Arg Tyr Tyr Ala Ser Leu Arg His Tyr Leu Asn Leu Val Thr
            20                  25                  30 cgg cag cgg tac                                                       108
Arg Gln Arg Tyr
        35

<210> SEQ ID NO 2
<211> LENGTH: 36
<212> TYPE: PRT
<213> ORGANISM: Homo sapiens

<400> SEQUENCE: 2

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35
```

```
<210> SEQ ID NO 3
<211> LENGTH: 1650
<212> TYPE: DNA
<213> ORGANISM: Homo sapiens
<220> FEATURE:
<221> NAME/KEY: CDS
<222> LOCATION: (58)..(1380)
<223> OTHER INFORMATION:

<400> SEQUENCE: 3
gggcagaggg cacgggcagg cggacgtcgg ggcgccctcg gggaacgtgc gggcacc        57 atg cgt ccc cac ctg tcg ccg ccg ctg cag cag cta cta ctg ccg gtg     105
Met Arg Pro His Leu Ser Pro Pro Leu Gln Gln Leu Leu Leu Pro Val
1               5                   10                  15 ctg ctc gcc tgc gcc gcg cac tcg act gga gcc ctt ccc cga cta tgt     153
Leu Leu Ala Cys Ala Ala His Ser Thr Gly Ala Leu Pro Arg Leu Cys
            20                  25                  30 gac gtg cta caa gtg ctg tgg gaa gag caa gac cag tgc ctg cag gaa     201
Asp Val Leu Gln Val Leu Trp Glu Glu Gln Asp Gln Cys Leu Gln Glu
        35                  40                  45 ctc tcc aga gag cag aca gga gac ctg ggc acg gag cag cca gtg cca     249
Leu Ser Arg Glu Gln Thr Gly Asp Leu Gly Thr Glu Gln Pro Val Pro
    50                  55                  60 ggt tgt gag ggg atg tgg gac aac ata agc tgc tgg ccc tct tct gtg     297
Gly Cys Glu Gly Met Trp Asp Asn Ile Ser Cys Trp Pro Ser Ser Val
65                  70                  75                  80 ccg ggc cgg atg gtg gag gtg gaa tgc ccg aga ttc ctc cgg atg ctc     345
Pro Gly Arg Met Val Glu Val Glu Cys Pro Arg Phe Leu Arg Met Leu
                85                  90                  95 acc agc aga aat ggt tcc ttg ttc cga aac tgc aca cag gat ggc tgg     393
Thr Ser Arg Asn Gly Ser Leu Phe Arg Asn Cys Thr Gln Asp Gly Trp
            100                 105                 110 tca gaa acc ttc ccc agg cct aat ctg gcc tgt gcg gtt aat gtg aac     441
Ser Glu Thr Phe Pro Arg Pro Asn Leu Ala Cys Ala Val Asn Val Asn
        115                 120                 125 gac tct tcc aac gag aag cgg cac tcc tac ctg ctg aag ctg aaa gtc     489
Asp Ser Ser Asn Glu Lys Arg His Ser Tyr Leu Leu Lys Leu Lys Val
    130                 135                 140 atg tac acc gtg ggc tac agc tcc tcc ctg gtc atg ctc ctg gtc gcc     537
Met Tyr Thr Val Gly Tyr Ser Ser Ser Leu Val Met Leu Leu Val Ala
145                 150                 155                 160 ctt ggc atc ctc tgt gct ttc cgg agg ctc cac tgc act cgc aac tac     585
Leu Gly Ile Leu Cys Ala Phe Arg Arg Leu His Cys Thr Arg Asn Tyr
                165                 170                 175 atc cac atg cac ctg ttc gtg tcc ttc atc ctt cgt gcc ctg tcc aac     633
Ile His Met His Leu Phe Val Ser Phe Ile Leu Arg Ala Leu Ser Asn
            180                 185                 190 ttc atc aag gac gcc gtg ctc ttc tcc tca gat gat gtc acc tac tgc     681
Phe Ile Lys Asp Ala Val Leu Phe Ser Ser Asp Asp Val Thr Tyr Cys
        195                 200                 205 gat gcc cac agg gcg ggc tgc aag ctg gtc atg gtg ctg ttc cag tac     729
Asp Ala His Arg Ala Gly Cys Lys Leu Val Met Val Leu Phe Gln Tyr
    210                 215                 220 tgc atc atg gcc aac tac tcc tgg ctg ctg gtg gaa ggc ctc tac ctt     777
Cys Ile Met Ala Asn Tyr Ser Trp Leu Leu Val Glu Gly Leu Tyr Leu
225                 230                 235                 240 cac aca ctc ctc gcc atc tcc ttc ttc tct gaa aga aag tac ctc cag     825
His Thr Leu Leu Ala Ile Ser Phe Phe Ser Glu Arg Lys Tyr Leu Gln
                245                 250                 255
```

-continued

```
gga ttt gtg gca ttc gga tgg ggt tct cca gcc att ttt gtt gct ttg      873
Gly Phe Val Ala Phe Gly Trp Gly Ser Pro Ala Ile Phe Val Ala Leu
            260                 265                 270 tgg gct att gcc aga cac ttt ctg gaa gat gtt ggg tgc tgg gac atc      921
Trp Ala Ile Ala Arg His Phe Leu Glu Asp Val Gly Cys Trp Asp Ile
275                 280                 285 aat gcc aac gca tcc atc tgg tgg atc att cgt ggt cct gtg atc ctc      969
Asn Ala Asn Ala Ser Ile Trp Trp Ile Ile Arg Gly Pro Val Ile Leu
        290                 295                 300 tcc atc ctg att aat ttc atc ctt ttc ata aac att cta aga atc ctg     1017
Ser Ile Leu Ile Asn Phe Ile Leu Phe Ile Asn Ile Leu Arg Ile Leu
305                 310                 315                 320 atg aga aaa ctt aga acc caa gaa aca aga gga aat gaa gtc agc cat     1065
Met Arg Lys Leu Arg Thr Gln Glu Thr Arg Gly Asn Glu Val Ser His
                325                 330                 335 tat aag cgc ctg gcc agg tcc act ctg ctg atc ccc ctc ttt ggc         1113
Tyr Lys Arg Leu Ala Arg Ser Thr Leu Leu Leu Ile Pro Leu Phe Gly
            340                 345                 350 atc cac tac atc gtc ttc gcc ttc tcc cca gag gac gct atg gag atc     1161
Ile His Tyr Ile Val Phe Ala Phe Ser Pro Glu Asp Ala Met Glu Ile
        355                 360                 365 cag ctg ttt ttt gaa cta gcc ctt gcg tca ttc cag gga ctg gtg gtg     1209
Gln Leu Phe Phe Glu Leu Ala Leu Ala Ser Phe Gln Gly Leu Val Val
370                 375                 380 gcc gtc ctc tac tgc ttc ctc aac ggg gag gtg cag ctg gag gtt cag     1257
Ala Val Leu Tyr Cys Phe Leu Asn Gly Glu Val Gln Leu Glu Val Gln
385                 390                 395                 400 aag aag tgg cag caa tgg cac ctc cgt gag ttc cca ctg cac ccc gtg     1305
Lys Lys Trp Gln Gln Trp His Leu Arg Glu Phe Pro Leu His Pro Val
                405                 410                 415 gcc tcc ttc agc aac agc acc aag gcc agc cac ttg gag cag agc cag     1353
Ala Ser Phe Ser Asn Ser Thr Lys Ala Ser His Leu Glu Gln Ser Gln
            420                 425                 430 ggc acc tgc agg acc agc atc atc tga gaggctggag cagggtcacc           1400
Gly Thr Cys Arg Thr Ser Ile Ile
        435                 440 catggacaga gaccaagaga ggtcctgcga aggctgggca ctgctgtggg acagccagtc   1460
ttcccagcag acaccctgtg tcctccttca gctgaagatg cccctcccca ggccttggac   1520
tcttccgaag gatgtgaggc actgtggggc aggacaaggg cctgggattt ggttcgtttg   1580
ctcttctggg aagagaagtt cagggttccc agaaagggac agggaaataa atggttgcct   1640
tgggatgaga                                                          1650

<210> SEQ ID NO 4
<211> LENGTH: 440
<212> TYPE: PRT
<213> ORGANISM: Homo sapiens

<400> SEQUENCE: 4

Met Arg Pro His Leu Ser Pro Leu Gln Gln Leu Leu Pro Val
1               5                   10                  15

Leu Leu Ala Cys Ala Ala His Ser Thr Gly Ala Leu Pro Arg Leu Cys
                20                  25                  30

Asp Val Leu Gln Val Leu Trp Glu Glu Gln Asp Gln Cys Leu Gln Glu
            35                  40                  45

Leu Ser Arg Glu Gln Thr Gly Asp Leu Gly Thr Glu Gln Pro Val Pro
50                  55                  60
```

-continued

```
Gly Cys Glu Gly Met Trp Asp Asn Ile Ser Cys Trp Pro Ser Ser Val
 65                  70                  75                  80

Pro Gly Arg Met Val Glu Val Glu Cys Pro Arg Phe Leu Arg Met Leu
                 85                  90                  95

Thr Ser Arg Asn Gly Ser Leu Phe Arg Asn Cys Thr Gln Asp Gly Trp
                100                 105                 110

Ser Glu Thr Phe Pro Arg Pro Asn Leu Ala Cys Ala Val Asn Val Asn
                115                 120                 125

Asp Ser Ser Asn Glu Lys Arg His Ser Tyr Leu Leu Lys Leu Lys Val
            130                 135                 140

Met Tyr Thr Val Gly Tyr Ser Ser Leu Val Met Leu Leu Val Ala
145                 150                 155                 160

Leu Gly Ile Leu Cys Ala Phe Arg Arg Leu His Cys Thr Arg Asn Tyr
                165                 170                 175

Ile His Met His Leu Phe Val Ser Phe Ile Leu Arg Ala Leu Ser Asn
            180                 185                 190

Phe Ile Lys Asp Ala Val Leu Phe Ser Ser Asp Val Thr Tyr Cys
            195                 200                 205

Asp Ala His Arg Ala Gly Cys Lys Leu Val Met Val Leu Phe Gln Tyr
            210                 215                 220

Cys Ile Met Ala Asn Tyr Ser Trp Leu Leu Val Glu Gly Leu Tyr Leu
225                 230                 235                 240

His Thr Leu Leu Ala Ile Ser Phe Phe Ser Glu Arg Lys Tyr Leu Gln
                245                 250                 255

Gly Phe Val Ala Phe Gly Trp Gly Ser Pro Ala Ile Phe Val Ala Leu
                260                 265                 270

Trp Ala Ile Ala Arg His Phe Leu Glu Asp Val Gly Cys Trp Asp Ile
            275                 280                 285

Asn Ala Asn Ala Ser Ile Trp Trp Ile Ile Arg Gly Pro Val Ile Leu
290                 295                 300

Ser Ile Leu Ile Asn Phe Ile Leu Phe Ile Asn Ile Leu Arg Ile Leu
305                 310                 315                 320

Met Arg Lys Leu Arg Thr Gln Glu Thr Arg Gly Asn Glu Val Ser His
                325                 330                 335

Tyr Lys Arg Leu Ala Arg Ser Thr Leu Leu Leu Ile Pro Leu Phe Gly
                340                 345                 350

Ile His Tyr Ile Val Phe Ala Phe Ser Pro Glu Asp Ala Met Glu Ile
            355                 360                 365

Gln Leu Phe Phe Glu Leu Ala Leu Ala Ser Phe Gln Gly Leu Val Val
            370                 375                 380

Ala Val Leu Tyr Cys Phe Leu Asn Gly Glu Val Gln Leu Glu Val Gln
385                 390                 395                 400

Lys Lys Trp Gln Gln Trp His Leu Arg Glu Phe Pro Leu His Pro Val
                405                 410                 415

Ala Ser Phe Ser Asn Ser Thr Lys Ala Ser His Leu Glu Gln Ser Gln
                420                 425                 430

Gly Thr Cys Arg Thr Ser Ile Ile
                435                 440
```

METHODS AND REAGENTS FOR TREATING GLUCOSE METABOLIC DISORDERS

RELATED APPLICATIONS

This application is a divisional of U.S. Ser. No. 10/855,676, filed May 27, 2004, which is a continuation of U.S. Ser. No. 09/634,363, filed Aug. 9, 2000, now abandoned, which is a continuation-in part of U.S. patent application Ser. No. 09/500,817, filed on Feb. 10, 2000, now abandoned, which is a continuation-in-part of U.S. Ser. No. 09/499,526, filed on Feb. 10, 2000, now issued U.S. Pat. No. 7,396,809, which applications are is based on U.S. Provisional Patent Application Nos. 60/119,575 and 60/119,577, both filed Feb. 10, 1999, the disclosures of which are hereby incorporated herein by reference.

FIELD OF THE INVENTION

The invention relates to therapies for treating glucose metabolic disorders (e.g., glucose intolerance, insulin resistance, hyperglycemia, hyperinsulinemia and Type II diabetes mellitus). The therapies are based on the discovery that PYY induces glucose responsiveness in fetal and adult pancreatic islets.

BACKGROUND OF THE INVENTION

Diabetes is one of the most prevalent chronic diseases in the United States, and a leading cause of death, afflicting over 400 million diabetics in the world today. Estimates based on the 1993 National Health Interview Survey (NHIS) indicate that diabetes has been diagnosed in 1% of the U.S. population age <45 years, 6.2% of those age 45-64 years, and 10.4% of those age >65 years. As of 1995, an estimated 8 million persons in the United States were reported to have this chronic condition.

The total cost of diabetes in the United States has been estimated at $92 billion annually, including expenditures on medical products, hospitalization and the value of lost work. Substantial costs to both society and its citizens are incurred not only for direct costs of medical care for diabetes, but also for indirect costs, including lost productivity resulting from diabetes-related morbidity and premature mortality. Persons with diabetes are at risk for major complications, including diabetic ketoacidosis, end-stage renal disease, diabetic retinopathy and amputation. There are also a host of less directly related conditions, such as hypertension, heart disease, peripheral vascular disease and infections, for which persons with diabetes are at substantially increased risk.

Diabetes mellitus is a heterogeneous group of metabolic diseases which lead to chronic elevation of glucose in the blood (hyperglycemia). Diabetes is characterized by pancreatic islet destruction or dysfunction leading to loss of glucose regulation. The two major types of diabetes mellitus are Type I, also known as "insulin-dependent diabetes" ("IDDM") or "juvenile-onset diabetes", and Type II, also known as "non-insulin dependent" ("NIDDM") or "maturity-onset diabetes".

IDDM results from an autoimmune-mediated destruction of pancreatic β cells with consequent loss of insulin production, which results in hyperglycemia. Type I diabetics require insulin replacement therapy to ensure survival. While medications such as injectable insulin and oral hypoglycemics allow diabetics to live longer, diabetes remains the third major killer, after heart disease and cancer. However, these medications do not control blood sugar levels well enough to prevent swinging between high and low blood sugar levels, with resulting damage to the kidneys, eyes, and blood vessels. Data from the Diabetes Control and Complications Trial (DCCT) show that intensive control of blood glucose significantly delays complications of diabetes, such as retinopathy, nephropathy, and neuropathy, compared with conventional therapy consisting of one or two insulin injections per day. Intensive therapy in the DCCT included multiple injection of insulin three or more times per day or continuous subcutaneous insulin infusion (CSII) by external pump. Insulin pumps are one of a variety of alternative approaches to subcutaneous multiple daily injections (MDI) for approximating physiological replacement of insulin.

Type II diabetes is characterized by hyperglycemia in the presence of higher-than-normal levels of plasma insulin (hyperinsulinemia) and represents over 90% of all cases and occurs most often in overweight adults over 40 years of age. Progression of Type II diabetes is associated with increasing concentrations of blood glucose, coupled with a relative decrease in the rate of glucose-induced insulin secretion. In Type II diabetes, tissue processes which control carbohydrate metabolism are believed to have decreased sensitivity to insulin and therefore occur not from a lack of insulin production, but a decreased sensitivity to increased glucose levels in the blood and an inability to respond by producing insulin. Alternatively, diabetes may result from various defects in the molecular machinery that mediate the action of insulin on its target cells, such as a lack of insulin receptors on their cell surfaces. Treatment of Type II diabetes therefore frequently does not require administration of insulin but may be based on diet and lifestyle changes, augmented by therapy with oral hypoglycemic agents such as, for example, sulfonylurea.

The endocrine portion of the pancreas is composed of the islets of Langerhans, which appear as rounded clusters of islet cells embedded within the exocrine pancreas. Four kinds of islet cells compose the endocrine portion of the pancreas: (1) alpha (α) cells, constituting 20% of islet cells, which secret glucagon, a hormone which raises blood sugar levels; (2) beta (β) cells, which secrete insulin, a hormone which lowers blood sugar levels; (3) delta (δ) cells, which secrete growth hormone inhibiting hormone (GHIH) or somatostatin, a hormone which inhibits the secretion of insulin and glucagon; and (4) φ cells, or pancreatic polypeptide (PP) cells, which synthesize pancreatic polypeptide. Glucagon acts on several tissues to make energy available in the intervals between eating. In the liver, glucagon causes breakdown of glycogen and promotes gluconeogenesis from amino acid precursors. Pancreatic polypeptide inhibits pancreatic exocrine secretion of bicarbonate and enzymes, causes relaxation of the gallbladder, and decreases bile secretion. Insulin is known to cause the storage of excess nutrients arising during and shortly after eating. The major target organs for insulin are the liver, muscle and fat-organs specialized for storage of energy.

The most abundant cell in the islets, constituting 60-80% of the cells, is the insulin-producing β cell. The β cells of the human fetal pancreas are different from adult pancreatic β cells in that they release little or no insulin in response to glucose. (See, e.g., Tuch, B. E. et al. (1992) *J. Endocrin.* 132:159-67). This has been observed in both humans and rodents, and resembles the delayed insulin response to glucose observed in patients with Type II diabetes or malignant insulinoma. (Hellerström and Swenne (1991) *Diabetes* 40(2): 89-93; Tuch et al., supra). The inability of fetal β cells to produce insulin in response to glucose is not believed to be due to an inability to process insulin precursors. Adult human β cells synthesize preproinsulin and convert this into proinsulin (hPI) in the endoplasmic reticulum. Thereafter, hPI is split into insulin and C-peptide via a regulated pathway in the secretory granules. The rate of conversion of hPI in the adult β cell is high, resulting in a low hPI:insulin ratio both as regards to content and secretion (Gold, et al. (1981) *Diabetes* 30:77-82). This is also observed for fetal β cells, suggesting that β cell immaturity is not due to differences in the storage and release of proinsulin. (Tuch et al., supra). The acute release of both hPI and insulin from the fetal β cell in response to an increase in $Ca^{2+}$ and cAMP suggests that the cell releases its secretory products via a regulated, rather than a constitutive pathway. (Rhodes and Halban (1987) *J. Cell Biol.* 105:145-53).

The lack of glucose responsiveness in fetal β cells is thought to be due to immature glucose metabolism. The molecular mechanism underlying glucose-induced insulin secretion in adult β cells involves the closure of ATP-sensitive $K^+$ ($K_{ATP}$) channels in the plasma membrane, thereby inhibiting $K^+$ efflux through $K^+$ ATP channels, leading to depolarization of the cell membrane. (Jones, P. M. and Persaud, S. J. (1998) *Endocrine Reviews* 19(4):429-61; Mendonca et al., supra; Cook, D. L. and Hales C. N. (1984) *Nature (London)* 311:271-73). Consequently, cytosolic $Ca^{2+}$ concentration increases as a result of the membrane depolarization and $Ca^{2+}$ influx through L-type (voltage-sensitive) $Ca^{2+}$ channels. Glucose raises the intracellular concentration of cAMP and of regulators derived from membrane phospholipids, including inositol triphosphate ($IP_3$), diacylglycerols (DAG), arachidonic acid (AA) and phosphatidic acid. (See Jones and Persaud, supra). It has been suggested that reduced insulin secretion in response to glucose reflects the uncoupling between glucose metabolism and membrane cell depolarization. (Mendonca et al., supra). Studies indicate that the ATP-sensitive $K^+$ channel, although fully developed, is not properly regulated in the fetal β cell and that the deficient secretory response to glucose may reflect an immature mitochondrial glucose metabolism resulting in an inability to close the otherwise normal ATP-sensitive $K^+$ channel. (Hellerström and Swenne, supra).

Pancreatic development occurs in discrete stages and is regulated by endocrine hormones produced by pancreatic cells themselves or by other tissues. In the rat, the pancreatic anlage forms at embryonic ("e") day 10.5 ("e10.5") by fusion of the dorsal and ventral pancreatic primordial buds that arise as protrusions from the duodenal endoderm. (Pictet, R. and Rutter, W. J. (1972) "Development of the Embryonic Endocrine Pancreas." In D. Steiner and N. Freinkel (eds.) *Handbook of Physiology*, The Endocrine Pancreas, Vol. 1, Section 8, Am. Physiol. Soc., pp. 25-66; Myrsén-Axcrona, U. et al. (1997) *Regulatory Peptides* 68:165-75). Islet hormones appear sequentially in the developing pancreas: for example, glucagon appears at e10 in mouse and e11 in rat, insulin producing cells appear in e12, somatostatin producing cells appear at e17. (See Myrsén-Axcrona et al., supra). It is thought that pancreatic islet cells differentiate in response to endocrine signals from a common precursor cell in the pancreatic ducts. Sometime between the end of the rat fetal stage (e21) and neonatal stages (post-birth) the fetal β cells acquire the ability to secrete insulin in response to glucose. The insulin response at this age is monophasic and is not blocked by $Ca^{2+}$ antagonists. A clear biphasic pattern of insulin secretion in response to glucose is detected only 3 days after birth. (Mendonca, A. C. et al. (1998) *Brazilian J. Med. Biol. Res.* 31(6):841-46). The mechanism by which this "gain of function" or "gain of glucose responsivity" is achieved is not known, nor have the factors that regulate the maturation and gain of function been identified or characterized. In addition, the physiological changes associated with gain of glucose responsivity in pancreatic β cells are not known.

The instant invention is based on the discovery that a factor, "peptide yY" or "PYY", triggers gain of function in glucose non-responsive fetal and adult islets which leads to glucose responsivity, and therefore provides therapies for diseases affecting glucose metabolism such as Type II diabetes.

SUMMARY OF THE INVENTION

The present invention relates to the discovery that PYY can induce and maintain glucose responsivity in fetal and adult pancreatic islets. For example, we show that treatment of glucose non-responsive e21 islets from fetal rat pancreas for five days with PYY in vitro induced maturation of the islets, which then responded to glucose by releasing insulin. We also show that glucose sensing can be recovered in adult islets by treatment with PYY, and that glucose sensing can be maintained for longer in adult islets treated with PYY. Prior to the present invention, trophic or growth factors that are capable of stimulating islet maturation have not previously been identified in the art.

In one aspect, the invention comprises a method for altering the differentiated state of pancreatic islet cells, comprising administering to the pancreatic islets or isolated β cells, a PYY peptide or PYY agonist of (e.g., which mimics or enhances) PYY activity, collectively referred to herein "PYY Therapeutic". In one embodiment, administration of a PYY Therapeutic causes the islets or cells to become glucose responsive. The glucose responsive islets or cells are thereby stimulated to produce insulin when exposed to glucose. In another aspect, the invention comprises methods for inducing islets to express markers indicative of mature islets, or for β cells to express markers indicative of mature β cells by contacting the islets or β cells with a PYY Therapeutic. In a preferred embodiment, the islets or cells are human pancreatic islets or cells.

The invention further provides methods for preparing glucose responsive pancreatic islets or β cells, comprising administering to glucose non-responsive pancreatic islets or β cells an effective amount of a composition comprising a PYY Therapeutic.

In another aspect, the invention provides a method for modifying glucose metabolism in an animal, comprising administering to the animal a pharmaceutically effective amount of a composition comprising a PYY Therapeutic and a pharmaceutically acceptable carrier, in order to enhance the glucose responsiveness of pancreatic β cells thereby. In a preferred embodiment, the invention provides a method for treating a disease associated with altered glucose metabolism, comprising administering to an animal a pharmaceutically effective amount of a composition comprising a PYY Therapeutic and a pharmaceutically acceptable carrier, in an amount sufficient to increase the glucose responsiveness of pancreatic β cells.

In another aspect, the invention provides differentiated islets and β cells generated by contacting undifferentiated islets or cells from a vertebrate organism with a PYY Therapeutic. In a preferred embodiment, the invention provides pancreatic islets or β cells that secrete insulin in response to glucose and a pharmaceutically acceptable carrier suitable for pharmaceutical administration to an animal, wherein the cellular composition can secrete insulin in vivo in response to glucose.

In still another aspect, the invention provides a method for treating a disease associated with altered glucose metabolism, comprising administering to an animal a pharmaceutically effective amount of a composition comprising pancreatic islets or β cells which have gained glucose-responsiveness by treatment with a PYY Therapeutic according to the invention. In one embodiment, the glucose-responsive islets or cells obtained by treating pancreatic islets or β cells with a PYY Therapeutic are administered to an animal in a composition containing a pharmaceutically acceptable carrier in an amount sufficient to increase the glucose responsiveness of the animal. In another embodiment, the composition of a PYY treated glucose-responsive cells comprises additional agents, such as a PYY Therapeutic. The cell composition may be conjointly administered either simultaneously, sequentially or separately with a PYY Therapeutic. The method may be used for treating a disease that is associated with a condition such as insulin resistance, glucose intolerance or glucose non-responsiveness, hyperglycemia, obesity, hyperlipidemia and hyperlipoproteinemia in an animal. In a preferred embodiment, the instant invention is used to treat Type II diabetes mellitus.

Preferred PYY peptides include polypeptides which correspond to a mature PYY protein, or to a biologically active fragment thereof. The PYY peptide is preferably a mammalian PYY, e.g., encoded by a mammalian PYY gene, and even more preferably a human PYY protein, e.g., such as represented in SEQ ID NO:2. In certain embodiments, the PYY peptide will be at least 70 percent identical with an amino acid sequence of SEQ ID NO:2, and more preferably at least 80, 85, 90 or 95 percent identical. In certain embodiments, the PYY peptide can be encoded by a nucleic acid that hybridizes to SEQ ID NO:1, preferably under stringency conditions including a wash step of 2.0×SSC at 65° C., and even more preferably under stringency conditions including a wash step of 0.2×SSC at 65° C.

PYY agonists which can be used as PYY Therapeutics include any compound having the effect of inducing the activity of PYY. Preferred agonists comprise compounds capable of inhibiting dipeptidylpeptidase, preferably dipeptidylpeptidase IV (DPIV).

In another preferred embodiment, the PYY Therapeutic, PYY Therapeutic-treated islets and/or PYY Therapeutic-treated cells are administered to an animal with an agent capable of inhibiting the degradation of the PYY Therapeutic either simultaneously, sequentially or separately with the PYY Therapeutic. In a preferred embodiment, the agent is co-administered with the PYY Therapeutic. Preferred inhibitors are dipeptidylpeptidase inhibitors. In another preferred embodiment, the agent is administered with pancreatic islets or cells that had been made glucose-responsive by treatment with a PYY Therapeutic according to the invention. In another preferred embodiment, the agent is administered with PYY and pancreatic islets or cells that had been made glucose-responsive by treatment with a PYY Therapeutic according to the invention.

In other embodiments, the PYY Therapeutic is a compound that binds to a PYY receptor such as the PYY Y1 receptor, and mimics (agonist) or inhibits (as an antagonist) the activity for PYY. In preferred embodiments, such agents are small organic molecules, e.g., having a molecular weight less than 7000 amu, and more preferably less than 5000 amu, 1000 amu, or even 500 amu. Agonists can be used to induce and/or maintain glucose sensing. Agonists can be used to inhibit or otherwise suppress glucose sensing, e.g., to treat hyperinsulinomid or hyperglycemia.

In a preferred embodiment, the invention provides a method for maintaining normal pancreatic islet function (i.e., glucose responsiveness) in islet or cell transplants, comprising administering to ex vivo pancreatic islets or cells a PYY Therapeutic. In this way, donor pancreatic islets or cells that are to be transplanted into a host animal can be maintained as functional with respect to their ability to respond to glucose by producing insulin. Alternatively, the pancreatic islet cells may be autologous failed β cells of the host which are treated with a PYY Therapeutic to enrich for glucose responsive cells or to revive their glucose responsiveness prior to reimplantation into the animal.

In still another aspect, the invention provides a method for identifying a PYY Therapeutic, comprising administering to fetal pancreatic islets or cells, or adult pancreatic cells that are non-responsive to glucose, an effective amount of an agent and comparing the cellular response to the agent with the cellular response to PYY. In a preferred embodiment, the PYY Therapeutic induces glucose responsiveness in an unresponsive pancreatic islet or cell. In another preferred embodiment, the PYY Therapeutic enhances glucose responsiveness in a partially glucose intolerant or low insulin expressing pancreatic islet or β cell. In yet another preferred embodiment, the PYY Therapeutic recovers glucose responsiveness in failed pancreatic islets or cells.

In another aspect, the invention provides a method for identifying antagonists (i.e., inhibitors) of PYY. Such antagonists may provide a means by which glucose responsiveness in pancreatic cells (e.g., in progenitor cells or insulinoma cells) can be prevented or inhibited. In one embodiment, a PYY antagonist can inhibit the effect of native PYY, either directly or indirectly, on pancreatic progenitor cells. In another embodiment, a PYY antagonist can inhibit the effect of PYY, either directly or indirectly, on insulin levels when administered to patients suffering hyperinsulinemia (e.g., such as that resulting from insulinoma). The identification of PYY antagonists can then be used to identify inhibitors of PYY antagonists ("PYY antagonist inhibitors").

In still another aspect, the invention provides a method for screening a DNA library for the presence of a gene encoding a PYY agonist, a PYY antagonist, PYY inhibitor or a PYY antagonist inhibitor. In one embodiment, a variegated library of PYY homologs or agonists is generated by combinatorial mutagenesis at the nucleic acid level, and is encoded by a variegated gene library. For instance, a mixture of synthetic oligonucleotides can be enzymatically ligated into gene sequences such that the degenerate set of potential PYY sequences are expressible as individual polypeptides, or alternatively, as a set of larger fusion proteins (e.g., for phage display) containing the set of PYY sequences therein.

In yet another aspect, the present invention provides a diagnostic assay for assessing whether or not a patient suspected of having a glucose metabolic disorder has a defect in his/her PYY functions. For example, the assay can detect levels of PYY in serum or other bodily fluid. In other embodiments, the assay can detect mutations to the PYY gene, e.g., which effect secretion, serum half-life or potency of the encoded protein. In one preferred embodiment, the subject method can be used to ascertain if a patient has a PYY gene that carries a mutation in the secretion signal sequence that decreases the level of secretion of the protein.

In yet another embodiment, the invention provides a transgenic non-human vertebrate animal in which PYY inductive pathways are inhibited in one or more tissues of said animal by one of either expression of an antagonistic PYY polypeptide or disruption of a gene encoding PYY or a PYY agonist.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., Sambrook, Fritsch and Maniatis (eds.) (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins, eds., 1984); *Transcription And Translation* (B. D. Hames & S. J. Higgins, eds., 1984); *Culture Of Animal Cells* (R. I. Freshney, Alan R. Liss, Inc., 1987); *Immobilized Cells and Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos, eds., 1987, Cold Spring Harbor Laboratory); *Methods In Enzymology*, Vols. 154 and 155 (Wu et al., eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986).

Other features and advantages of the invention will be apparent from the following Figures, Detailed Description, and from the claims.

DETAILED DESCRIPTION OF THE INVENTION (i) Overview of the Invention

The hormonal signals required, and the point in time the hormonal signaling takes place during fetal development, for the maturation of β cells of the pancreas (i.e., gain of the ability to produce insulin in response to glucose) has now been identified. Pancreatic islet development proceeds through stages during fetal gestation which are punctuated by discrete transitions. The initial period is a protodifferentiated state which is characterized by the commitment of pluripotent stem cells to the islet cell lineage, as manifested by the expression of insulin and glucagon.

Figure 6:
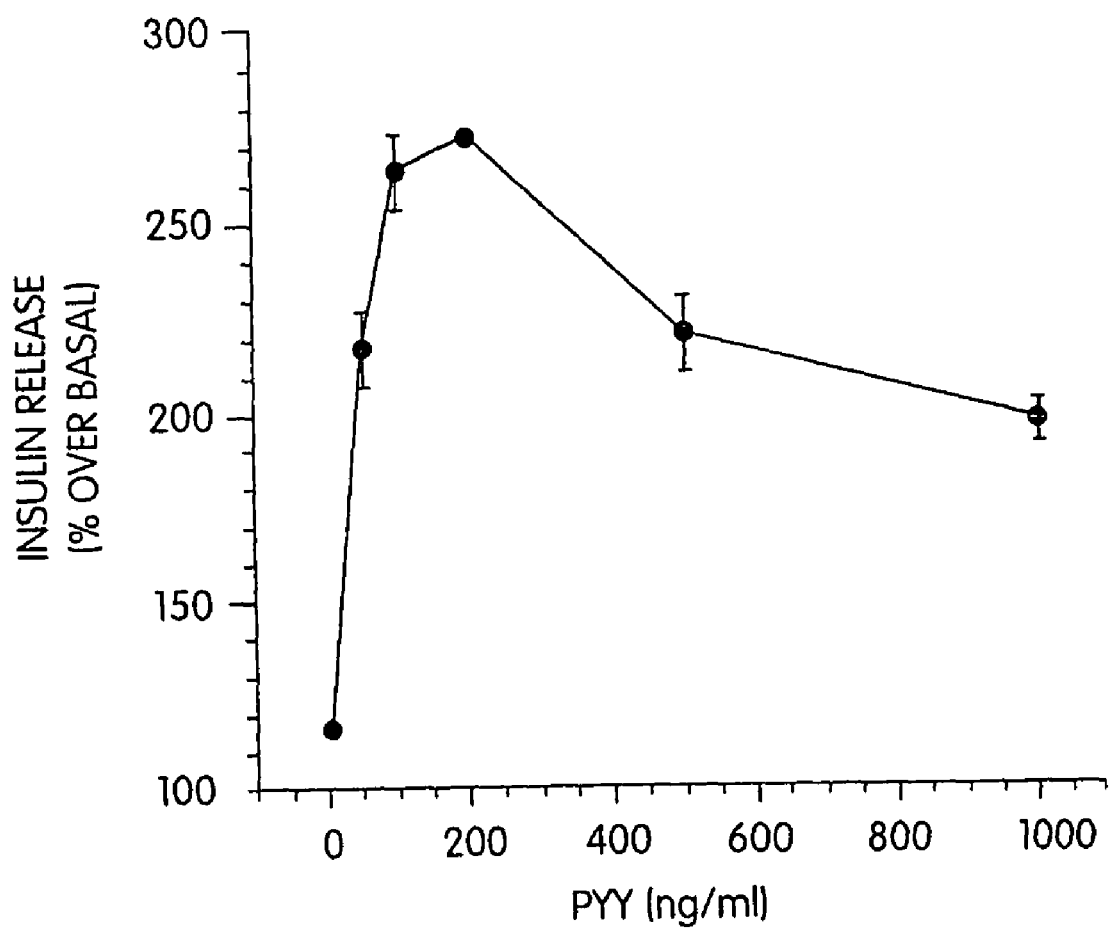
FIG. 6: PYY effect on adult islets.

The invention relates to the discovery that treatment of fetal islets with Peptide YY (PYY) in vitro caused maturation of the glucose-unresponsive islets into mature islets that responded to glucose by releasing insulin. Significantly, PYY has also been shown to restore glucose-responsiveness to adult pancreatic islets that have otherwise lost the ability to secrete insulin in response to glucose (FIG. 6). These findings indicate that PYY agonists can be used to induce the formation of glucose-responsive pancreatic tissue, both ex vivo and in vivo from progenitor cell populations. Likewise, the perfect findings demonstrate that PYY agonists can be used to maintain or otherwise extend the time that β cells are glucose responsive, as well as to restore glucose responsiveness to β cells.

In one aspect, the present discovery provides reagents and methods for generating glucose-responsive cells from pancreatic progenitor cells. In other embodiments, the subject method can be used to restore or maintain glucose responsiveness in cultured pancreatic islets or other pancreatic cells, in particular pancreatic islets or cells that are being prepared for transplantation into an animal, preferably a human. In other embodiments, the subject method can be used to prevent loss of glucose-responsive pancreatic cells in vivo.

In general, the invention relates to methods for regulating (inducing or maintaining) glucose-responsive pancreatic islets or isolated β cells, through the use of a PYY peptide, an analog or derivative of PYY, or an agonist thereof (hereinafter "PYY agonist"). For ease of reading, both classes of agents are collectively referred to herein as "PYY Therapeutic". Administration of a PYY Therapeutic by the subject method can cause the treated pancreatic cells to acquire glucose responsiveness, thereby enriching an islet or population of β cells for glucose-responsive β cells, or will induce islets or cells which have lost the ability to respond to glucose to regain glucose responsiveness.

A PYY Therapeutic may be administered in vivo to a subject in a pharmacologically acceptable composition or may be administered ex vivo to cultured islets or cell lines. In the case of transplant material (i.e., PYY treated pancreatic islet or β cells), the cells may be administered to an animal with the PYY Therapeutic, alone or in combination with other agonists that are capable of enhancing the effect of a PYY Therapeutic.

In yet another embodiment, the animal or pancreatic islets or cells thereof, may be treated with factors that may induce or enhance the production by the islet cells themselves of other factors which may enhance PYY-induced glucose responsiveness. For example, the insulin gene contains multiple cis-acting elements (i.e., glucose responsive enhancer and repressor elements) that contribute to the basal activity, tissue specificity and metabolic response of the insulin promoter. (Sander, M. et al. (1998) *Proc. Natl. Acad. Sci. USA* 95:11572-77; Odagiri, H. et al. (1996) *J. Biol. Chem.* 271: 1909-1915). Sander et al. have demonstrated that a glucose responsive element that functions as an enhancer in primary cultured fetal and adult rat islets functions as a repressor in both fully developed β cell tumor cells and β hyperplasia cells from pretumorigenic, hyperplastic cells (i.e., differentiated and de-differentiated cell lines, respectively), suggesting fundamental differences in insulin gene regulation between immortalized β cells and native islet cells. Sander et al. found that a distinct glucose-responsive complex that bound to the glucose responsive enhancer element was found only in cultured islet cells and that these differences could be accounted for by the absence of a repressor in primary cultured β cells, allowing perhaps a ubiquitous activator to function or an activator that is present only in primary islet cells, which overrides the effect of a ubiquitous repressor. Thus, the effects of treatment of β cells with PYY could be enhanced by co-treatment with agents that alter the levels of such factors (e.g., transcription factors) or other factors that participate in the regulation of the insulin gene in response to glucose.

Alternatively, the pancreatic islets or cells may be treated with factors that may cause or enhance the production by other cell types of other factors which may enhance PYY induced glucose responsiveness. For example, β, δ or PP cells may be stimulated by PYY to produce factors that may alter gene expression or glucose metabolism in an animal.

Agonists of the PYY receptors may also be identified using the instant invention. PYY belongs to the family of peptides termed the "PP family", other members of which include NPY and PP. Several PP-family receptor subtypes have been cloned. These all contain several transmembrane domains and belong to the G-protein coupled superfamily of receptors. The PP receptor family includes Y1-R, Y2-R, Y3-R, Y4-R, Y5-R and Y6-R, each receptor differing in binding properties and tissue distribution and sequence identity. (Jackerott, M. and Larsson, L. I. (1997) *Endocrinol.* 138:5013-18). Y1, Y2, Y5 and Y6, for example, bind to PYY and NP Y3-36 and PYY3-36 C-terminal fragments. For a review, see Gehlert D. R. (1998) *Proc. Soc. Exp. Biol. Med.* 218(1):7-22. Naturally occurring endogenous agonists of the PYY receptors have been described (e.g., PYY1-36 and NPY1-36).

Alternatively, factors capable of increasing PYY receptor expression in pancreatic cells may also be administered to a subject or to islets or cells ex vivo to enhance the glucose responsiveness effect of PYY. (See e.g., Holliday, N. D. and Cox, H. M. (1996) *Br. J. Pharmacol.* 119(2):321-9). Increased PYY receptor levels would further enhance the effect of a PYY Therapeutic on pancreatic β cells. In addition, PYY receptor number in pancreatic β cells may be increased by introduction of recombinant vectors comprising DNA sequences encoding a PYY receptor. Though the P2 and P5 receptors are preferred, P1, P3, P4 and P6 or other PYY specific receptor may be induced or introduced.

Alternatively, agents capable of enhancing glucose transport or phosphorylation (e.g., that regulated by glucokinase expression) may be administered in conjunction with the PYY Therapeutic. (See, e.g., Schuit, F. C. (1996) *Horm. Res.* 46:99-106). Yet further, the expression level of the glucose transporter GLUT2 has been found to be reduced in animal models of diabetes, and transfection of GLUT2 into cell lines can confer glucose sensitivity on the cells, or transgenic mice with downregulated GLUT2 in β cells or diabetic rats. (Thorens, B. et al. (1990) *Proc. Acad. Sci. USA* 87: 6492-96; Hughes, S. D. et al. (1992) *Proc. Natl. Acad. Sci. USA* 89:688-92; Valera et al. (1994) *J. Biol. Chem.* 269:28543-46; Johnson, D. et al. (1990) *Science* 250:546-49). The introduction of a GLUT-2 gene into a non-pancreatic pituitary cell line AtT-20$_{ins}$ conferred glucose stimulated insulin release, glucose potentiation of non-glucose secretagogues, and an increase in insulin content (Hughes et al., supra) and restoration of GLUT-2 expression confers glucose responsiveness and increased glucokinase activity in rat insulinoma (RIN) cells (Ferber, S. et al. (1994) *J. Biol. Chem.* 269(15):11523-29).

Prior to transplantation, donor pancreatic islet cells are cultured, which results in the loss of their ability to secrete insulin in response to glucose. The methods provided herein provide means for maintaining cultured pancreatic cells as functionally mature glucose responsive β cells that continue to produce insulin. Alternatively, cultures of pancreatic cells that have lost their glucose responsiveness can be restored to glucose-responsive cells by the instant invention.

Thus, in a preferred embodiment, the invention provides methods for treating diseases associated with altered or faulty glucose metabolism, for example, in diseases which are characterized by an inability to respond to increased or decreased levels of glucose or its byproducts in the blood. The discovery that PYY potentiates or restores glucose responsiveness provides numerous strategies for restoring or augmenting insulin production in an animal, preferably in humans.

In another preferred embodiment, PYY analogs, agonists or antagonists may be identified by the methods of the invention by comparison of treatment of glucose-nonresponsive cells (e.g., fetal islets or β cells or non-responsive adult islets or β cells with test factors and comparing their effects to the effects elicited with PYY. The invention provides methods for screening protein, peptide or DNA libraries for the presence of a gene encoding a PYY analogs, agonist or PYY antagonist, according to art-known methods.

In a preferred embodiment, the invention provides a method for identifying antagonists of PYY and the genes that encode them. The antagonist may be a naturally occurring gene product or variants thereof or a synthetic molecule of some sort, such as, for example, an antisense, a ribozyme molecule and a small organic molecule. The invention also provides methods for identifying naturally-occurring or synthetic antagonists, which inhibit or antagonize a PYY antagonist. Such "antagonists to antagonists" of PYY (or "PYY antagonist inhibitors") can be identified to provide strategies for inhibiting the PYY antagonists in order to enhance the response of cells to PYY.

In a preferred aspect of the invention, diseases associated with altered glucose metabolism can be treated by administering a pharmaceutically effective amount of PYY treated pancreatic β cells (which have gained glucose-responsiveness). In one embodiment, the glucose-responsive cells are administered to an animal in a composition containing a pharmaceutically acceptable carrier. In another embodiment, the composition of glucose-responsive cells further comprises other factors that may augment insulin secretion, such as a PYY Therapeutic.

Alternatively, the composition may be conjointly administered either simultaneously, sequentially or separately with a protease inhibitor which prolongs the serum half-life of a PYY Therapeutic, e.g., such as a dipeptidylpeptidase inhibitor. In a preferred embodiment, the dipeptidylpeptidase inhibitor is a DPIV inhibitor. The cell composition may be administered either simultaneously, sequentially or separately with the additional factors. The method may be used for treating a disease that is associated with a condition such as insulin resistance, glucose intolerance or glucose non-responsiveness, hyperglycemia, obesity, hyperlipidemia and hyperlipoproteinemia in an animal.

In a preferred embodiment, the PYY Therapeutic induces glucose responsiveness in an unresponsive cell of the pancreatic lineage. In another preferred embodiment, the PYY Therapeutic enhances glucose responsiveness by causing maturation of pancreatic progenitor cells. In another preferred embodiment, the PYY Therapeutic enhances glucose responsiveness in a partially glucose intolerant or low insulin expressing pancreatic β cell from a post-partem animal. In yet another preferred embodiment, the PYY Therapeutic recovers glucose responsiveness in failed pancreatic cells from a post-partem animal.

In another aspect, the invention provides differentiated β cells generated in cell culture by contacting an undifferentiated cell from a vertebrate organism with a PYY Therapeutic. In a preferred embodiment, the invention provides pancreatic β cells that secrete insulin in response to glucose for use in transplantation and a pharmaceutically acceptable carrier suitable for pharmaceutical administration to an animal, wherein the cellular composition can secrete insulin in vivo in response to glucose.

This invention further contemplates a method for generating sets of combinatorial mutants of PYY proteins, as well as libraries of truncation mutants, and is especially useful for identifying potential variant sequences (e.g., homologs or analogs) that are functional in binding to a receptor for PP proteins and which alters the glucose-responsiveness of pancreatic islets or cells. The purpose of screening such combinatorial libraries is to generate, for example, novel PYY homologs or analogs which are either agonists or antagonist, or alternatively, possess novel activities altogether. To illustrate, PYY homologs or analogs can be engineered by the present method to provide more efficient binding to a cognate receptor, yet still retain at least a portion of an activity associated with PYY. Thus, combinatorially-derived homologs can be easily generated to have an increased potency relative to a naturally occurring form of the protein. Likewise, PYY homologs or analogs can be generated by the present combinatorial approach to act as antagonists, in that they are able to mimic, for example, binding to other extracellular matrix components (such as receptors), yet not induce any biological response, thereby inhibiting the action of authentic PYY Therapeutics. Moreover, manipulation of certain domains of PYY by the present method can provide domains more suitable for use in fusion proteins, such as one that incorporates portions of other proteins which are derived from the extracellular matrix and/or which bind extracellular matrix components.

In one aspect of this method, the amino acid sequences for a population of PYY homologs, analogs or other related proteins are aligned, preferably to promote the highest homology possible. Such a population of variants can include, for example, PYY homologs from one or more species that are capable of inducing glucose-responsiveness. Amino acids which appear at each position of the aligned sequences are selected to create a degenerate set of combinatorial sequences. In a preferred embodiment, the variegated library of PYY variants is generated by combinatorial mutagenesis at the nucleic acid level, and is encoded by a variegated gene library. For instance, a mixture of synthetic oligonucleotides can be enzymatically ligated into gene sequences such that the degenerate set of potential PYY sequences are expressible as individual polypeptides, or alternatively, as a set of larger fusion proteins (e.g., for phage display) containing the set of PYY sequences therein.

In yet another embodiment, the invention provides a transgenic non-human vertebrate animal in which PYY inductive pathways are inhibited in one or more tissues of said animal by one of either expression of an antagonistic PYY polypeptide or disruption of a gene encoding a PYY Therapeutic.

In a preferred embodiment, the progenitor cells are inducible to differentiate into pancreatic β cells. The subject pancreatic β cells are stimulated to be glucose responsive and to produce insulin in response to glucose. The subject pancreatic β cells can also be characterized on the basis of specific antigenic markers or other markers that may be expressed on the cell surface, e.g., integrins, lectins, gangliosides, or transporters, or on the basis of specific cellular morphology. All of these techniques are known and available to the one skilled in the art. Such pancreatic β cells maybe characterized in certain circumstances by the expression of one or more of: homeodomain type transcription factors such as STF-1; PAX gene(s) such as PAX6; PTF-1; hXBP-1; HNF genes(s); villin; tyrosine hydroxylase; insulin; glucagon; and/or Neuropeptide Y.

In a preferred embodiment the subject animal of the invention is a mammal, preferably a human.

(ii) Definitions

For convenience, certain terms employed in the specification, examples, and appended claims are collected here.

The term "agonist", as used herein, is meant to refer to an agent that upregulates (e.g., mimics potentiates or enhances) at least one PYY bioactivity. A PYY agonist can be a wild-type PYY protein or derivative thereof having at least one bioactivity of a wild-type PYY protein or peptidomimetic of PYY which functions as an agonist of (e.g., mimics) PYY activity. A PYY agonist can also be a compound that upregulates expression of a PYY gene or which increases at least one bioactivity of an PYY protein. A PYY agonist therefore includes those agents that upregulate the production and/or secretion of insulin in response to glucose. An agonist can also be a compound which increases the interaction of a PYY polypeptide with another molecule, e.g., a PP family receptor, or which mimics the binding to and distortion of a PYY receptor by native PYY. Another illustrative agonist is a compound which enhances binding of a PYY or PYY receptor transcription factor to the upstream region of a PYY or PYY receptor gene, or of an insulin gene transcription factor to the upstream region of an insulin gene, thereby enhancing the synthesis of the insulin protein. An agonist can also be a compound that upregulates expression of a PYY or insulin gene or which increases the amount of PYY or insulin protein present, e.g., by increasing protein synthesis or decreasing protein turnover. Further, a PYY agonist can be a PYY antagonist inhibitor.

"α cells" are found in the islets of Langerhans in the pancreas. Alpha cells secrete glucagon, a hormone that has effects opposite to those of insulin (it raises blood glucose levels).

The term "blood glucose level" refers to the concentration of glucose in blood. The normal blood glucose level (euglycemia) is approximately 120 mg/dl. This value fluctuates by as much as 30 mg/dl in non-diabetics.

As used herein the term "animal" refers to vertebrates, preferably mammals, and most preferably humans. Likewise, a "patient" or "subject" to be treated by the method of the invention can mean either a human or non-human animal.

The term "antagonist" as used herein is meant to refer to an agent that down-regulates (e.g., suppresses or inhibits) at least one PYY bioactivity. A PYY antagonist can be a compound which inhibits or decreases the interaction between a PYY protein and another molecule, e.g., a PYY receptor. Alternatively, a preferred antagonist is a compound which inhibits or decreases binding of a PYY or PYY receptor transcription factor to the upstream region of a PYY or PYY receptor gene, or of an insulin gene transcription factor to the upstream region of an insulin gene, thereby blocking the synthesis of the insulin protein. An antagonist can also be a compound that downregulates expression of a PYY or insulin gene or which reduces the amount of PYY or PYY antagonist can be a dominant negative form of a PYY polypeptide. The PYY antagonist can also be a nucleic acid encoding a dominant negative form of a PYY polypeptide, a PYY antisense nucleic acid, or a ribozyme capable of interacting specifically with a PYY RNA. Yet other PYY antagonists are molecules which bind to a PYY polypeptide or its receptor and inhibit its action. Such molecules include peptides, antibodies and small molecules.

The terms "β cell" or "pancreatic β cell" are interchangeable as used herein and refer to cells in the pancreatic islets that are of the lineage of cells that produce insulin in response to glucose. β cells are found in the islets of Langerhans in the pancreas. β cells secrete insulin in a regulated fashion in response to blood glucose levels. In Type I or insulin dependent diabetes mellitus (IDDM) β cells are destroyed through an auto-immune process. Since the body can no longer produce endogenous insulin, injections of exogenous insulin are required to maintain normal blood glucose levels.

"Biological activity" or "bioactivity" or "activity" or "biological function", which are used interchangeably, for the purposes herein means an effector or antigenic function that is directly or indirectly performed by a PYY Therapeutic (whether in its native or denatured conformation), or by any subsequence thereof. Biological activities include binding to a target nucleic acid e.g., an upstream region of a gene, which is regulated by a PYY induced transcription factor. A PYY bioactivity can be modulated by directly affecting a PYY polypeptide. Alternatively, a PYY bioactivity can be modulated by modulating the level of a PYY polypeptide, such as by modulating expression of a PYY gene or by modulating the turnover of the PYY protein.

As used herein, the term "cellular composition" refers to a preparation of cells, which preparation may include, in addition to the cells, non-cellular components such as cell culture media, e.g. proteins, amino acids, nucleic acids, nucleotides, co-enzyme, anti-oxidants, metals and the like. Furthermore, the cellular composition can have components which do not affect the growth or viability of the cellular component, but which are used to provide the cells in a particular format, e.g., as polymeric matrix for encapsulation or a pharmaceutical preparation.

The term "culture medium" is recognized in the art, and refers generally to any substance or preparation used for the cultivation of living cells. Accordingly, a "tissue culture" refers to the maintenance or growth of tissue, e.g., explants of organ primordia or of an adult organ ex vivo so as to preserve its architecture and function. A "cell culture" refers to a growth of cells ex vivo or in vitro; although the cells proliferate they do not organize into tissue per se.

Tissue and cell culture preparations of the subject microorgan explants and amplified progenitor or β cell populations can take on a variety of formats. For instance, a "suspension culture" refers to a culture in which cells multiply while suspended in a suitable medium. Likewise, a "continuous flow culture" refers to the cultivation of cells or ductal explants in a continuous flow of fresh medium to maintain cell growth, e.g., viability. The term "conditioned media" refers to the supernatant, e.g., free of the cultured cells/tissue, resulting after a period of time in contact with the cultured cells such that the media has been altered to include certain paracrine and/or autocrine factors produced by the cells and secreted into the culture.

The term "DPIV inhibitor" as referred to herein includes protease inhibitors, preferably serine protease inhibitors, such as peptidyl boronic acids (boroProline), peptidyl aldehydes, peptidyl chloromethyl halides and the like.

By "enhancing differentiation of a cell" is meant the act of increasing the extent of the acquisition or possession of one or more characteristics or functions which differ from that of the original cell (i.e., cell specialization). This can be detected by screening for a change in the phenotype of the cell (e.g., identifying morphological changes in the cell and/or surface markers on the cell).

"Enhancing survival or maintenance of a cell" encompasses the step of increasing the extent of the possession of one or more characteristics or functions which are the same as that of the original cell (i.e., cell phenotype maintenance).

The term "explant" refers to a portion of an organ taken from the body and grown in an artificial medium.

The condition of "hyperglycemia" (high blood sugar) is a condition in which the blood glucose level is too high. Typically, hyperglycemia occurs when the blood glucose level rises above 180 mg/dl. Symptoms of hyperglycemia include frequent urination, excessive thirst and, over a longer time span, weight loss.

On the other hand, "hypoglycemia" (low blood sugar) is a condition in which the blood glucose level is too low. Typically, hypoglycemia occurs when the blood glucose level falls below 70 mg/dl. Symptoms of hypoglycemia include moodiness, numbness of the extremities (especially in the hands and arms), confusion, shakiness or dizziness. Since this condition arises when there is an excess of insulin over the amount of available glucose it is sometimes referred to as an insulin reaction.

The term "impaired glucose tolerance" is used to describe a person who, when given a glucose tolerance test, has a blood glucose level that falls between normal and hyperglycemic. Such a person is at a higher risk of developing diabetes although they are not considered to have diabetes.

As used herein, the term "gene" or "recombinant gene" refers to a nucleic acid comprising an open reading frame encoding a polypeptide of the present invention, including both exon and (optionally) intron sequences. A "recombinant gene" refers to nucleic acid encoding such regulatory polypeptides, which may optionally include intron sequences which are either derived from a chromosomal DNA.

The terms "glucose non-responsive" or "glucose non-responsiveness" as used herein describe both the complete inability of cells, islets or animals to respond to treatment with or administration of glucose, as well as decreased responsiveness to glucose (e.g., by cells that do not produce sufficient levels of insulin in response to glucose or that require significantly higher levels of glucose to respond at normal levels).

As used herein, "heterologous DNA" or "heterologous nucleic acid" include DNA that does not occur naturally as part of the genome in which it is present or which is found in a location or locations in the genome that differs from that in which it occurs in nature. Heterologous DNA is not endogenous to the cell into which it is introduced, but has been obtained from another cell. Generally, although not necessarily, such DNA encodes RNA and proteins that are not normally produced by the cell in which it is expressed. Heterologous DNA may also be referred to as foreign DNA. Any DNA that one of skill in the art would recognize or consider as heterologous or foreign to the cell in which is expressed is herein encompassed by heterologous DNA.

The term "lineage committed cell" refers to a progenitor cell that is no longer pluripotent but has been induced to differentiate into a specific cell type, e.g., a pancreatic, hepatic or intestinal cell.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

The term "organ" refers to two or more adjacent layers of tissue, which layers of tissue maintain some form of cell-cell and/or cell-matrix interaction to form a microarchitecture.

The term "pancreas" is art recognized, and refers generally to a large, elongated, racemose gland situated transversely behind the stomach, between the spleen and duodenum. The pancreatic exocrine function, e.g., external secretion, provides a source of digestive enzymes. Indeed, "pancreatin" refers to a substance from the pancreas containing enzymes, principally amylase, protease, and lipase, which substance is used as a digestive aid. The exocrine portion is composed of several serous cells surrounding a lumen. These cells synthesize and secrete digestive enzymes such as trypsinogen, chymotrypsinogen, carboxypeptidase, ribonuclease, deoxyribonuclease, triacylglycerol lipase, phospholipase $A_2$, elastase, and amylase.

The term "pancreatic cell" refers to a cell which can produce a hormone or enzyme normally produced by a pancreatic cell, e.g., an at least partially differentiated α, β, δ, or PP cell, and a cell, e.g., a pancreatic precursor cell, which can develop into a cell which can produce a cells are characterized by the ability to produce glucagon and/or somatostatin. The pancreatic cells of the invention can also be cultured prior to administration to a subject under conditions which promote cell proliferation and differentiation. These conditions include culturing the cells to allow proliferation and confluence in vitro at which time the cells form pseudo islet-like aggregates or clusters and secrete insulin, glucagon, and somatostatin.

The term "pancreatic endocrine cell" refers to pancreatic cells (e.g., α, β, δ, or PP cells) that secrete pancreatic hormone(s). For example, a pancreatic endocrine cell of the invention may be a fetal β cell or a post-partem β cell which has been treated with PYY to produce insulin in response to glucose.

The term "pancreatic progenitor cell" refers to a cell which can differentiate into a cell of pancreatic lineage, e.g., a cell which can produce a hormone or enzyme normally produced by a pancreatic cell. For instance, a pancreatic progenitor cell may be caused to differentiate, at least partially, into an α, β, δ, or φ cell, or a cell of exocrine fate. Pancreatic progenitor cells can also be cultured prior to administration to a subject under conditions which promote cell proliferation and differentiation. These conditions include culturing the cells to allow proliferation and confluence in vitro at which time the cells can be made to form pseudo islet-like aggregates or clusters and secrete insulin, glucagon, and somatostatin. Methods of measuring cell proliferation are well known in the art and most commonly include determining DNA synthesis characteristic of cell replication. There are numerous methods in the art for measuring DNA synthesis, any of which may be used according to the invention. In an embodiment of the invention, DNA synthesis has been determined using a radioactive label ($^3$H-thymidine) or labeled nucleotide analogues (BrdU) for detection by immunofluorescence. However, in addition to measuring DNA and RNA synthesis, insulin secretion can be, and preferably will be, relied on as the basis for characterizing responsive fetal or progenitor cell populations.

The progenitor cells are characterized by an ability for self-regeneration in a culture medium and differentiation to pancreatic lineages. For instance, the progenitor cells can be isolated from pancreatic intralobular duct explants, e.g., isolated by biopsy, or are the cell culture progeny of such cells. The progenitor cells are inducible to differentiate into pancreatic islet cells, e.g., β islet cells, α islet cells, δ islet cells, or φ islet cells. Such pancreatic progenitor cells may be characterized in certain circumstances by the expression of one or more of: homeodomain type transcription factors such as STF-1; PAX gene(s) such as PAX6; PTF-1; hXBP-1; HNF genes(s); villin; tyrosine hydroxylase; insulin; glucagon; and/ or neuropeptide Y. Preferred progenitor cells will be of mammalian origin, e.g., cells isolated from a primate such as a human, from a miniature swine, or from a transgenic mammal, or are the cell culture progeny of such cells. Pancreatic ductal tissue may be isolated from a patient and subjected to the present method in order to provide a resulting culture of pancreatic progenitor cells (or differentiated cells derived therefrom). Gene replacement or other gene therapy is carried out ex vivo, and the isolated cells are transplanted back into the initial donor patient or into a second host patient.

In general, a culture system that allows reproducible expansion of pancreatic ductal epithelium while maintaining "stemmedness" and the ability to differentiate into endocrine and exocrine cells may be used. Pancreatic ductal epithelium is obtained, e.g., by explant or enzymatic digestion, and cultured to confluence. The confluent cell population is contacted with an agent, e.g., a trophic agent such as a growth factor, which causes differentiation of progenitor cells in the cultured population. Subsequently, progenitor cells from the explant that proliferate in response to the agent are isolated, such as by direct mechanical separation of newly emerging buds from the rest of the explant or by dissolution of all or a portion of the explant and subsequent isolation of the progenitor cell population. The agent may be Forskolin, Dibutyrl cAMP, Na-Butyrate, dexamethasone or cholera toxin or may be a growth factor such as IGF, TGF, FGF, EGF, HGF, hedgehog or VEGF or other member of the TGFβ superfamily, preferably of the DVR (dpp and vgl related) family, e.g., BMP2 and/or BMP7. Accordingly, another aspect of the present invention pertains to the progeny of the subject progenitor cells, e.g., those cells which have been derived from the cells of the initial explant culture. Such progeny can include subsequent generations of progenitor cells, as well as lineage committed cells generated by inducing differentiation of the subject progenitor cells after their isolation from the explant, e.g., induced in vitro.

Exemplary viable progenitor cells, and methods for isolating such cells from pancreatic ductal tissues are provided in the U.S. provisional patent application No. 60/119,576, which is incorporated herein by reference. Briefly, small ducts from rat pancreas are isolated after enzymatic digestion in collagenase A or collagenase H (Boehringer-Mannheim), washed and resuspended in HBSS (Ca/Mg free) and poured through a 500 u mesh to remove large particles and washed again. For older animals (over 2 weeks) the digest is resuspended in HBSS and placed in a 100 mm plate. The floating duct fragments are isolated manually with a pipette. For larger yields, pancreas from 2 week rat pups can be separated on Percoll (Pharmacia). The digested pancreas from are overlaid on a 40% Percoll solution and centrifuged at 1900 rpm/10 min. The duct fragments are located at the interface of buffer and Percoll at the top of the tube. This material is washed and placed in a 100 mm dish. Contaminating islets (very few) are removed manually. The fragments (including single cells) are washed again and plated for culture. Duct fragments are preferentially cultured in Iscoves modified DMEM with 5% FBS and penicillin/streptomycin. Ideally the cells are cultured for 5 days to achieve a confluent monolayer that can then be induced to differentiate. Confluence of the entire monolayer is not essential, differentiation can take place on any patch of confluent cells. The monolayer can be grown in the presence of EGF (10 ng/ml) or TGF-α (10 ng/ml) to enhance growth. Induction of differentiation is believed to be cAMP dependent. Agents which induce an increase in intracellular cAMP levels are anticipated to induce differentiation. Dexamethasone, cholera toxin, forskolin, dibutyrl cAMP and Na-Butyrate have all been tested and found to induce differentiation. Induction of differentiation is preferentially done in a single treatment for 48 hr. Progenitor cells appear over the course of the 48 hr treatment. Treatment can also be done for 24 hr resulting in progenitor cells.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. Various alignment algorithms and/or programs may be used, including FASTA, BLAST or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

As used herein, "phenotype" refers to the entire physical, biochemical, and physiological makeup of a cell, e.g., having any one trait or any group of traits.

The term "progenitor cell" refers to an undifferentiated cell which is capable of proliferation and giving rise to more progenitor cells having the ability to generate a large number of mother cells that can in turn give rise to differentiated, or differentiable daughter cells. As used herein, the term "progenitor cell" is also intended to encompass a cell which is sometimes referred to in the art as a "stem cell". In a preferred embodiment, the term "progenitor cell" refers to a generalized mother cell whose descendants (progeny) specialize, often in different directions, by differentiation, e.g., by acquiring completely individual characters, as occurs in progressive diversification of embryonic cells and tissues.

The term "subject" is intended to include mammals, particularly humans, susceptible to diseases characterized by insufficient insulin activity.

As used herein the term "substantially pure", with respect to progenitor cells, refers to a population of progenitor cells that is at least about 75%, preferably at least about 85%, more preferably at least about 90%, and most preferably at least about 95% pure, with respect to progenitor cells making up a total cell population. Recast, the term "substantially pure" refers to a population of progenitor cell of the present invention that contain fewer than about 20%, more preferably fewer than about 10%, most preferably fewer than about 5%, of lineage committed cells in the original unamplified and isolated population prior to subsequent culturing and amplification.

The term "tissue" refers to a group or layer of similarly specialized cells which together perform certain special functions.

The term "transplant" as used herein is intended to include cells, tissues or devices which are introduced into an animal and may be allogenic, autologous or xenogenic.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the protein.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Additional terms are defined where appropriate below.

(iii) Exemplary PYY Peptides and PYY Agonists

PYY is the predominant hormone of the pancreatic polypeptide family in developing mouse and rat pancreas. It is a member of the PP family of proteins, which also includes neuropeptide Y (NPY) and pancreatic polypeptide (PP). The sequence for human PYY is given by YPIKPEAPGEDASPEELNRYYASLRHYLNLVTRQRY (SEQ ID No: 2).

PYY inhibits intestinal motility and mesenteric blood flow to the gastrointestinal tract and pancreas, mediates gastric, pancreatic and intestinal exocrine secretion and stimulates net absorption (See, e.g., Laburthe (1990) *Trends Endocrinol. Metabol.* 1:168; Lundberg, J. M. et al. (1982) *Proc. Natl. Acad. Sci. USA* 79:4471-75; Suzuki, T. (1983) *Gastoenterology* 85:114-21; Pappas, T. N. (1985) *Am. J. Physiol.* 248: G118-G123; Cox et al. (1990) *Br. J. Pharmacol.* 101:247; Playford et al. (1990) *Cancer* 335:1555; McFayden et al. (1986) *Neuropeptides* 7:219). PYY has also been shown to inhibit the release of CCK, insulin, and glucagon in various animals (Lluis, F. et al. (1988) *Gastroenterology* 94:137-44; Guo, Y. S. et al. (1988) *Pancreas* 3:128-34; Botteher, G. et al. (1989) *Pancreas* 4:282-88; Guo, Y. S. et al. (1989) *Gastroenterology* 96:690-94; Greeley et al. (1988) *Am. J. Physiol.* 254:E513-17). PYY mRNA has been detected at e15 in rat and e10.5 in mouse pancreatic endocrine cells with peak PYY mRNA levels occurring in late gestation and remaining at lower levels in adult rats. (Krasinski, S. et al. (1991) *Mol. Endocrinol.* 5:433-40; Upchurch, B. H. (1994) *Development* 120:245-52). PYY cells appear earlier and are more numerous that NPY and PP cells, suggesting that PYY is the earliest expressed pancreatic hormone. (Jackerott, M. (1996) *J. Histochem. and Cytochem.* 44(8):809-17. In mouse, PYY is expressed in all islet cell types during development, suggesting that all four major cell types arise from a common PYY-producing multihormonal progenitor cell. (Myrsén-Axcrona, supra; Upchurch et al., supra). For example, PYY, insulin and glucagon are present in the same islet cells at early embryonic stages (e12-e15) but is restricted to islet non-β cells (mainly glucagon-containing cells) after the formation of separate populations of insulin- and glucagon-containing cells (e16-P0). (Myrsén-Axcrona et al., supra). These findings suggest that insulin-containing cells differentiate from the cells co-expressing glucagon and PYY. (Myrsén-Axcrona et al., supra).

The subject methods can be carried out using native, purified peptide YY or recombinant peptide YY, or fragments thereof, as well as peptidomimetics thereof. Peptide tyrosine tyrosine or peptide YY ("PYY") is a 36 amino acid residue peptide amide isolated originally from porcine intestine and primarily localized in the mucosal endocrine cells of the distal intestine, and also produced in the proximal intestine and the pancreas. (Tatemotu et al. (1982) *Proc. Natl. Acad. Sci.* 79:2514; Aponte, G. W. et al. (1989) *FASEB J.* 3:1949-55). Homologs and analogs of PYY can be generated by mutagenesis, such as by discrete point mutation(s), or by truncation. For instance, mutation can give rise to homologs which retain substantially the same, or merely a subset, of the biological activity of PYY. Alternatively, antagonistic forms of the protein can be generated which are able to inhibit the function of the naturally occurring form of PYY, such as by competitively binding to a cognate receptor of PYY, thus blocking signal transduction. In addition, agonistic forms of PYY may be generated which are constitutively active. Thus, PYY and homologs thereof may be either positive or negative regulators of glucose responsivity in pancreatic islets or β cells.

Human PYY and fragments thereof can be purchased commercially (Bachem California 1993-1994 Catalogue, Torrance, Calif.; Sigma peptides and amino acids 1994 Catalogue, St. Louis, Miss.). PYY analogs and mimetics may also be synthesized by many techniques that are known to those skilled in the peptide art. A summary of the many techniques available may be found in Solid Phase Peptide Synthesis $2^{nd}$ ed. (Stewart, J. M. and Young, J. D., Pierce Chemical Company, Rockford, Ill. 1984). Other PYY analogs can be prepared by making appropriate modifications, within the ability of a person of ordinary skill in the art.

In general, polypeptides referred to herein as having an activity (e.g., are "bioactive") of PYY are defined as polypeptides which include an amino acid sequence corresponding (e.g., identical or homologous) to all or a portion of the amino acid sequence of PYY and which mimic or antagonize all or a portion of the biological/biochemical activities of a naturally occurring PYY protein. Such biological activity includes the induction or enhancement of glucose responsivity as demonstrated by induced or increased insulin production and other indicia of β cell differentiation, such as, for example, homeodomain type transcription factors such as STF-1; PAX gene(s) such as PAX6; PTF-1; hXBP-1; HNF genes(s); villin; tyrosine hydroxylase; insulin; glucagon; and/or Neuropeptide Y.

The bioactivity of a PYY analog may also include the ability to alter the transcriptional rate of a gene as, for example, a downstream component of a signal transduction cascade initiated by the interaction of a PYY analog with its cognate receptor.

Other biological activities of PYY Therapeutics are described herein or will be reasonably apparent to those skilled in the art.

A PYY polypeptide which represents a portion of the full-length polypeptide, can be either an agonist (e.g., mimics or enhances), or alternatively, an antagonist of a biological activity of a naturally occurring form of the protein, e.g., the polypeptide is able to modulate differentiation and/or glucose responsiveness to authentic PYY proteins. Homologs of the subject PYY proteins include versions of the protein which are resistant to proteolytic cleavage, as for example, due to mutations which alter potential cleavage sequences or which inactivate an enzymatic activity associated with the protein.

The PYY polypeptides of the present invention which represent portions of the full-length polypeptides, can be glycosylated, or conversely, by choice of the expression system or by modification of the protein sequence to preclude glycosylation, reduced carbohydrate analogs can also be provided. Glycosylated forms include derivatization with glycosaminoglycan chains.

The subject proteins can also be provided as chimeric molecules, such as in the form of fusion proteins. For instance, the PYY protein can be provided as a recombinant fusion protein which includes a second polypeptide portion, e.g., a second polypeptide having an amino acid sequence unrelated to PYY, e.g., the second polypeptide portion is glutathione-S-transferase, e.g., the second polypeptide portion is an enzymatic activity such as alkaline phosphatase, e.g., the second polypeptide-portion is an epitope tag.

Analogs of PYY have been reported that emulate and enhance the duration, effect, biological activity and selectivity of the natural peptide in the treatment of pancreatic tumors (See U.S. Ser. No. 5,574,010, incorporated herein by reference).

(iv) Exemplary Uses of PYY Therapeutics

In one aspect, the present invention provides therapeutic methods involving the use of the pancreatic cell cultures of the present invention. For example, the present invention provides a method of altering blood sugar levels comprising administering to an animal a cell culture of pancreatic endocrine cells which have been generated by the present method. The cell culture used for altering blood sugar levels may be a primary cell culture of pancreatic endocrine cells, or a serially passaged culture thereof. The cultured pancreatic endocrine cells of the present invention include β cells that secrete insulin in response to glucose concentration.

In certain embodiments, the subject method utilizes an isolated population of pancreatic cells obtained from an embryo (preferably of a non-human mammal that has been "humanized") at a developmental stage of about the equivalent of day e21 of gestation. Pancreatic cells obtained from embryos can be cultured, e.g., as a monolayer of adherent non-insulin secreting cells in the presence of a PYY therapeutic. When these cells are allowed to reach confluence, they form islet-like aggregates or clusters and begin to secrete pancreatic hormones, such as insulin, glucagon, and somatostatin, and enzymes. At this point, such aggregates can be isolated, pooled, and administered to a recipient subject wherein they secrete insulin. Preferably, about 100,000 to 500,000 aggregates, each of which contains about 300 to 500 cells, can be used to treat one human. In humans, it has been demonstrated that 6-12 week fetuses do not respond to glucose but can be induced to produce insulin in a monophasic manner between 17 and 20 weeks but that this response is weak (1.6 fold). Biphasic secretion of insulin is achieved after birth, between 26 and 44 weeks. (Otonkoski T, et al. *Diabetes* 1988 March 37(3):286-91). This suggests that the human fetal pancreas is already responsive to glucose during the first half of gestation, but the biphasic insulin release does not start to mature until the postnatal phase. The method of altering blood sugar levels can also be accomplished using cultured pancreatic endocrine cells in a tissue-like form. Such cultured pancreatic endocrine cells, either as individual a cells or in combination with other cell types, can form coherent aggregates spontaneously or by culturing techniques known in the art. Such coherent aggregates are termed "pseudoislets" herein. Preferably, pseudoislets are embedded in a suitable biocompatable matrix, such as collagen, using methods known in the art. The cultured pancreatic endocrine cells also may be formed into coherent aggregates by co-incubation with a suitable biocompatable material, such as collagen, whereby the cells are in the form of free suspensions prior to the co-incubation. The coherent aggregate of cells formed by either method is termed a "pseudotissue." Pseudotissues form a biologically compatible graft that can be implanted into a mammal, and therein function to alter blood sugar levels.

Primary, secondary and subsequent, or clonal cultures of pancreatic endocrine cells, or combinations thereof prepared according to the methods described herein, and exemplified below, may be used in such pseudotissues. The method involves grafting pancreatic endocrine cells as a pseudotissue, for example, into a mammal where the pseudotissue becomes vascularized and responds to the blood glucose levels in the host mammal by secreting insulin when the blood glucose levels attain a sufficiently high level. Vascularization of the pseudotissue appears to be important in that in those experiments where the pseudotissue did not become vascularized, blood sugar levels were not regulated. Similarly, delayed vascularization of a pseudotissue appeared to impair the ability of the pseudotissue to regulate blood sugar levels.

In other embodiments, the present invention is directed to a method of providing a glucose-responsive insulin-secreting capability to a mammal in need of such capability. The method includes generally implanting engineered cells which secrete insulin in response to glucose into such a mammal. It is proposed by the inventor that techniques presently in use for the implantation of islets will be applicable to implantation of cells engineered in accordance with the present invention. One method involves the encapsulation of engineered cells in a biocompatible coating. In this approach, cells are entrapped in a capsular coating that protects the encapsulated cells from immunological responses, and also serves to prevent uncontrolled proliferation of clonal engineered cells. A preferred encapsulation technique involves encapsulation with alginate-polylysine-alginate. Capsules made employing this technique generally contain several hundred cells and have a diameter of approximately 1 mm.

An alternative approach is to seed Amicon fibers with engineered cells. The cells become enmeshed in the fibers, which are semipermeable, and are thus protected in a manner similar to the micro encapsulates. (Altman, et al., 1986).

After successful encapsulation or fiber seeding, the cells, generally approximately 1,000-10,000, may be implanted intraperitoneally, usually by injection into the peritoneal cavity through a large gauge needle (23 gauge).

A variety of other encapsulation technologies have been developed that are proposed by the present inventor will be applicable to the practice of the present invention (see, e.g., Lacy, et al. (1991) *Science* 254:1782-84, and Sullivan, et al. (1991) *Science* 252:718-21; WO 9110470; WO 9110425; WO 9015637; WO 9002580; U.S. Pat. No. 5,011,472; U.S. Pat. No. 4,892,538; WO 8901967, each of the foregoing being incorporated by reference). The company Cytotherapeutics has developed encapsulation technologies that are now commercially available that will likely be of use in the application of the present invention. A vascular device has also been developed by Biohybrid, of Shrewsbury, Mass., that may have application to the technology of the present invention.

In regard to implantation methods which may be employed to provide a glucose-responsive insulin-secreting capability to a mammal, it is contemplated that particular advantages may be found in the methods recently described by Lacy, et al., supra; Sullivan, et al., supra, each incorporated herein by reference. These concern, firstly, the subcutaneous xenograft of encapsulated islets, and secondly, the long-term implantation of islet tissue in an "artificial pancreas" which may be connected to the vascular system as an arteriovenous shunt. These implantation methods may be advantageously adapted for use with the present invention by employing engineered cells, as disclosed herein, in the place of the "islet tissue" of the prior art methods.

Further important embodiments concern methods of using the engineered cells of the present invention in the production of insulin, and particularly, in the production of human insulin which can be used in the treatment of IDDM. In certain aspects, the engineered artificial β cells are grown in culture and then contacted with a buffer containing glucose, thus stimulating the cells to produce and secrete insulin which can be collected and purified from the surrounding media. For use in connection with this aspect of the present invention, CTG-6 engineered cells are contemplated to be of particular use, but any cell prepared to secrete insulin in response to glucose may be employed. Still further aspects of the invention include methods of treating diseases or other disorders characterized by insufficient insulin activity in a subject, particularly a human subject. These methods include administering to a subject, a PYY pharmaceutical and an isolated population of pancreatic cells including insulin-producing cells (e.g., .β cells) or having the ability to differentiate to form insulin-secreting cells after administration to the subject. The terms "introduction", "administration", and "transplantation" are used interchangeably herein to refer to delivery of cells to a subject by a method or route which delivers the cells to a desired location. The term "treating" as used herein includes reducing or alleviating at least one adverse effect or symptom, e.g., absolute or relative insulin deficiency, fasting hyperglycemia, glycosuria, development of atherosclerosis, microangiopathy, nephropathy, and neuropathy, of diseases characterized by insufficient insulin activity. As used herein, the phrase "diseases characterized by insufficient insulin activity" include diseases in which there is an abnormal utilization of glucose due to abnormal insulin function. Abnormal insulin function includes any abnormality or impairment in insulin production, e.g., expression and/or transport through cellular organelles, such as insulin deficiency resulting from, for example, loss of cells as in IDDM (Type I diabetes), secretion, such as impairment of insulin secretory responses as in NIDDM (Type II diabetes), form of the insulin molecule itself, e.g., primary, secondary or tertiary structure, effects of insulin on target cells, e.g., insulin-resistance in bodily tissues, e.g., peripheral tissues, and responses of target cells to insulin. See Braunwald, E. et al. eds. (1987) *Harrison's Principles of Internal Medicine*, Eleventh Edition, McGraw-Hill Book Company, New York, pp. 1778-97; Robbins, S. L. et al. (1984) *Pathologic Basis of Disease,* 3.sup.rd Edition, W. B. Saunders Company, Philadelphia, p. 972 for further descriptions of abnormal insulin activity in IDDM and NIDDM and other forms of diabetes.

There are various pharmacological approaches to improving glucose homeostasis, but those currently used in clinical practice either do not succeed in restoring normoglycaemia in most patients or fail after a variable period of time. (Scheen, A. J. (1997) *Drugs* 54(3):355-68). Four classes of drugs are currently used. Sulphonylureas, biguanides (metformin), alpha-glucosidase inhibitors (acarbose) and insulin. Insulin therapy may be required, especially in the later stages of the disease, to produce control of hyperglycemia in an attempt to minimize complications of the disease. The most effective treatment of type II diabetes has been the alpha-glucosidase inhibitor, acarbose, which reduces postprandial glucose levels by retarding digestion of complex carbohydrates in the gut. Other metabolically active drugs have proven too toxic. Alternatively, sulphonylureas lower hyperglycaemia by increasing insulin secretion and potentiating insulin action on the liver and peripheral tissues. Drugs such as the thiazolidinediones (e.g., troglitazone, pioglitazone, darglitazone and YM268) enhance insulin action (i.e., are "insulin-sensitizing").

Alternatively, although it is possible to transplant the human pancreas, the shortage of donors and problems of immune rejection limit this procedure to selected patients. β-cell transplantation has been accomplished successfully in humans, but the large number of β-cells required and immune rejection have been obstacles. Effective and economical treatments for are therefore lacking.

The pancreatic cells are administered to the subject by any appropriate route which results in delivery of the cells to a desired location in the subject where the cells can proliferate and secrete a pancreatic hormone, e.g., insulin, or enzyme. Preferred locations for pancreatic cell administration include those which rapidly vascularize. Common methods of administering pancreatic cells to subjects, particularly human subjects, include implantation of cells in a pouch of omentum (Yoneda, K. et al. (1989) *Diabetes* 38 (Suppl. 1):213-216), intraperitoneal injection of the cells, (Wahoff, D. C. et al. (1994) *Transplant. Proc.* 26:804), implantation of the cells under the kidney capsule of the subject (See, e.g., Liu, X. et al. (1991) *Diabetes* 40:858-866; Korsgren, O. et al. (1988) *Transplantation* 45(3):509-514; Simeonovic, D. J. et al. (1982) *Aust. J. Exp. Biol. Med. Sci.* 60:383), and intravenous injection of the cells into, for example, the portal vein (Braesch, M. K. et al. (1992) *Transplant. Proc.* 24(2):679-680; Groth, C. G. et al. (1992) *Transplant. Proc.* 24(3):972-973). To facilitate transplantation of the pancreatic cells under the kidney capsule, the cells can be embedded in a plasma clot prepared from, e.g., plasma from the recipient subject (Simeonovic, D. J. et al. (1982) *Aust. J Exp. Biol. Med. Sci.* 60:383) or a collagen matrix. Cells can be administered in a pharmaceutically acceptable carrier or diluent.

(v) Pharmaceutical Preparations

While it is possible for PYY or a PYY agonist or antagonist or cellular compositions to be administered as pure or substantially pure compounds/compositions, it is preferable that they be administered as pharmaceutical formulations or preparations. The formulations to be used in the present invention, for both humans and animals, include PYY, PYY agonist or antagonist or cellular compositions, together with one or more pharmaceutically acceptable carriers therefor, and optionally other therapeutic ingredients.

The carrier must be "acceptable" in the sense of being compatible with the active ingredient(s) of the formulation (and preferably, capable of stabilizing peptides) and not deleterious to the subject to be treated.

The formulations may conveniently be presented in unit dosage form and may be prepared by any of the methods well known in the art of pharmacy. All methods include the step of bringing the active ingredient(s) into association with the carrier which constitutes one or more accessory ingredients.

The present invention relates to pharmaceutical compositions of PYY Therapeutics or cellular compositions, and their uses in treating and/or preventing disorders which can be improved by altering the homeostasis of peptide hormones. In a preferred embodiment, the inhibitors have hypoglycemic and anti-diabetic activities, and can be used in the treatment of disorders marked by aberrant glucose metabolism, including glucose storage. In particular embodiments, the compositions of the subject methods are useful as insulinotropic agents, or to potentiate the insulinotropic effects of such molecules as GLP-1. In this regard, the present method can be useful for the treatment and/or prophylaxis of a variety of disorders, including one or more of: hyperlipemia, hyperglycemia, obesity, glucose tolerance insufficiency, insulin resistance and diabetic complications.

PYY Therapeutics or cellular compositions can be administered in various forms, depending on the disorder to be treated and the age, condition and body weight of the patient, as is well known in the art. For example, where the compounds are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eye drops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses.

Glucose metabolism can be altered, and symptoms associated with type II diabetes can be decreased or eliminated, in accordance with a "timed" administration of a PYY Therapeutic wherein one or more appropriate indices for glucose metabolism and/or type II diabetes can be used to assess effectiveness of the treatment (including dosage and/or timing): e.g., glucose tolerance, glucose level, insulin level, insulin sensitivity or glycosylated hemoglobin.

An effective time for administering a PYY Therapeutic needs to be identified. This can be accomplished by routine experiment as described below, using one or more groups of animals (preferably at least 5 animals per group). In animals, insulinotropic activity by PYY treatment can be assessed by administering a PYY Therapeutic at a particular time of day and measuring the effect of the administration (if any) by measuring one or more indices associated with glucose metabolism, preferably insulin release, and comparing the post-treatment values of these indices to the values of the same indices prior to treatment, or to control treatments.

The precise time of administration and/or amount of a PYY Therapeutic that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

While the subject is being treated, glucose metabolism is monitored by measuring one or more of the relevant indices at predetermined times during a 24-hour period. Treatment (amounts, times of administration and type of medication) may be adjusted (optimized) according to the results of such monitoring. The patient is periodically re-evaluated to determine extent of improvement by measuring the same parameters, the first such re-evaluation typically occurring at the end of four weeks from the onset of therapy, and subsequent re-evaluations occurring every 4 to 8 weeks during therapy and then every 3 months thereafter. Therapy may continue for several months or even years with six months being a typical length of therapy for humans.

Adjustments to the amount(s) of drug(s) administered and possibly to the time of administration may be made based on these re-evaluations. For example, if after 4 weeks of treatment one of the metabolic indices has not improved but at least one other one has, the dose could be increased by ⅓ without changing the time of administration.

Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

The phrase "therapeutically-effective amount" as used herein means that amount of, e.g., a PYY Therapeutic, which is effective for producing some desired therapeutic effect by enhancing, for example, the glucose responsiveness of pancreatic β cells at a reasonable benefit/risk ratio applicable to any medical treatment.

The phrase "pharmaceutically acceptable" is employed herein to refer to those PYY, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of a PYY Therapeutic. These salts can be prepared in situ during the final isolation and purification of the PYY Therapeutic, or by separately reacting a purified PYY Therapeutic in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate maleate, fumarate, succinate, tartrate, naphthylate, mesylate, glucoheptonate, lactobionate, and laurylsulphonate salts and the like. (See, e.g., Berge et al. (1977) J. Pharm. Sci. 66:1-19)

In other cases, the PYY useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of a PYY Therapeutic. These salts can likewise be prepared in situ during the final isolation and purification of the PYY Therapeutic, or by separately reacting the purified PYY Therapeutic in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, e.g., Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a PYY Therapeutic with the carrier and, optionally, one or more accessory ingredients. In general, the formulations are prepared by uniformly and intimately bringing into association a PYY Therapeutic with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a PYY Therapeutic as an active ingredient. A compound may also be administered as a bolus, electuary or paste.

In solid dosage forms for oral administration (e.g., capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active PYY Therapeutics or cellular compositions may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more PYY Therapeutics with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of a PYY Therapeutic include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to PYY Therapeutic, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a PYY Therapeutic, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

PYY Therapeutics can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a PYY Therapeutic to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise a PYY Therapeutic in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (e.g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of a PYY Therapeutic or in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When a PYY Therapeutic or cellular compositions is administered as a pharmaceutical, to humans and animals, it can be given per se or as a pharmaceutical composition containing, for example, 0.1 to 99.5% (more preferably, 0.5 to 90%) of active ingredient in combination with a pharmaceutically acceptable carrier.

The preparations of agents may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, infraorbital, intra cardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a PYY Therapeutic, drug or other material other than directly into the central nervous system, such that it enters the patient's system and, thus, is subject to metabolism and other like processes, for example, subcutaneous administration.

A PYY Therapeutic may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, a PYY Therapeutic which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

(vi) Conjoint Administration

Another aspect of the invention provides a conjoint therapy wherein one or more other therapeutic agents are administered with a PYY Therapeutic or cellular compositions. Such conjoint treatment may be achieved by way of the simultaneous, sequential or separate dosing of the individual components of the treatment.

In one embodiment, a PYY Therapeutic or cellular compositions may be administered alone or in combination with other agents that augments the biological activity of PYY, the biological effect of PYY or to lessen any possible side-effects. For example, WO 9511689 describes the use of dipeptidylpeptidase inhibitors, such as inhibitors of dipeptidylpeptidase IV (DPIV) enzyme, which are able to inhibit the proteolysis of PYY, thereby increasing PYY's plasma half-life. Thus, in a preferred embodiment, a PYY Therapeutic may be conjointly administered with a dipeptidylpeptidase inhibitor.

In another illustrative embodiment, a PYY Therapeutic or cellular compositions can be conjointly administered with an M1 receptor antagonist. Cholinergic agents are potent modulators of insulin release that act via muscarinic receptors. Moreover, the use of such agents can have the added benefit of decreasing cholesterol levels, while increasing HDL levels. Suitable muscarinic receptor antagonists include substances that directly or indirectly block activation of muscarinic cholinergic receptors. Preferably, such substances are selective (or are used in amounts that promote such selectivity) for the M1 receptor. Nonlimiting examples include quaternary amines (e.g., methantheline, ipratropium, and propantheline), tertiary amines (e.g., as dicyclomine, scopolamine) and tricyclic amines (e.g., telenzepine). Pirenzepine and methyl scopolamine are preferred. Other suitable muscarinic receptor antagonists include benztropine (commercially available as COGENTIN from Merck), hexahydro-sila-difenilol hydrochloride (HHSID hydrochloride disclosed in Lambrecht, et al. (1989) *Trends in Pharmacol. Sci.* 110(Suppl):60; (+/−)-3-quinuclidinyl xanthene-9-carboxylate hemioxalate (QNX-hemioxalate; Birdsall, et al. (1983) *Trends in Pharmacol. Sci.* 4:459; telenzepine dihydrochloride (Coruzzi, et al. (1989) *Arch. Int. Pharmacodyn. Ther.* 302:232; and Kawashima, et al. (1990) *Gen. Pharmacol.* 21:17) and atropine. The dosages of such muscarinic receptor antagonists will be generally subject to optimization as outlined above. In the case of lipid metabolism disorders, dosage optimization may be necessary independently of whether administration is timed by reference to the lipid metabolism responsiveness window or not.

In terms of regulating insulin and lipid metabolism and reducing the foregoing disorders, a PYY Therapeutic or cellular compositions may also act synergistically with prolactin inhibitors such as d2 dopamine agonists (e.g., bromocriptine). Accordingly, the subject method can include the conjoint administration of such prolactin inhibitors as prolactin-inhibiting ergo alkaloids and prolactin-inhibiting dopamine agonists. Examples of suitable compounds include 2-bromo-alpha-ergocriptine, 6-methyl-8 beta-carbobenzyloxyaminoethyl-10-alpha-ergoline, 8-acylaminoergolines, 6-methyl-8-alpha-(N-acyl)amino-9ergoline, 6-methyl-8-alpha-(N-phenylacetyl)amino-9-ergoline, ergocornine, 9,10-dihydroergocornine, D-2-halo-6-alkyl-8-substituted ergolines, D-2-bromo-6-methyl-8-cyanomethylergoline, carbidopa, benserazide and other dopadecarboxylase inhibitors, L-dopa, dopamine and non toxic salts thereof.

Agonists such as Ach, cholecystokinin (CCK) or bombesin bind to cell surface receptors that are coupled via the heterotrimeric G protein $G_q$ to phospholipase C (PLC). Receptor occupancy activates PLC with the consequent generation of $IP_3$ and DAG by the hydrolysis of $PIP_3$. $Ca^{2+}$ released from the endoplasmic reticulum by $IP_3$ may be important for activation of the α and β isoforms of PKC and DAG can activate the α, β, δ and ε isoforms of PKC.

PYY Therapeutic or cellular compositions used according to the invention can also be used conjointly with agents acting on the ATP-dependent potassium channel of the β-cells, such as glibenclamide, glipizide, gliclazide and AG-EE 623ZW. PYY or its analog or mimetic may also advantageously be applied in combination with other oral agents such as metformin and related compounds or glucosidase inhibitors as, for example, acarbose.

A PYY therapeutic or cellular compositions as described above may be administered conjointly with a secretin therapeutic. Secretin therapeutics, as disclosed in U.S. patent application Ser. No. 09/500,817 and PCT Application US00/03422, both of which are incorporated by reference, have been found to induce insulin-positive progenitor cells in pancreatic duct cultures. The term "secretin therapeutic" as used herein includes agents which emulate the activity of wild-type secretin (e.g., SEQ ID No. 2) or a derivative thereof having at least one bioactivity of the wild-type secretin, an analog, or derivative of secretin therapeutics. Included are secretin agonists and compounds such as dexamethasone, dibutyryl-cAMP, Na-butyrate, forskolin, and cholera toxin, which mimic certain aspects of secretin bioactivity, as well as prodrug forms of active secretin therapeutics, e.g., compounds which, under physiological conditions, e.g., in the stomach, in the bloodstream, etc., undergo a rearrangement, transformation, or reaction that results in a compound having increased secretin therapeutic or secretin agonist activity. A secretin therapeutic may further comprise a vector for transfecting a cell with a nucleic acid sequence, e.g., SEQ ID No. 1 or a fragment or variant thereof, encoding secretin or a bioactive fragment thereof, e.g., SEQ ID No. 2 or a fragment thereof. In preferred embodiments, a secretin therapeutic may be any compound, preferably secretin, an active fragment thereof, a peptidomimetic thereof, or a small organic molecule, which induces differentiation or proliferation of pancreatic ductal epithelial cells and/or increases the cellular concentration or expression of insulin in pancreatic ductal epithelial cells. In certain preferred embodiments, a secretin therapeutic is capable of binding and activating a receptor bound and activated by secretin, such as secretin receptor (e.g., SEQ ID No. 4, encoded by SEQ ID No. 3), and/or shares an activity with secretin that is inhibited by insulin. It has been found that secretin therapeutics also induce differentiation in ductal epithelial cells. For instance, it has been observed that insufficient levels of insulin allow full differentiation of the epithelial ductal cells to occur until the insulin levels have been restored. It has also been observed that increased levels of insulin block this inductive activity.

(vii) Detecting PYY Genotype

Another aspect of the present invention relates to diagnostic assays to assess the risk of a patient developing diabetes or other glucose metabolic disorder, and to determine the pathology of patients who have already been diagnosed with such disorders. In preferred embodiments, the regulation of PYY is monitored in order to identify patients at risk of developing type II diabetes.

In particular, the assay may assess a decrease in the level of PYY in the serum or other bodily fluid of the patient. Such decreases may be the result of, inter alia, a decrease in the level of expression or secretion of PYY, or a decrease in the serum half life of the protein. In other embodiments, the assay detects mutated PYY proteins, e.g., based on bioactivity or appearance or disappearance of an epitope, which may give rise to decreased activity, e.g., reduced receptor binding or loss or agonist activity. In still other embodiments, the assay detects abnormalities of the level of the PYY gene, e.g., point mutations such as base pair changes, additions or deletions to the coding sequence or transcriptional regulatory sequences.

Accordingly, the present method provides a method for determining if a subject is at risk for a disorder characterized by decreased glucose-sensing. In preferred embodiments, method can be generally characterized as comprising detecting, in a sample of cells from the subject, the presence or absence of a genetic lesion characterized by at least one of (i) an alteration affecting the integrity of a gene encoding a PYY protein, (ii) the mis-expression of the PYY gene, or (iii) aberrant modification of the PYY gene product. To illustrate, such genetic lesions can be detected by ascertaining the existence of at least one of (i) a deletion of one or more nucleotides from a PYY gene, (ii) an addition of one or more nucleotides to a PYY gene, (iii) a substitution of one or more nucleotides of a PYY gene, (iv) a gross chromosomal rearrangement of a PYY gene, (v) a gross alteration in the level of a messenger RNA transcript of a PYY gene, (vii) aberrant modification of a PYY gene, such as of the methylation pattern of the genomic DNA, (vii) the presence of a non-wild type splicing pattern of a messenger RNA transcript of a PYY gene, (viii) a non-wild type level of a PYY protein, (ix) allelic loss of the PYY gene, and (x) inappropriate post-translational modification of a PYY-protein. As set out below, the present invention provides a large number of assay techniques for detecting lesions in a PYY gene, and importantly, provides the ability to discern between different molecular causes underlying PYY-dependent aberrant cell growth, proliferation and/or differentiation. In one preferred embodiment, the assay is used to detect point mutations to the secretion signal sequence which eliminates the site of secretion of the mature PYY protein. For instance, the assay may detect a base pair change which gives rise to Thr (−17)→Asn or Thr (−16)→Pro.

Nucleic acid probes can be used to determine the PYY phenotype of cell and tissue samples, e.g., as a part of a diagnostic test kit for identifying cells or tissue which mis-express PYY, such as by measuring a level of a PYY-encoding nucleic acid in a sample of cells from a patient; e.g. detecting PYY mRNA levels or determining whether a genomic PYY gene has been mutated or deleted.

To illustrate, nucleotide probes can be generated from the subject PYY genes which facilitate histological screening of intact tissue and tissue samples for the presence (or absence) of PYY-encoding transcripts. Similar to the diagnostic uses of anti-PYY antibodies, infra, the use of probes directed to PYY messages, or to genomic PYY sequences, can be used for both predictive and therapeutic evaluation of allelic mutations which might be manifest in, for example, neoplastic or hyperplastic disorders (e.g. unwanted cell growth) or abnormal differentiation of tissue. Used in conjunction with immunoassays as described below, the oligonucleotide probes can help facilitate the determination of the molecular basis for a developmental disorder which may involve some abnormality associated with expression (or lack thereof) of a PYY protein. For instance, variation in polypeptide synthesis, post-translational modification, or half-life can be differentiated from a mutation in a coding sequence.

In an exemplary embodiment, there is provided a nucleic acid composition comprising a (purified) oligonucleotide probe including a region of nucleotide sequence which is capable of hybridizing to a sense or antisense sequence of a PYY gene, such as represented by SEQ ID No: 1, or naturally occurring mutants thereof, or 5' or 3' flanking sequences or intronic sequences naturally associated with the subject PYY gene or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1944) *PNAS* 91:360-364), the later of which can be particularly useful for detecting point mutations in the PYY gene. In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a PYY gene under conditions such that hybridization and amplification of the PYY gene (if present) occurs, and (iv) detecting the presence or absence of an amplification product, or detecting the size of the amplification product and comparing the length to a control sample.

In a preferred embodiment of the subject assay, mutations in a PYY gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the PYY gene and detect mutations by comparing the sequence of the sample PYY with the corresponding wild-type (control) sequence. Exemplary sequencing reactions include those based on techniques developed by Maxim and Gilbert (*Proc. Natl Acad Sci USA* (1977) 74:560) or Sanger (Sanger et al. (1977) *Proc. Nat. Acad. Sci* 74:5463). It is also contemplated that any of a variety of automated sequencing procedures may be utilized when performing the subject assays (*Biotechniques* (1995) 19:448), including by sequencing by mass spectrometry (see, for example PCT publication WO 94/16101; Cohen et al. (1996) *Adv Chromatogr* 36:127-162; and Griffin et al. (1993) *Appl Biochem Biotechnol* 38:147-159). It will be evident to one skilled in the art that, for certain embodiments, the occurrence of only one, two or three of the nucleic acid bases need be determined in the sequencing reaction. For instance, A-tract or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA heteroduplexes (Myers, et al. (1985) *Science* 230:1242). In general, the art technique of "mismatch cleavage" starts by providing heteroduplexes formed by hybridizing (labelled) RNA or DNA containing the wild-type PYY sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymod.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in PYY cDNAs obtained from samples of cells. For example, the mutY enzyme of *E. coli* cleaves A at G/A mismatches and the thymidine DNA glycoslase from HeLa cells cleaves T at G/T mismatches (Hsu et al. (1994) *Carcinogenesis* 15:1657-1662). According to an exemplary embodiment, a probe based on a PYY sequence, e.g., a wild-type PYY sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in PYY genes. For example, single strand conformation polymorphism (SSCP) may be used to detect differences in electrophoretic mobility between mutant and wild type nucleic acids (Orita et al. (1989) *Proc Natl. Acad. Sci USA* 86:2766, see also Cotton (1993) *Mutat Res* 285:125-144; and Hayashi (1992) *Genet Anal Tech Appl* 9:73-79). Single-stranded DNA fragments of sample and control PYY nucleic acids will be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotide hybridization techniques may be used to test one mutation per reaction when oligonucleotides are hybridized to PCR amplified target DNA or a number of different mutations when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238. In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In yet another exemplary embodiment, aberrant methylation patterns of a PYY gene can be detected by digesting genomic DNA from a patient sample with one or more restriction endonucleases that are sensitive to methylation and for which recognition sites exist in the PYY gene (including in the flanking and intronic sequences). See, for example, Buiting et al. (1994) *Human Mol Genet* 3:893-895. Digested DNA is separated by gel electrophoresis, and hybridized with probes derived from, for example, genomic or cDNA sequences. The methylation status of the PYY gene can be determined by comparison of the restriction pattern generated from the sample DNA with that for a standard of known methylation.

In still another embodiment, the level of a PYY protein can be detected by immunoassay. For instance, the serum samples can be obtained, and the level of a PYY protein present in the sample can be quantitated by standard immunoassay techniques.

In yet other embodiments, the subject assay can be designed to detect aberrant post-translational modification of the PYY protein, such as aberrant phosphorylation, prenylation, lipid modification, ubiquitination, and/or degradation. The assay can also be used to assess tissue localization of PYY.

According to the diagnostic and prognostic method of the present invention, alterations of the wild-type PYY locus which result in loss-of-function of PYY are detected. In addition, the method can be performed by detecting the wild-type PYY locus and confirming the lack of a predisposition to diabetes at the PYY locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues and are not inherited in the germline. The finding of PYY mutations can thus provide both diagnostic and prognostic information. A PYY allele which is not deleted (e.g., found on the sister chromosome to a chromosome carrying a PYY deletion) can be screened for other mutations, such as insertions, small deletions, and point mutations. Point mutational events may occur in regulatory regions, such as in the promoter of the gene, leading to loss or diminution of expression of the mRNA. Point mutations may also abolish proper RNA processing, leading to loss of expression of the PYY gene product, or to a decrease in mRNA stability or translation efficiency.

As set forth above, useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis LCR, and PCR-SSCP.

Continuing from the discussion above, there are several methods that can be used to detect DNA sequence variation. Direct DNA sequencing, either manual sequencing or automated fluorescent sequencing can detect sequence variation. For a gene as large as PYY, manual sequencing is not necessarily labor-intensive, and under optimal conditions, mutations in the coding sequence of a gene will rarely be missed. Another approach is the single-stranded conformation polymorphism assay (SSCA). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE), heteroduplex analysis (HA), and chemical mismatch cleavage (CMC). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. Once a mutation is known, an allele specific detection approach such as allele specific oligonucleotide (ASO) hybridization can be utilized to rapidly screen large numbers of other samples for that same mutation.

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of cancer cases, tumors, or both. Southern blots displaying hybridizing fragments (differing in length from control DNA when probed with sequences near or including the PYY locus) indicate a possible mutation. If restriction enzymes which produce very large restriction fragments are used, then pulsed field gel electrophoresis (PFGE) is employed.

Detection of point mutations may be accomplished by molecular cloning of the PYY allele(s) and sequencing the allele(s) using techniques well known in the art. Alternatively, the gene sequences can be amplified directly from a genomic DNA preparation using known techniques. The DNA sequence of the amplified sequences can then be determined.

There are many well known methods for a more complete, yet still indirect, test for confirming the presence of a susceptibility allele, including: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. For allele-specific PCR, primers are used which hybridize at their 3' ends to a particular PYY mutation. If the particular PYY mutation is not present, an amplification product is not observed. Amplification Refractory Mutation System (ARMS) can also be used, as disclosed in European Patent Application Publication No. 0332435. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment.

Such a method is particularly useful for screening relatives of an affected individual for the presence of the PYY mutation found in that individual. Other techniques for detecting insertions and deletions as known in the art can be used.

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type PYY gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the PYY mRNA or gene but can be a segment of either. If the riboprobe comprises only a segment of the PYY mRNA or gene, it will be desirable to use a number of these probes to screen the whole mRNA sequence for mismatches.

In similar fashion, DNA probes can be used to detect mismatches, through enzymatic or chemical cleavage. Alternatively, mismatches can be detected by shifts in the electrophoretic mobility of mismatched duplexes relative to matched duplexes. With either riboprobes or DNA probes, the cellular mRNA or DNA which might contain a mutation can be amplified using PCR (see below) before hybridization. Changes in DNA of the PYY gene can also be detected using Southern hybridization, especially if the changes are gross rearrangements, such as deletions and insertions.

DNA sequences of the PYY gene which have been amplified by use of PCR may also be screened using allele-specific probes. These probes are nucleic acid oligomers, each of which contains a region of the PYY gene sequence harboring a known mutation. For example, one oligomer may be about 30 nucleotides in length, corresponding to a portion of the PYY gene sequence. By use of a battery of such allele-specific probes, PCR amplification products can be screened to identify the presence of a previously identified mutation in the PYY gene. Hybridization of allele-specific probes with amplified PYY sequences can be performed, for example, on a nylon filter. Hybridization to a particular probe under stringent hybridization conditions indicates the presence of the same mutation in the tumor tissue as in the allele-specific probe.

The most definitive test for mutations in a candidate locus is to directly compare genomic PYY sequences from diabetic patients with those from a control population. Alternatively, one could sequence messenger RNA after amplification, e.g., by PCR, thereby eliminating the necessity of determining the exon structure of the candidate gene.

Mutations from diabetic patients falling outside the coding region of PYY can be detected by examining the non-coding regions, such as introns and regulatory sequences near or within the PYY gene. An early indication that mutations in noncoding regions are important may come from Northern blot experiments that reveal messenger RNA molecules of abnormal size or abundance in diabetic patients as compared to control individuals.

Alteration of PYY mRNA expression can be detected by any techniques known in the art. These include Northern blot analysis, PCR amplification and RNase protection. Diminished mRNA expression indicates an alteration of the wild-type PYY gene. Alteration of wild-type PYY genes can also be detected by screening for alteration of wild-type PYY protein. For example, monoclonal antibodies immunoreactive with PYY can be used to screen a tissue. Lack of cognate antigen would indicate a PYY mutation. Antibodies specific for products of mutant alleles could also be used to detect mutant PYY gene product. Such immunological assays can be done in any convenient formats known in the art. These include Western blots, immunohistochemical assays and ELISA assays. Any means for detecting an altered PYY protein can be used to detect alteration of wild-type PYY genes. Functional assays, such as protein binding determinations, can be used. In addition, assays can be used which detect PYY biochemical function. Finding a mutant PYY gene product indicates alteration of a wild-type PYY gene.

Mutant PYY genes or gene products can also be detected in other human body samples, such as serum, stool, urine and sputum. The same techniques discussed above for detection of mutant PYY genes or gene products in tissues can be applied to other body samples. Cancer cells are sloughed off from tumors and appear in such body samples. By screening such body samples, a simple early diagnosis can be achieved for many types of glucose metabolic disorders involving loss of pancreatic glucose sensing. In addition, the progress of chemotherapy or radiotherapy can be monitored more easily by testing such body samples for mutant PYY genes or gene products.

The primer pairs of the present invention are useful for determination of the nucleotide sequence of a particular PYY allele using PCR. The pairs of single-stranded DNA primers can be annealed to sequences within or surrounding the PYY gene on the chromosome in order to prime amplifying DNA synthesis of the PYY gene itself. A complete set of these primers allows synthesis of all of the nucleotides of the PYY gene coding sequences, i.e., the exons. The set of primers preferably allows synthesis of both intron and exon sequences. Allele-specific primers can also be used. Such primers anneal only to particular PYY mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from PYY sequences or sequences adjacent to PYY, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of the PYY open reading frame shown in SEQ ID NO:1, design of particular primers, in addition to those disclosed below, is well within the skill of the art.

(ix) Methods of Use

Nucleic Acid Diagnosis and Diagnostic Kits

In order to detect the presence of a PYY allele predisposing an individual to diabetes, a biological sample such as a blood sample or biopsy, is prepared and analyzed for the presence or absence of susceptibility alleles of PYY. In order to detect the presence of diabetes, the progression toward diabetes, or as a prognostic indicator, a biological sample is prepared and analyzed for the presence or absence of mutant alleles of PYY. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method can involve amplification of the relevant PYY sequences. In certain embodiments of the invention, the screening method involves a non-PCR based strategy for amplification, such as strand-displacement amplification (SDA) and the like. Such screening methods may include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for diabetes susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of the human chromosome including the PYY gene. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., supra and Sambrook et al., supra. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety.

As noted above, non-PCR based screening assays are also contemplated in this invention. An exemplary non-PCR based procedure hybridization of a nucleic acid probe (or an analog such as a methyl phosphonate backbone replacing the normal phosphodiester) to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$-$10^6$ increase in sensitivity.

Two-step label amplification methodologies are known in the art. These assays work on the principle that a small ligand (such as digoxigenin, biotin, or the like) is attached to a nucleic acid probe capable of specifically binding PYY. Exemplary probes can be developed on the basis of the sequence set forth in SEQ ID NO:1. Allele-specific probes are also contemplated within the scope of this example, and exemplary allele specific probes include probes encompassing the predisposing mutations resulting in loss of PYY secretions of a decrease in serum half life.

In one example, the small ligand attached to the nucleic acid probe is specifically recognized by an antibody-enzyme conjugate. In one embodiment of this example, digoxigenin is attached to the nucleic acid probe: Hybridization is detected by an antibody-alkaline phosphatase conjugate which turns over a chemiluminescent substrate. In a second example, the small ligand is recognized by a second ligand-enzyme conjugate that is capable of specifically complexing to the first ligand. A well known embodiment of this example is the biotin-avidin type of interactions.

It is also contemplated within the scope of this invention that the nucleic acid probe assays of this invention can employ a cocktail of nucleic acid probes capable of detecting PYY sequences. Thus, in one example to detect the presence of PYY in a cell sample, more than one probe complementary to PYY is employed and in particular the number of different probes is alternatively 2, 3, or 5 different nucleic acid probe sequences. In another example, to detect the presence of mutations in the PYY gene sequence in a patient, more than one probe complementary to PYY is employed where the cocktail includes probes capable of binding to the allele-specific mutations identified in populations of patients with alterations in PYY. In this embodiment, any number of probes can be used, and will preferably include probes corresponding to the major gene mutations identified as predisposing an individual to, e.g., a particular cancer.

EXEMPLIFICATION

Example 1

Islet Isolation and Culture

Intestine-derived hormone peptides including PP, NPY, NPK, PYY, secretin, GLP-1 and Bombesin were purchased from Sigma. Collagenase type XI was obtained from Sigma. RPMI 1640 culture medium and fetal bovine serum were obtained from Gibco. A radioimmunoassay kit containing anti-insulin antibody ([$^{125}$I]-RIA kit) was purchased from Linco, St Louis.

Figure 1:
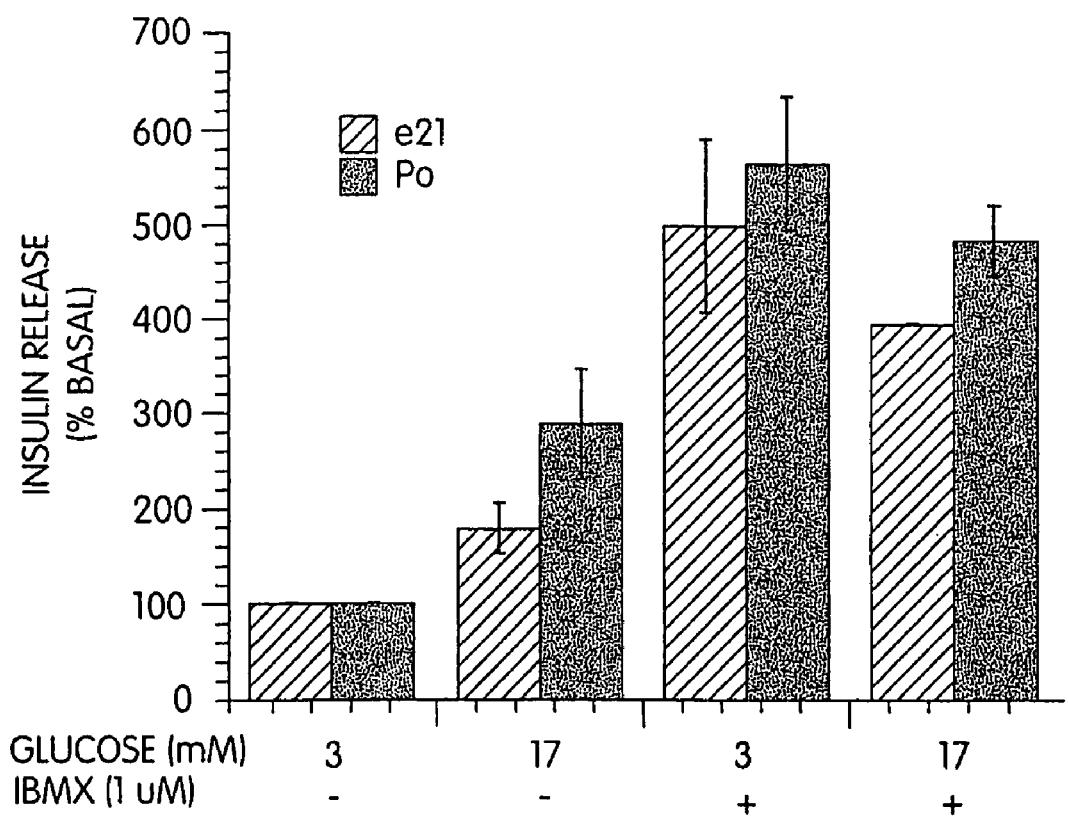
FIG. 1: Effect of IBMX on insulin release in e21/P0 pancreas.

Post-partem rat islets were obtained from P0-2 year old rats. Adult rat islets were obtained from 6-8 week old rats. Fetal rat islets were obtained as follows. Pregnant female rats were sacrificed on pregnancy day e21. Fetuses were removed from the uterus. 10-14 pancreata were dissected from each litter and washed twice in Hanks buffer. The pancreas were pooled, suspended in 6 ml 1 mg/ml collagenase (Type XI, Sigma) and incubated at 37° C. for 8-10 minutes with constant shaking. The digestion was stopped by adding 10 volumes of ice-cold Hanks buffer followed by three washes with Hanks buffer. The islets were then purified by Ficoll gradient and cultured in 10% fetal bovine serum (FBS)/RPMI medium with or without addition of 1 μM IBMX. At the end of five days, 20 islets were hand picked into each tube and assayed for static insulin release. Generally, islets were first washed with KRP buffer and then incubated with 1 ml of KRP buffer containing 3 mM (low) glucose for 30 minutes at 37° C. with constant shaking. After collecting the supernatant, the islets were then incubated with 17 mM (high) glucose for one hour at 37° C. The insulin released from low or high glucose stimulation were assayed by radioimmunoassay (RIA) using the [$^{125}$I]-RIA kit (see FIG. 1).

Example 2

IBMX Stimulated Calcium Influx in e21 Islets

Figure 2:
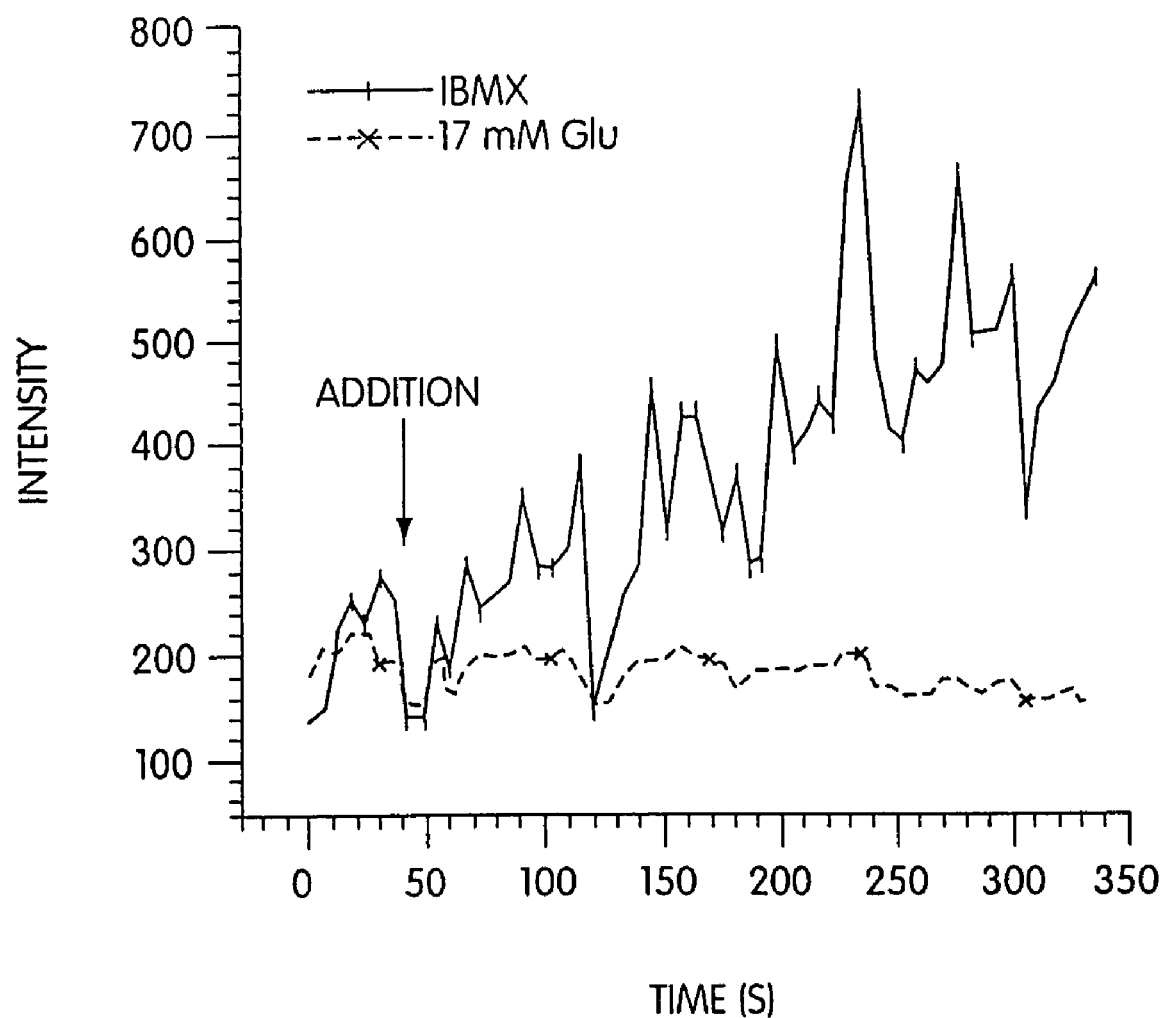
FIG. 2: IBMX stimulated calcium influx in e21 islets.

E21 islet were isolated and cultured according to Example 1. Islets were then treated with 17 mM glucose or 1 μM IBMX in 3 mM (low) glucose (FIG. 2). Non-glucose responsive e21 islets did not experience a rise in intracellular calcium influx upon the addition of high glucose. The addition of IBMX induced a calcium influx, suggesting that the mechanism of IBMX that stimulated insulin release in e21 islets also utilizes activation of calcium channels. This further suggests that the gain of glucose responsivity observed in P0 islets occurs upstream of the calcium channel.

Example 3

PYY Induces the Maturation of Fetal Islets

Figure 3A:
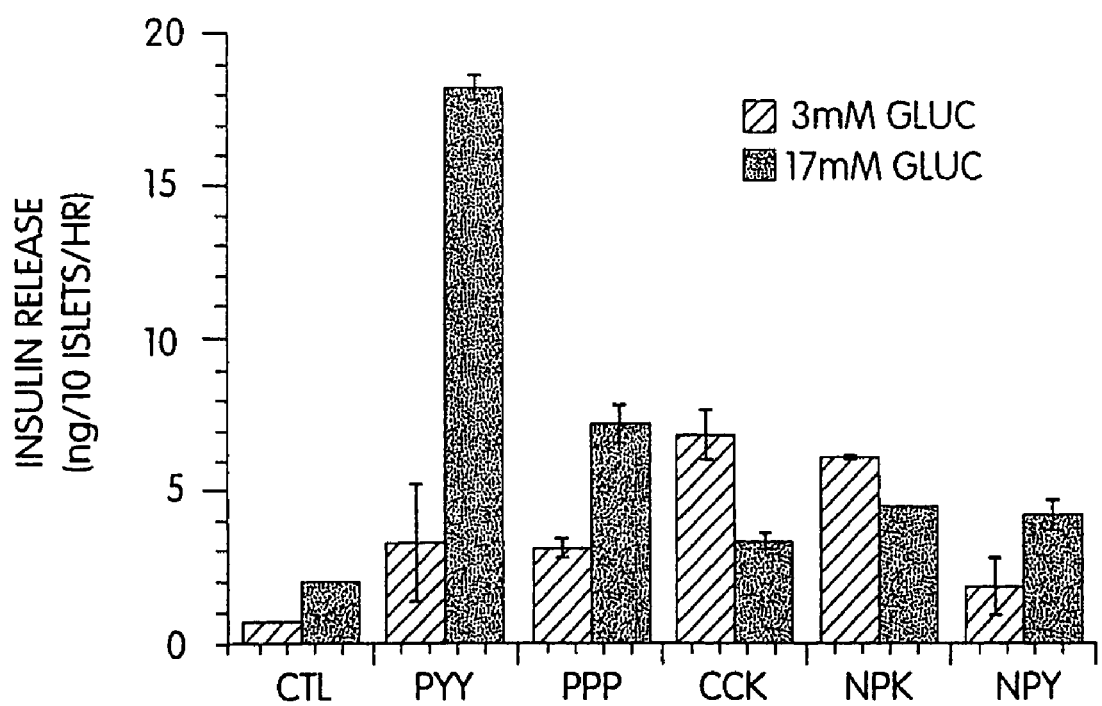
FIGS. 3A and 3B: PYY induces the maturation of fetal islets.
Figure 3B:
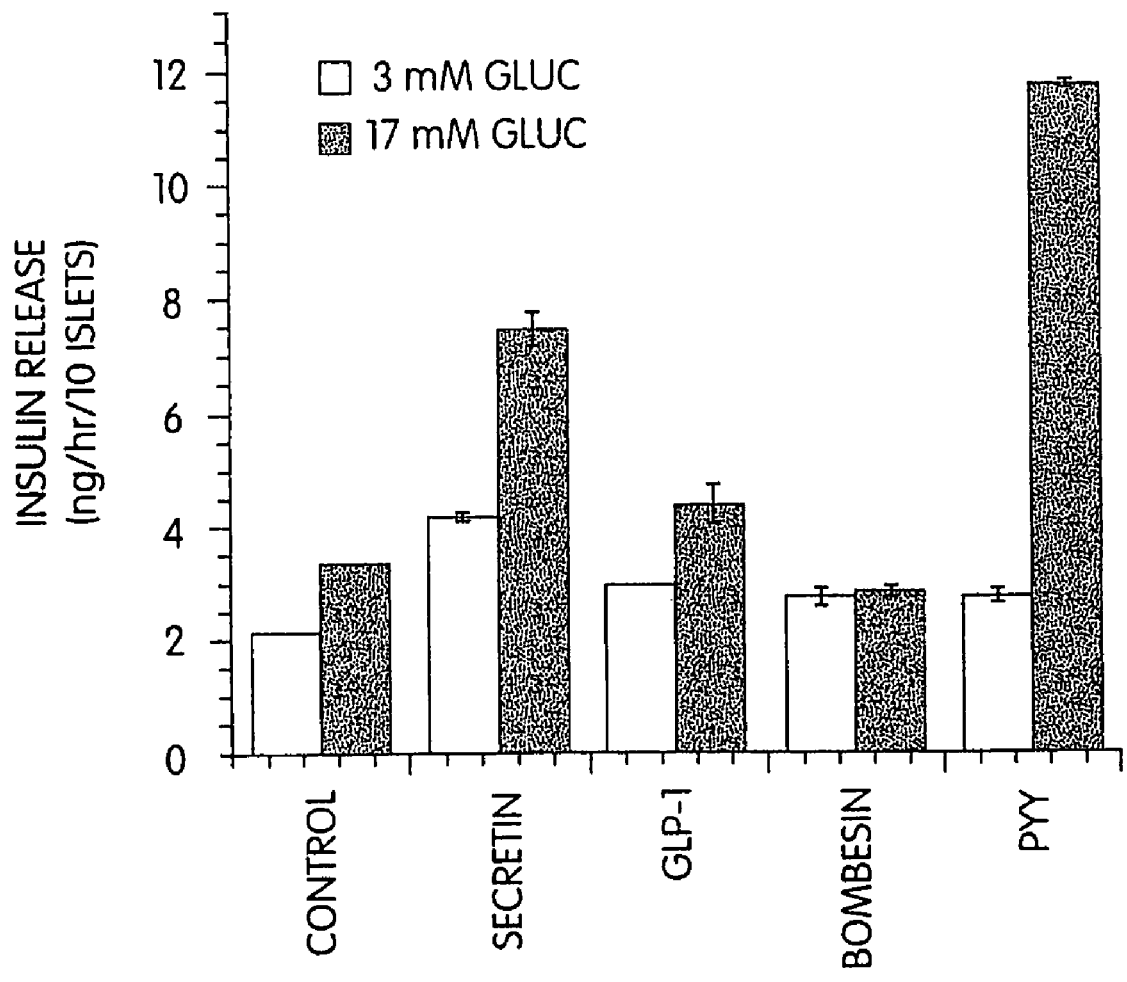

Fetal rat islets were isolated as in Example 1. E21 fetal islets were cultured for 5 days in the presence of 200 ng/ml PYY, PPP, CCK, NPK, NPY, Secretin, GLP-1 or Bombesin. Glucose-stimulated insulin release was then measured in each culture group (FIGS. 3A and 3B). PYY significantly stimulated the ability of the islets to respond to glucose by secreting insulin. Related peptides such as PPP and NPY, which share approximately 70% amino acid homology, did not stimulate gain of glucose responsivity.

Example 4

The Effect of PYY on e21 Islets is Time Dependent

Figure 4:
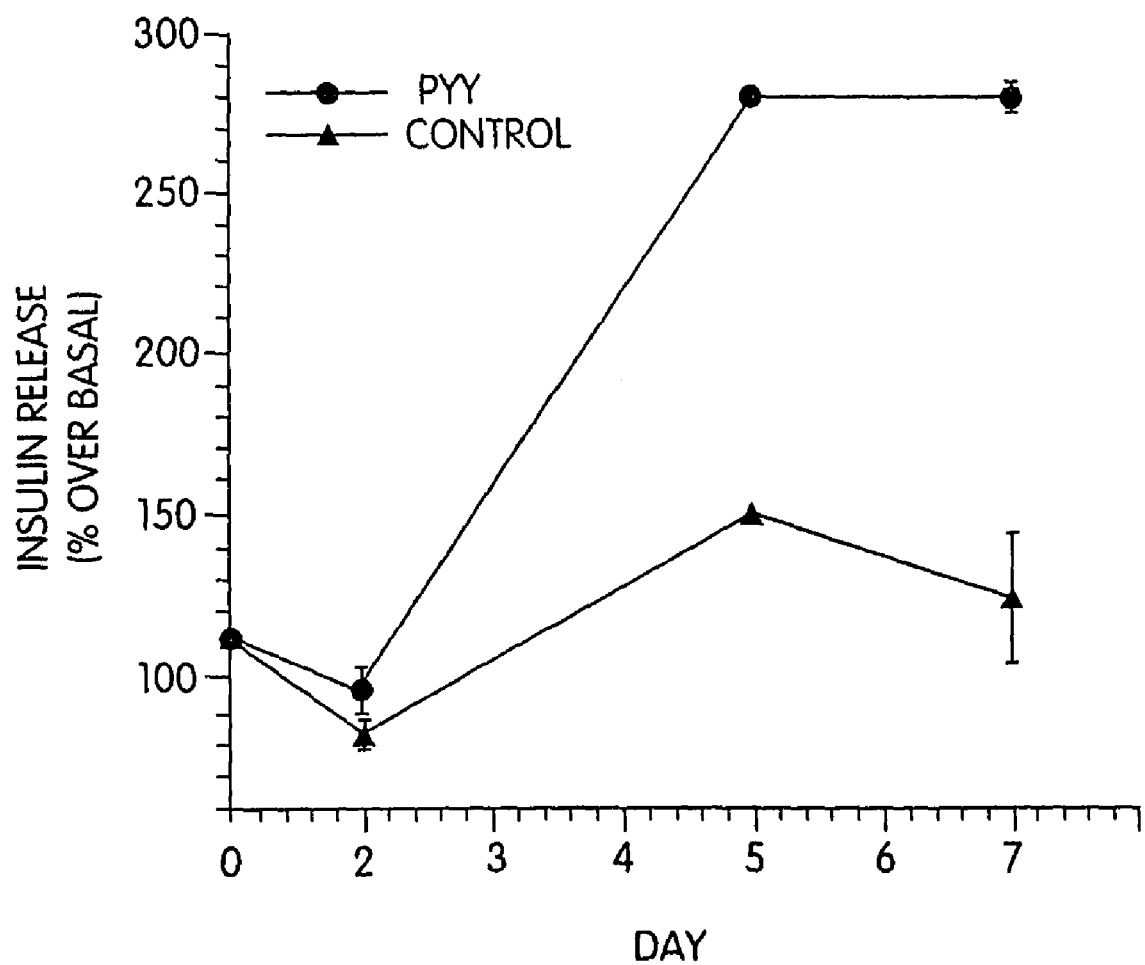
FIG. 4: The effect of PYY on e21 islets is time dependent.

Fetal rat islets were isolated as in Example 1. E21 islets were then cultured for 2, 5 or 7 days with 200 ng/ml PYY. Glucose-stimulated insulin release was then measured in each culture group (FIG. 4). The control group showed a slight gain of glucose responsivity after 5 days in culture compared to the time 0 and 2 day time points (triangles), as measured by insulin release. The addition of PYY for 5 days almost doubled the amount of insulin released in response to glucose in comparison to the control. This effect was maintained at the 7 day time point. Note that there was no effect of PYY on gain of glucose responsivity after 2 days of PYY incubation.

Example 5

The Dose Response of PYY Shows the Optimal Dose to be 200 ng/mL

Figure 5:
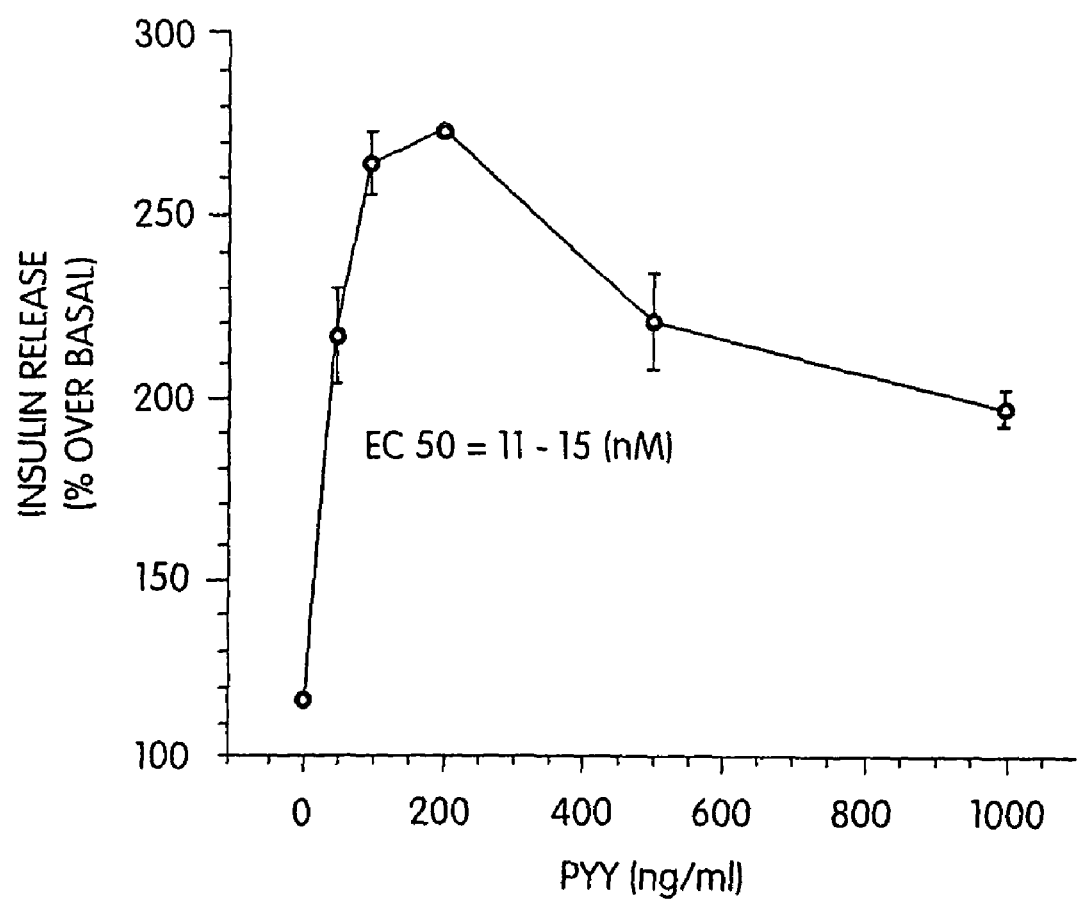
FIG. 5: The effect of PYY on e21 islets is dose dependent.

Fetal rat islets were isolated as in Example 1. PYY was added to e21 islets at 50, 100, 200, 500 and 1000 ng/ml for five days. Glucose-stimulated insulin release was then measured in each culture group (FIG. 5). The optimal effect of PYY was observed at 200 ng/ml, as measured by insulin release. There was diminished effect of PYY at 500 and 1000 ng/ml, the latter being observed previously in FIG. 5.

Example 6

PYY Effect on Adult Islets

Adult rat islets were isolate as in Example 1 and treated over a period of 16 days with control medium or with medium containing 200 ng/ml PYY. Glucose-stimulated insulin release was then measured on the indicated days (FIG. 6). Adult islets lost glucose stimulated insulin secretion within 2 days in culture in standard 10% FBS containing medium. However, PYY was able to rescue responsiveness even after 10 days in culture and longer.

Example 7

Figure 7:
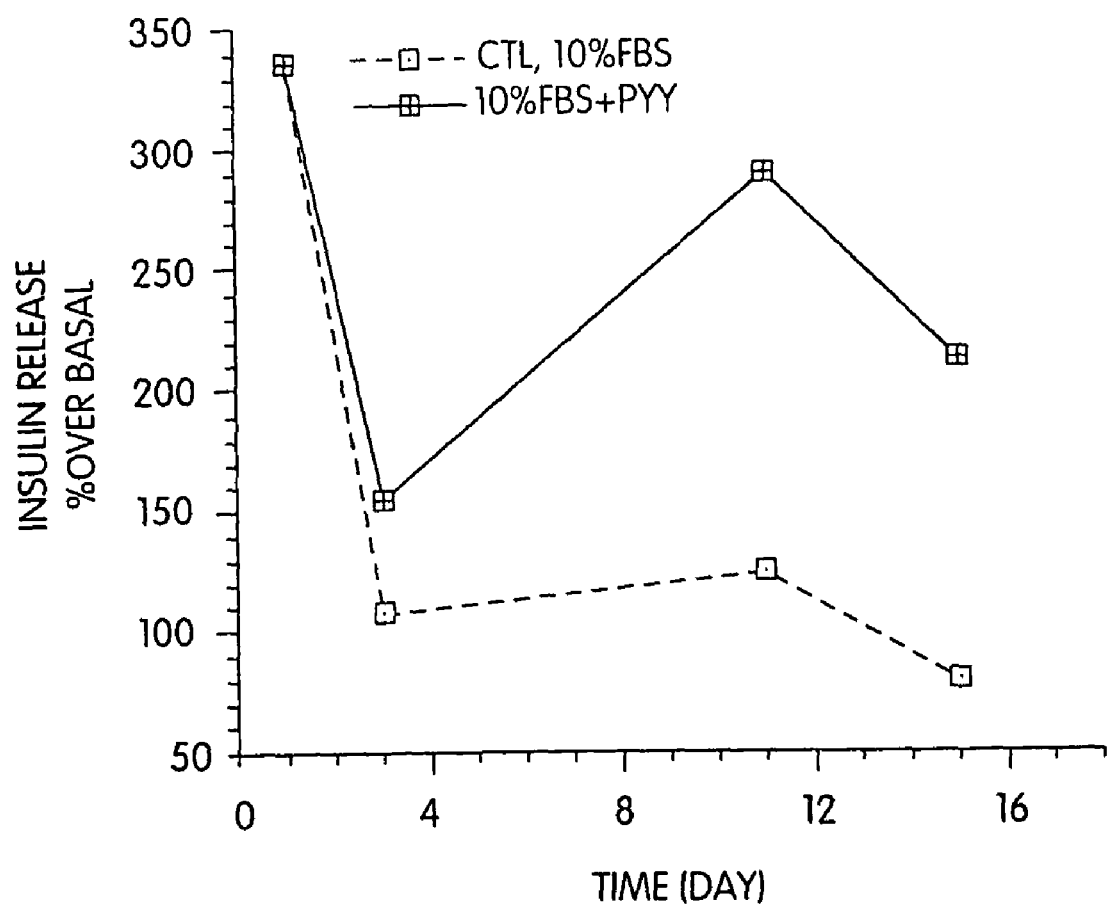
FIG. 7: The effect of PYY on gain of glucose responsivity requires activation of gene transcription.

Effect of PYY on Gain of Glucose Responsivity Requires Activation of Gene Transcription Fetal rat islets were isolate as in Example 1 and treated with 200 L/ml PYY for 5 days, with the addition of actinomycin D at 0.1 µg/ml for the last 16 hours, with and without the addition of 1 µM IBMX Glucose-stimulated insulin release was then measured in each culture group (FIG. 7). Actinomycin D could completely inhibit the gain of function induced by PYY as measured by insulin release. This is not due to non-specific toxicity of the drug to the islets, since IBMX can still induce insulin exocytosis in islets treated with actinomycin D.

Example 8

Effect of Actinomycin D is not Mediated by Lowering of Islet Insulin Content

Figure 8:
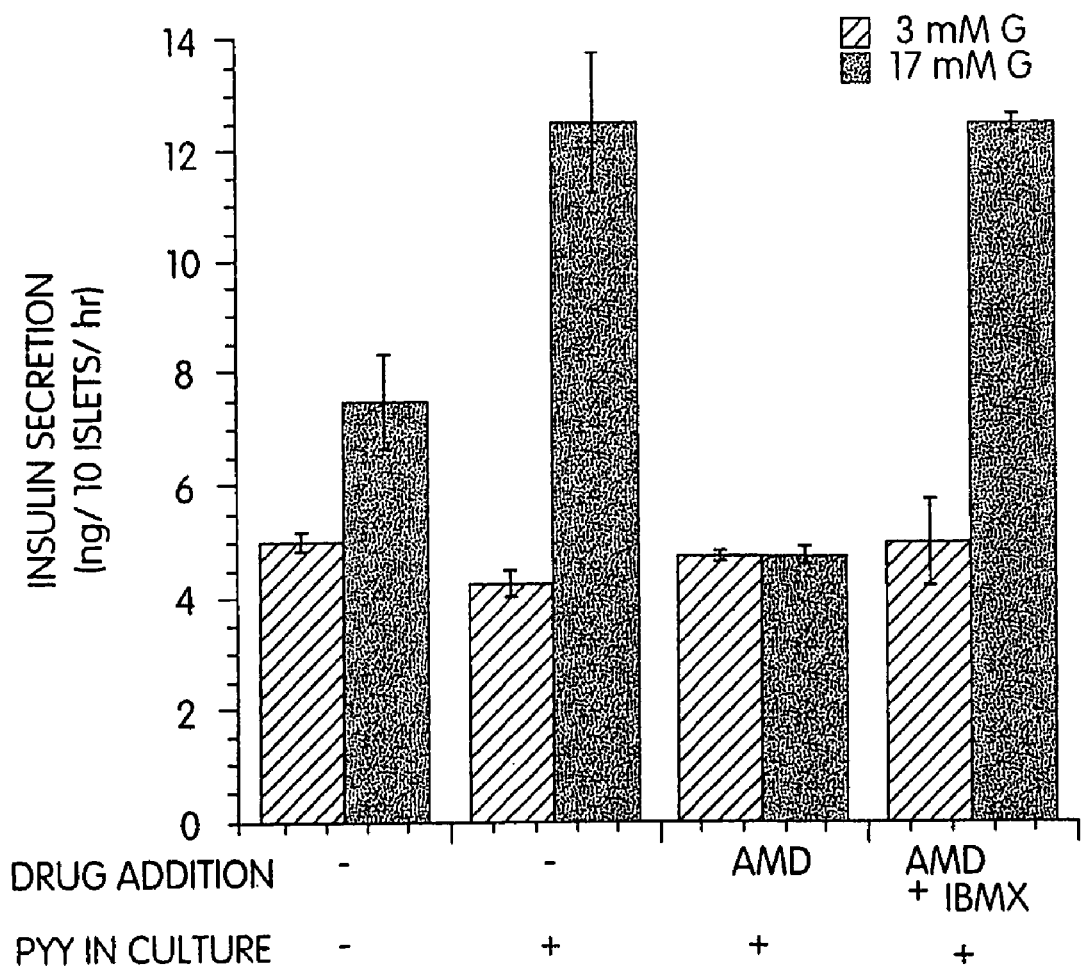
FIG. 8: The effect of actinomycin D is not mediated by lowering of islet insulin content.
Figure 9:
FIG. 9: The presence of PYY does not affect basal secretion rate.

Fetal rat islets were isolated as in Example 1 and treated with 200µ/ml PYY for 5 days, with the addition of actinomycin D at 0.1, 0.2, 0.5 and 1.0 µg/ml for the last 16 hours. Insulin content was then measured in each culture group (FIG. 8). The table shows that increasing the amount of actinomycin D did not significantly decrease overall islet insulin content.

Example 9

PYY does not Affect Basal Secretion Rate

E21 and P14 rat islets were isolated as in Example 1 and treated with 200 ng/ml PYY. Islets were then washed and assayed for glucose responsivity, as measured by insulin release. PYY was then added to the assay buffer (Kreb's-Ringer Phosphate) to determine if the presence of PYY acutely affected either the basal or stimulated insulin secretion rates. Glucose-stimulated insulin release was then measured in each culture group (FIG. 8). The effect of PYY addition into the assay buffer was negligible, indicating that the primary effect of PYY is exerted during the culture period in which it is present. Freshly isolated P14 islets were included as a positive control.

Example 10

Effect of PYY on Restoring Glucose Response in Adult Rat Islets

Figure 10A:
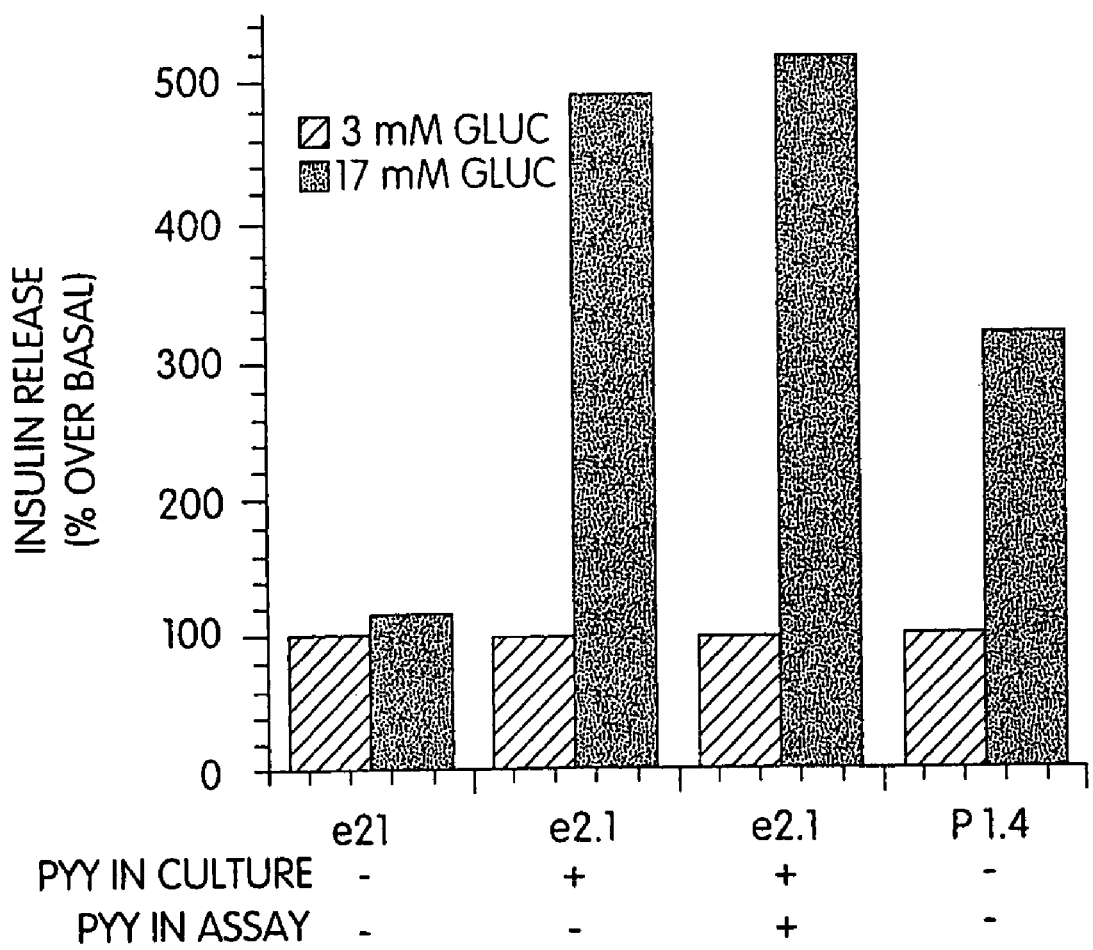
FIG. 10A and FIG. 10B: Effect of PYY on restoring glucose response in rat adult islets.
Figure 10B:
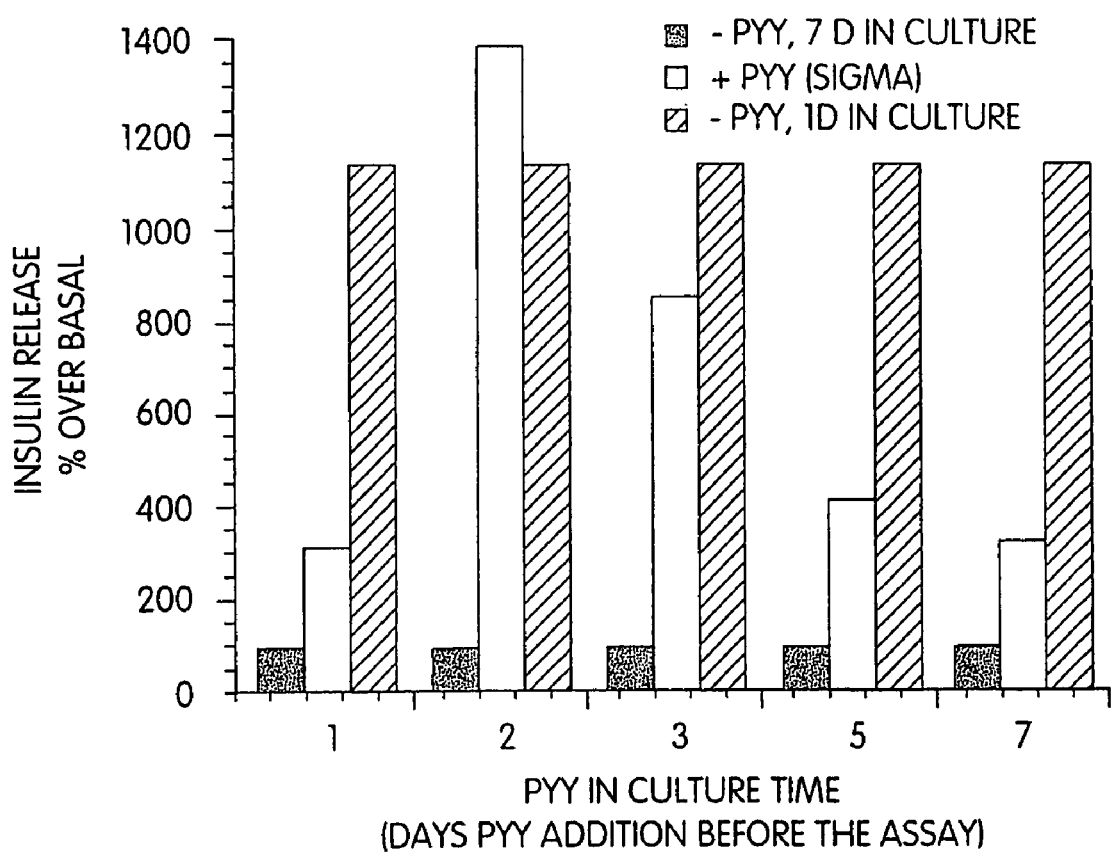

Adult rat islets were isolated as in Example 1 and cultured in 10% FBS for 7 days, during which time 200 ng/ml PYY was added to the culture medium at the days indicated in FIG. 10A. Seven day cultured islets alone lost glucose responsiveness, however, when PYY was added in the last 2 to 3 days before the end of the assay, it restored the glucose response. When PYY was present in the culture for five days or longer, it appeared to have lost its restoration function, suggesting the possibility of peptide signal degradation (FIG. 10B).

Example 11

Effect of PYY In Vivo

The Zucker Diabetic Fatty (ZDF) male rat is a recently developed inbred (>F30 Generations) rat model that spontaneously expresses diabetes in all fa/fa males fed a standard rodent diet Purina 5008. In ZDF fa-fa males hyperglycemia begins to develop at about seven weeks of age and glucose levels (fed) typically reach 500 mg/DL by 10 to 11 weeks of age. Insulin levels (fed) are high during the development of diabetes. However, by 19 weeks of age insulin drops to about the level of lean control litter mates. Triglyceride and cholesterol levels of obese rats are normally higher than those of leans.

In the present experiment, three groups of 7-week old ZDF rats, with 6 rats per group, received the infusion treatment by ALZA pump for 14 days: 1) vehicle control, 2) and 3), PYY with two different doses, 100 pmol/kg/hr and 500 pmol/kg/hr respectively. Four measurements were taken before the infusion and after the infusion at day 7 and day 14:1) plasma glucose level, 2) plasma insulin level, and 3) plasma triglycerides (TG) level, as well as oral glucose tolerance (OGTT) test.

Human, synthetic PYY was purchased from Sigma, and was re-suspended into 0.15 M NaCl with 0.5% BSA. The three solutions thus comprised vehicle (0.15 M NaCl with 0.5% BSA), PYY 100 pmol/kg/hr, and PYY 500 pmol/kg/hr.

Figure 11:
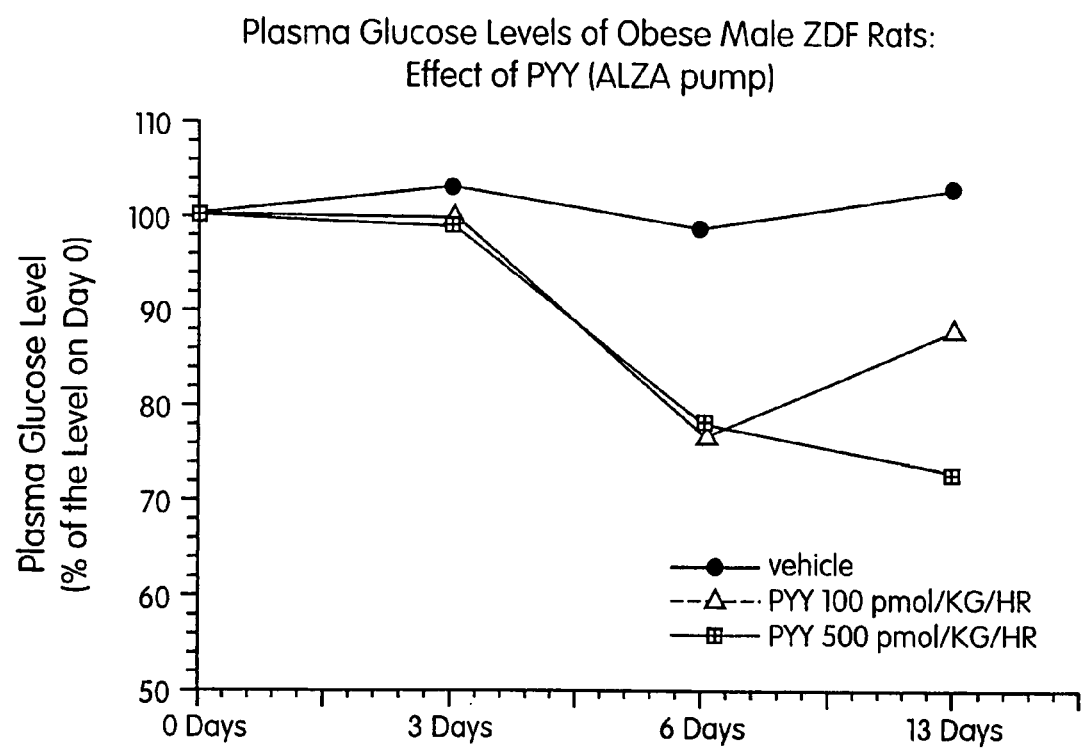
FIG. 11: Effect of PYY on rat plasma glucose levels.

FIG. 11 shows how the plasma glucose level (fed) was reduced over period of 14 days test in PYY-treated groups. The mean fed-plasma glucose level decreases over two weeks in PYY treated groups: it fell 40 mg/dl in the group receiving 100 pmol PYY and fell 82 mg/dl in the group receiving 500 pmol PYY. By contrast, it rose 11 mg/dl in the vehicle group.

The data were plotted as percentage of the glucose level on day 0. These changes are statistically significant over time (P value=0.05). It is well documented that the fed plasma glucose level increases in ZDF rats to between 300 and 350 mg/dl as they develop of diabetes from 7 to 9 weeks. The fact that the plasma glucose level dropped to 27% at 9 weeks of age in PYY treated groups suggests that PYY may have an effect on regulating fed plasma glucose level.

Figure 12:
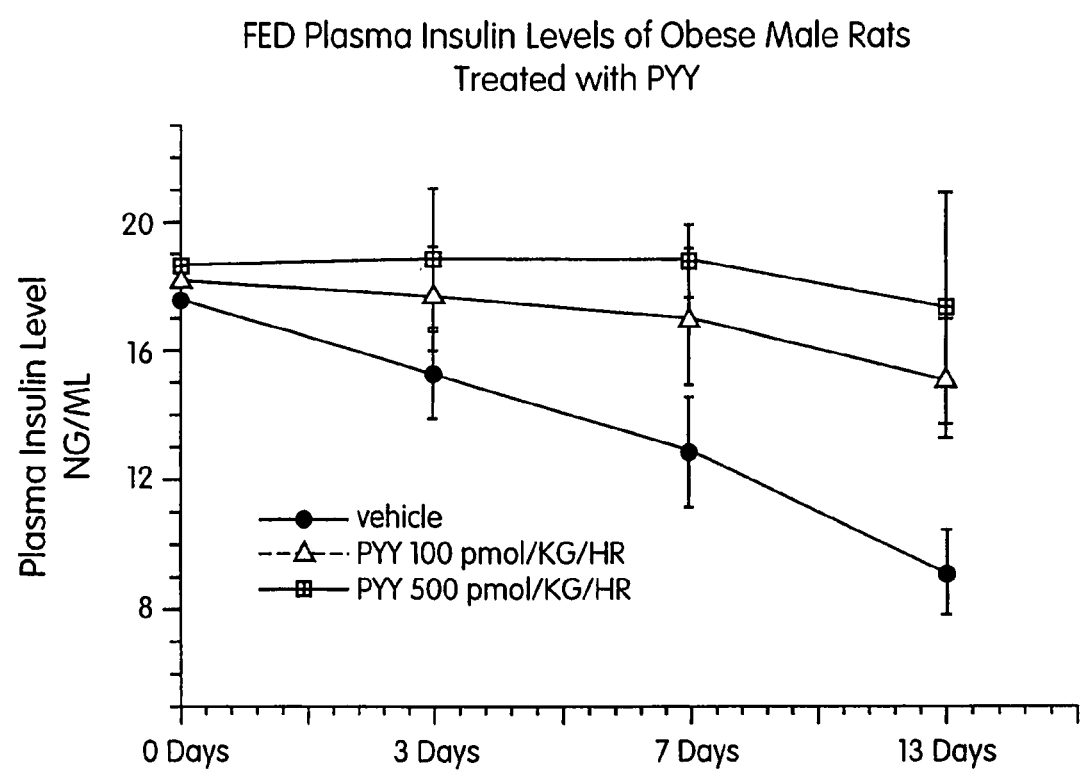
FIG. 12: Effect of PYY on rat plasma insulin levels.

FIG. 12 demonstrates how the plasma insulin level (fed) was preserved over period of 14 days test in PYY treated groups. The plasma insulin levels in the control group dropped from 17.5+/−0.9 to 9.1+/−1.3 ng/ml, whereas the insulin level was preserved in the PYY treated groups: it went from 18.2+/−3.6 to 15.1+/−1.8 ng/ml in the group receiving 100 pmol PYY, went from 18.6+/−1.2 to 17.3+/−3.6 ng/ml in the group receiving 500 pmol PYY. Fed plasma insulin levels normally begin to decrease and eventually reach 1-5 ng/ml in these ZDF rats during as they develop diabetes from 7 week to post 9 weeks. The fact that plasma insulin level was preserved in PYY treated groups, but not in control groups, suggests that PYY may have an effect on β cell insulin release in response to high plasma glucose level in these pre-diabetic rats.

Figure 13:
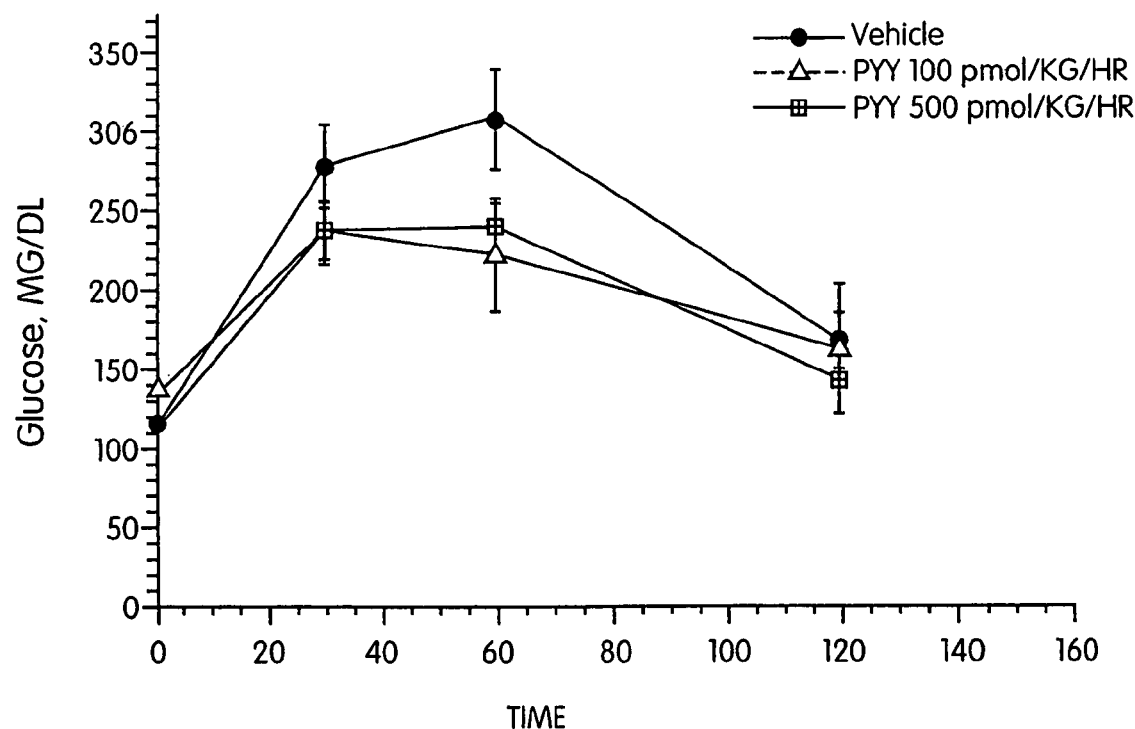
FIG. 13: Effect of PYY on rat glucose tolerance.

FIG. 13 illustrates how glucose tolerance was improved in an OGTT test in PYY treated groups after 7 days of infusion. The rate of recovering to normal fasting glucose level in PYY treated groups (with 100 pmol/kg/hr) is significantly higher than that of the vehicle group during the last 60 to 120 min of the OGTT test (P value=0.0024).

Figure 14:
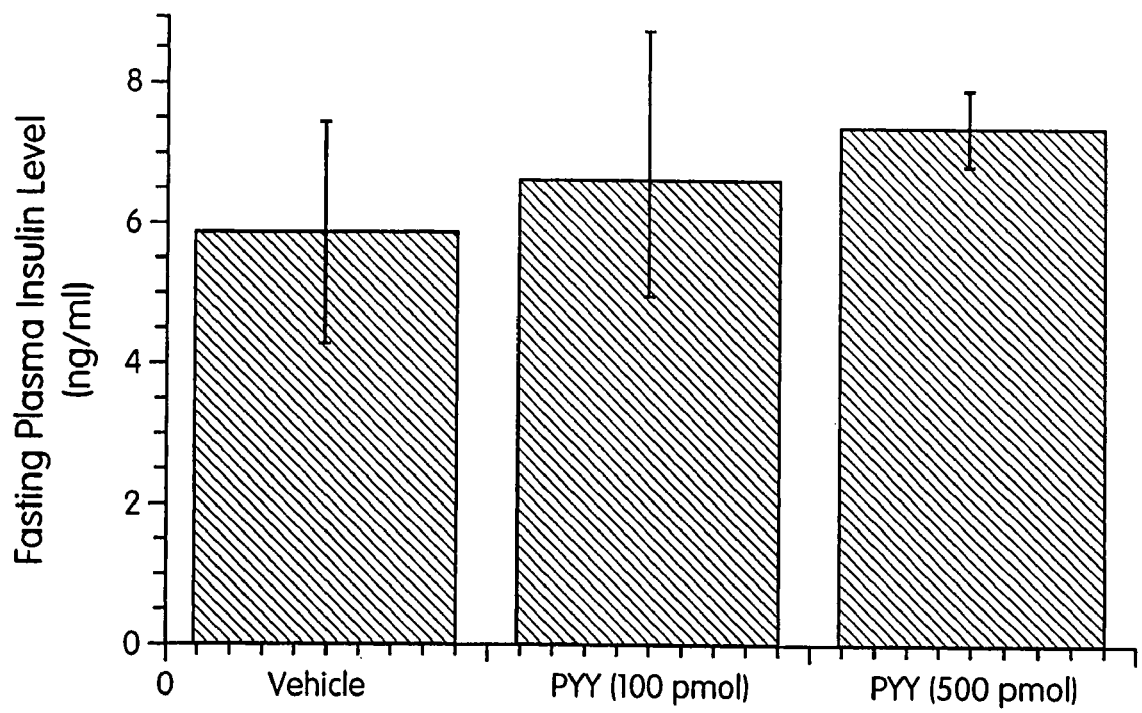
FIG. 14: Effect of PYY on plasma insulin levels in fasting rats.

FIG. 14 depicts how fasting plasma insulin level was higher in PYY treated groups after 14 days of the infusion. Fasting plasma insulin level of the rats treated with PYY was greater than the vehicle control. This is consistent with the observation in fed insulin level showing here in FIG. 12. Again, it suggested that PYY might affect β cell insulin release in respond to the plasma glucose level.

The preliminary in vivo data suggest that PYY may affect on 1) regulation of insulin release by β cells in response to plasma glucose level, 2) control of the fed plasma glucose level and 3) improvement of glucose tolerance in 7-9 week old pre-diabetic rats.

All of the above-cited references and publications are incorporated herein by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for treating a disease associated with altered glucose metabolism, comprising administering to an animal having a disease associated with altered glucose metabolism a composition comprising an amount of a PYY peptidomimetic, wherein said PYY peptidomimetic comprises a peptide having the amino acid sequence of SEQ ID NO: 2, wherein the amount of PYY peptidomimetic is sufficient to treat the disease in said animal, and wherein the PYY peptidomimetic binds a PYY receptor and promotes glucose responsiveness.

2. The method of claim 1, wherein said disease is a condition selected from insulin resistance, glucose intolerance or glucose non-responsiveness.

3. The method of claim 1, wherein said disease is hyperglycemia.

4. The method of claim 1, wherein said disease is obesity.

5. The method of claim 1, wherein said disease associated with altered glucose metabolism comprises hyperlipidemia or hyperlipoproteinemia.

6. A method for treating a disease associated with altered glucose metabolism, comprising administering to an animal having a disease associated with altered glucose metabolism a composition comprising an amount of a PYY peptidomimetic effective to treat said disease associated with altered glucose metabolism, wherein said PYY peptidomimetic comprises a peptide with at least 80% amino acid identity to SEQ ID No. 2, and wherein said PYY peptidomimetic binds a PYY receptor and promotes glucose responsiveness.

7. The method of claim 6, wherein the PYY peptidomimetic comprises a polypeptide at least 85% identical to SEQ ID NO: 2.

8. The method of claim 6, wherein the PYY peptidomimetic comprises a polypeptide at least 90% identical to SEQ ID NO: 2.

9. The method of any one of claims 1, 6, 3, and 4, wherein said composition further comprises at least one of a dipeptidylpeptidase inhibitor, insulin or GLP-1.

10. The method of any one of claims 1, 6, 3, and 4, wherein said PYY peptidomimetic is conjointly administered either simultaneously, sequentially, or separately with at least one of a dipeptidylpeptidase inhibitor, insulin, or GLP-1.

11. The method of claim 10, wherein said dipeptidylpeptidase inhibitor is DPIV.

12. The method of any one of claims 1, 6, 3, and 4, wherein said PYY peptidomimetic enhances or recovers glucose responsiveness.

13. The method of any one of claims 1, 6, 3, and 4, wherein said animal is selected from the group consisting of a human and a rat.

14. The method of claim 13, wherein said animal is a human.

15. The method of any one of claims 1, 6, 3, and 4, wherein the composition further comprises GLP-1.

16. The method of any one of claims 1, 6, 3, and 4, wherein the treatment comprises nasal administration of the composition.

17. The method of any one of claims 1, 6, 3, and 4, wherein the PYY peptidomimetic comprises PYY(3-36) of SEQ ID NO: 2.

18. The method of any one of claims 1, 6, 3, and 4, wherein the peptidomimetic comprises PYY(3-36) of SEQ ID NO: 2, the composition further comprises GLP-1, and the treatment comprises nasal administration of the composition.

19. The method of any one of claims 1, 6, 3, and 4, wherein said PYY peptidomimetic also promotes glucose-responsiveness of pancreatic cells.

20. The method of any one of claims 1, 6, 3, and 4, wherein said PYY peptidomimetic also inhibits intestinal motility.

21. The method of any one of claims 1, 6, 3, and 4, wherein said PYY peptidomimetic also inhibits mesenteric blood flow.

22. The method of any one of claims 1, 6, 3, and 4, wherein said PYY peptidomimetic also mediates gastric, pancreatic, or intestinal exocrine secretion.

23. The method of any one of claims 1, 6, 3, and 4, wherein said PYY peptidomimetic also stimulates net absorption of nutrients.

24. A method for maintaining or restoring normal pancreatic cell function in an animal having impaired pancreatic cell function, wherein the function is glucose responsivity or glucose sensing, comprising administering to said animal an amount of a PYY peptidomimetic, wherein said PYY peptidomimetic comprises a peptide having the amino acid sequence of SEQ ID NO: 2, wherein the amount of said PYY peptidomimetic is sufficient to maintain or restore normal pancreatic cell function, and wherein the PYY peptidomimetic binds a PYY receptor and promotes glucose-responsiveness of said pancreatic cell.

25. A method for maintaining or restoring normal pancreatic cell function to an animal having impaired pancreatic cell function, wherein the function is glucose responsivity or glucose sensing, comprising administering to said animal an amount of a PYY peptidomimetic, wherein said PYY peptidomimetic comprises a peptide with at least 80% amino acid identity to SEQ ID No. 2, wherein the amount of said PYY peptidomimetic is sufficient to maintain or restore normal pancreatic cell function to said animal, and wherein said PYY peptidomimetic binds a PYY receptor and promotes glucose-responsiveness of said pancreatic cell.

26. A method for maintaining or restoring a function of a pancreatic β cell in an animal having impaired β cell function, wherein the function is glucose responsivity or glucose sensing, comprising administering to said animal a composition comprising an amount of a PYY peptidomimetic, wherein said PYY peptidomimetic comprises a peptide with at least 80% amino acid identity to SEQ ID NO: 2, wherein the amount of said PYY peptidomimetic is sufficient to maintain or restore the function of said pancreatic β cell, and wherein the PYY peptidomimetic binds a PYY receptor and promotes glucose-responsiveness of said pancreatic cell.

27. A method for promoting a gain of glucose responsivity in pancreatic β cells in an animal having a metabolic disorder, comprising administering to said animal a composition including a PYY peptidomimetic in an amount effective to promote a gain of glucose responsivity, wherein said PYY peptidomimetic comprises a peptide with at least 80% amino acid identity to SEQ ID No. 2, and wherein the PYY peptidomimetic binds a PYY receptor and promotes glucose-responsiveness.

28. A method for inducing or enhancing the glucose-responsiveness of a pancreatic cell in an animal having a metabolic disorder, which pancreatic cell has impaired glucose-responsiveness, comprising administering to said animal an amount of a PYY peptidomimetic, wherein said PYY peptidomimetic comprises a peptide with at least 80% amino acid identity to SEQ ID No. 2, wherein the amount of said PYY peptidomimetic is sufficient to induce or enhance the glucose-responsiveness of said pancreatic cell, and wherein the PYY peptidomimetic binds a PYY receptor and promotes glucose-responsiveness of said pancreatic cell.

29. A method for inducing or enhancing glucose metabolism in an animal having a disease associated with abnormal glucose metabolism, comprising administering to said animal a composition including an amount of a PYY peptidomimetic, wherein said PYY peptidomimetic comprises a peptide with at least 80% amino acid identity to SEQ ID No. 2, wherein the amount of PYY peptidomimetic is effective to induce or enhance glucose responsiveness in said animal, thereby inducing or enhancing glucose metabolism in said animal, and wherein the PYY peptidomimetic binds a PYY receptor and promotes glucose responsiveness.

30. The method of claim 29, wherein said disease is a condition selected from insulin resistance, glucose intolerance or glucose non-responsiveness.

31. The method of claim 29, wherein said disease is Type II diabetes mellitus (NIDD).

32. A method for inducing, enhancing, or maintaining glucose-responsiveness of a pancreatic cell in an animal having a metabolic disorder, which pancreatic cell has impaired glucose-responsiveness, comprising administering to said animal a composition comprising an amount of a PYY peptidomimetic, wherein the amount of said PYY peptidomimetic is sufficient to induce, enhance, or maintain the glucose-responsiveness of said pancreatic cell, wherein said PYY peptidomimetic comprises a peptide with at least 80% amino acid identity to SEQ ID No. 2, and wherein said PYY peptidomimetic binds a PYY receptor and promotes glucose-responsiveness of said pancreatic cell.

33. The method of any one of claims 25-32, wherein the PYY peptidomimetic comprises a polypeptide at least 85% identical to SEQ ID NO: 2.

34. The method of any one of claims 25-32, wherein the PYY peptidomimetic comprises a polypeptide at least 90% identical to SEQ ID NO: 2.

* * * * *